United States Patent
Faccioli et al.

(10) Patent No.: US 10,765,373 B2
(45) Date of Patent: Sep. 8, 2020

(54) REAL-TIME DENOISING AND PREDICTION FOR A CONTINUOUS GLUCOSE MONITORING SYSTEM

(71) Applicant: Senseonics, Incorporated, Germantown, MD (US)

(72) Inventors: Simone Faccioli, Megliadino San Vitale (IT); Xiaoxiao Chen, Washington, DC (US); Andrew DeHennis, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 329 days.

(21) Appl. No.: 15/583,558

(22) Filed: May 1, 2017

(65) Prior Publication Data
US 2017/0311897 A1 Nov. 2, 2017

Related U.S. Application Data

(60) Provisional application No. 62/329,760, filed on Apr. 29, 2016.

(51) Int. Cl.
*A61B 5/1455* (2006.01)
*A61B 5/00* (2006.01)
(Continued)

(52) U.S. Cl.
CPC .......... *A61B 5/7203* (2013.01); *A61B 5/0004* (2013.01); *A61B 5/0024* (2013.01);
(Continued)

(58) Field of Classification Search
None
See application file for complete search history.

(56) References Cited

U.S. PATENT DOCUMENTS

| 7,389,133 B1 | 6/2008 | Kotulla et al. |
| 7,920,906 B2 | 4/2011 | Goode, Jr. et al. |

(Continued)

FOREIGN PATENT DOCUMENTS

| EP | 1 518 495 B1 | 3/2010 |
| EP | 2 497 420 A1 | 9/2012 |

(Continued)

OTHER PUBLICATIONS

D.C. Klonoff: Benefits and limitations of self-monitoring blood glucose. J. Diabetes Sci. Technol. 2007; 1: 130-2.
(Continued)

*Primary Examiner* — Eric F Winakur
*Assistant Examiner* — Marjan Fardanesh
(74) *Attorney, Agent, or Firm* — Rothwell, Figg, Ernst & Manbeck, P.C.

(57) ABSTRACT

An analyte monitoring system may include an analyte sensor and a transmitter. The analyte sensor may include an indicator element that exhibits one or more detectable properties based on an amount or concentration of an analyte in proximity to the indicator element. The analyte sensor may be configured to generate one or more raw signals indicative of one or more analyte amounts or concentrations. The transmitter may be configured to receive from the analyte sensor one or more raw signals indicative of analyte concentration. The transmitter may be configured to denoise the raw signal using a real-time filtering technique with one or more time-varying parameters. The transmitter may be configured to predict ahead of time an analyte concentration based on one or more of the received one or more raw signals using one or more prediction models.

16 Claims, 58 Drawing Sheets

(51) Int. Cl.
*A61B 5/145* (2006.01)
*G16H 20/17* (2018.01)
(52) U.S. Cl.
CPC .......... *A61B 5/0031* (2013.01); *A61B 5/0071* (2013.01); *A61B 5/14503* (2013.01); *A61B 5/14532* (2013.01); *A61B 5/4839* (2013.01); *A61B 5/725* (2013.01); *A61B 5/7246* (2013.01); *A61B 5/7264* (2013.01); *A61B 5/7275* (2013.01); *A61B 2560/0219* (2013.01); *A61B 2560/0223* (2013.01); *G16H 20/17* (2018.01)

(56) References Cited

U.S. PATENT DOCUMENTS

| | | |
|---|---|---|
| 8,394,021 B2 | 3/2013 | Goode et al. |
| 9,220,449 B2 | 12/2015 | Pryor et al. |
| 9,557,582 B2 | 1/2017 | Honore et al. |
| 9,629,578 B2 | 4/2017 | Hayter et al. |
| 9,662,056 B2 | 5/2017 | Budiman et al. |
| 9,788,354 B2 | 10/2017 | Miller et al. |
| 9,804,148 B2 | 10/2017 | Hayter et al. |
| 10,028,686 B2 | 7/2018 | Hayter |
| 2011/0029269 A1 | 2/2011 | Hayter et al. |
| 2011/0237917 A1 | 9/2011 | Roy et al. |
| 2013/0085679 A1 | 4/2013 | Budiman |
| 2013/0245981 A1 | 9/2013 | Estes et al. |
| 2013/0281807 A1 | 10/2013 | Hayter et al. |
| 2014/0118138 A1 | 5/2014 | Cobelli et al. |
| 2014/0378791 A1 | 12/2014 | DeHennis et al. |

FOREIGN PATENT DOCUMENTS

| | | |
|---|---|---|
| EP | 2 329 763 B1 | 6/2017 |
| EP | 2 770 907 B1 | 7/2018 |
| WO | 03/082098 A2 | 10/2003 |
| WO | 2009/136372 A1 | 11/2009 |

OTHER PUBLICATIONS

D. C. Klonoff: Continuous glucose monitoring: Roadmap for 21st century diabetes therapy. Diabetes Care. 2005; 28: 1231-9.
J. H. Nichols and D. C. Klonoff: The need for performance standards for continuous glucose monitors. J. Diabetes Sci. Technol. 2007; 1: 92-5.
A. Facchinetti, G. Sparacino, C. Cobelli: Signal Processing Algorithms Implementing the "Smart Sensor" Concept to Improve Continuous Glucose Monitoring in Diabetes. J. Diabetes Sci. Technol. 2013; 7 (5): 1308-18.
C. C. Palerm and B.W. Bequette: Hypoglycemia detection and prediction using continuous glucose monitoring—A study on hypoglycemic clamp data. J. Diabetes Sci. Technol. 2007; 1: 624-9.
M. Mortellaro, A. DeHennis: Performance characterization of an abiotic and fluorescent-based continuous glucose monitoring system in patients with type 1 diabetes. Biosensors and Bioelectronics. 2014; 61: 227-31.
A. DeHennis, M. Mortellaro, S. Ioacara. Multiple Study of an Implanted Continuous Glucose Sensor Over 90 Days in Patients With Diabetes Mellitus. J. Diabetes Sci. Technol. 2015; 9 (5): 951-6.
American Diabetes Association: Diagnosis and classification of diabetes mellitus. Diabetes Care. 2011; 34 (1): S62-9.
Hindle, E.J., G.M. Rostron, and J.A. Gatt: The estimation of serum fructosamine: an alternative measurement to glycated haemoglobin. Ann Clin Biochem. 1985; 22 (1): 84-9.
Evans, J.M., et al.: Frequency of blood glucose monitoring in relation to glycaemic control: observational study with diabetes database. BMJ. 1999; 319 (7202): 83-6.
D. B. Keenan, J. J. Mastrototaro, G. Voskanyan, and G. M. Steil: Delays in Minimally Invasive Continuous Glucose Monitoring Devices: A Review of Current Technology. J Diabetes Sci. Technol. 2009; 3 (5): 1207-14.
Christiansen M, Bailey T, Watkins E, Liljenquist D, Price D, Nakamura K, Boock R, Peyser T.: A new-generation continuous glucose monitoring system: improved accuracy and reliability compared with a previous-generation system. Diabetes Technol. Ther. 2013; 15 (10): 881-8.
O. Amir, D. Weinstein, S. Zilberman, M. Less, D. Perl-Treves, H. Primack, A. Weinstein, E. Gabis, B. Fikhte, and A. Karasik: Continuous Noninvasive Glucose Monitoring Technology Based on "Occlusion Spectroscopy". J Diabetes Sci. Technol. 2007; 1 (4): 463-9.
L. Heinemann, G. Schmelzeisen-Redeker: Non-invasive continuous glucose monitoring in Type I diabetic patients with optical glucose sensors. Diabetologia. 1998; 41: 848-54.

FIG. 18

| CGM ROC (mg/dl/min) | | HEXOKINASE ROC (mg/dl/min) | | | | | |
|---|---|---|---|---|---|---|---|
| | | <-2 | [-2,-1) | [-1,1] | (1,2] | >2 | Total |
| <-2 | Count | 6 | 10 | 4 | 0 | 0 | 20 |
| | % within YSI | 40.0% | 10.8% | 0.5% | 0.0% | 0.0% | |
| [-2,-1) | Count | 5 | 30 | 44 | 0 | 0 | 79 |
| | % within YSI | 33.3% | 32.3% | 5.1% | 0.0% | 0.0% | |
| [-1,1] | Count | 4 | 53 | 782 | 49 | 16 | 904 |
| | % within YSI | 26.7% | 57.0% | 89.9% | 55.7% | 53.3% | |
| (1,2] | Count | 0 | 0 | 34 | 25 | 3 | 62 |
| | % within YSI | 0.0% | 0.0% | 3.9% | 28.4% | 10.0% | |
| >2 | Count | 0 | 0 | 6 | 14 | 11 | 31 |
| | % within YSI | 0.0% | 0.0% | 0.7% | 15.9% | 36.7% | |
| Total | Count | 15 | 93 | 870 | 88 | 30 | |

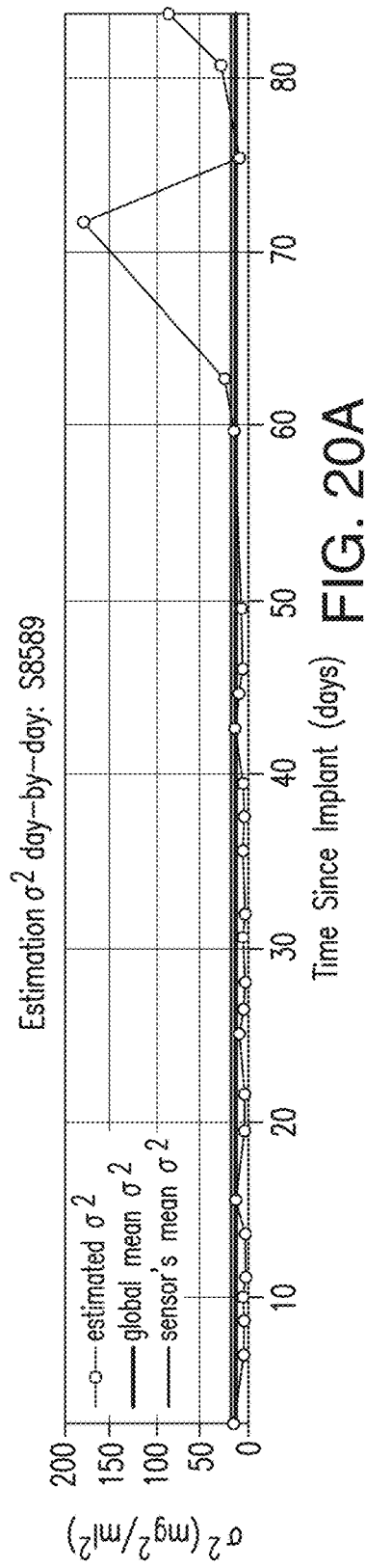
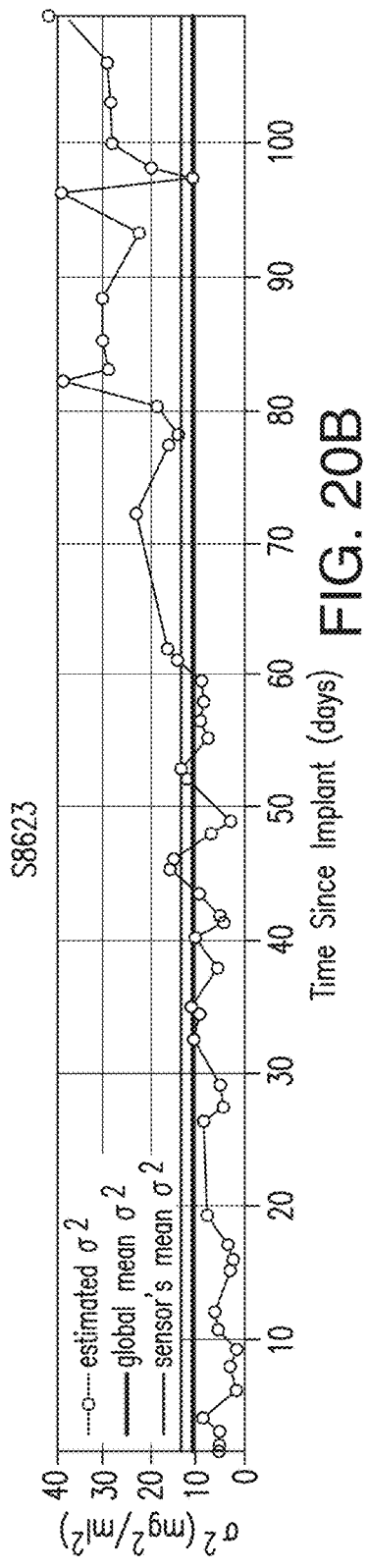
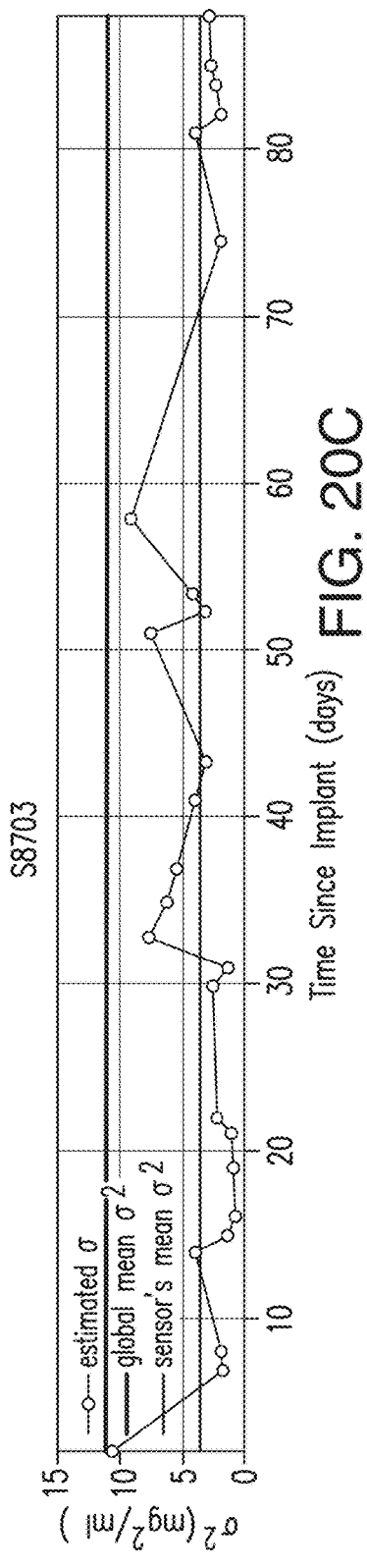

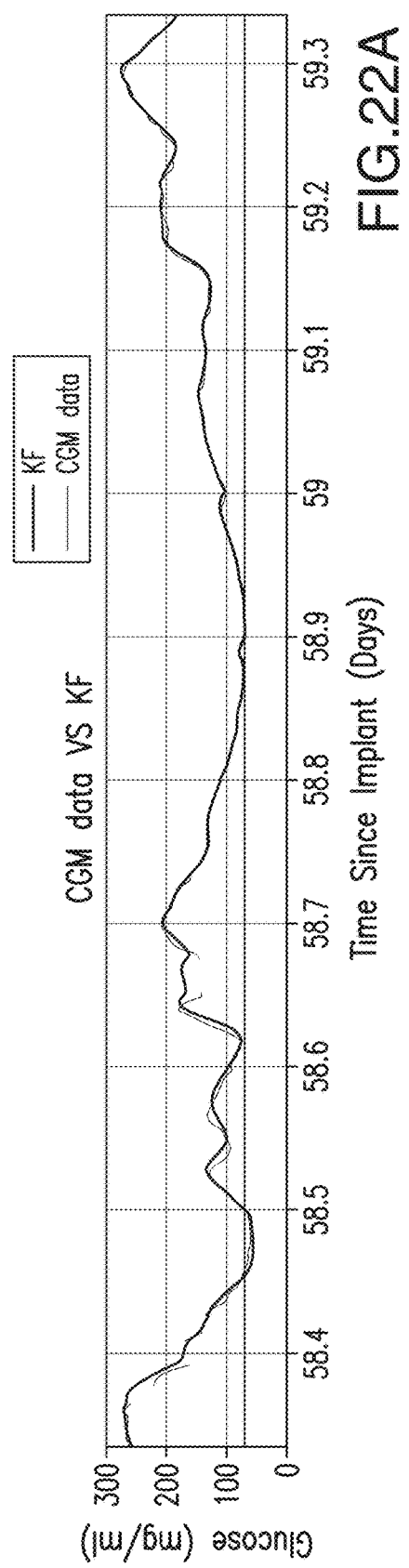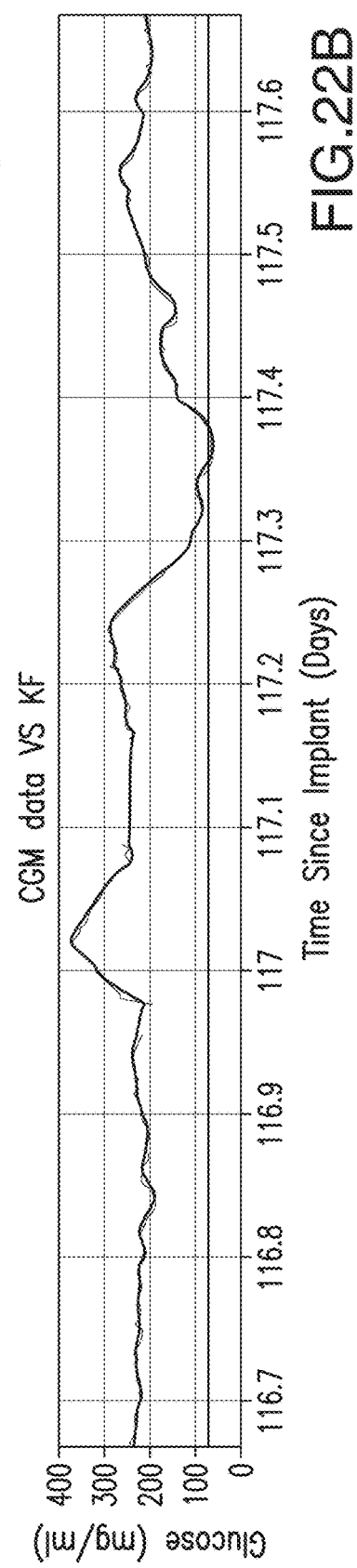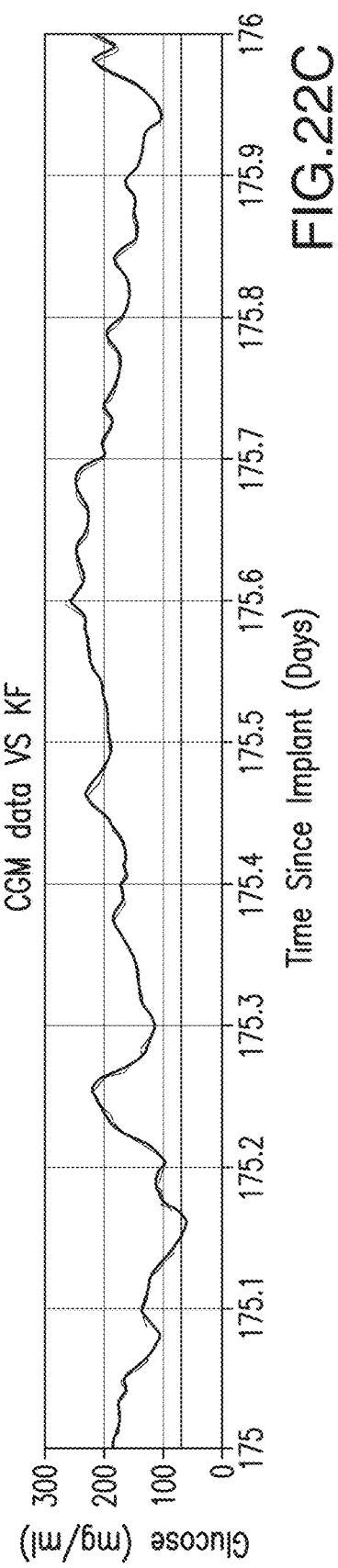

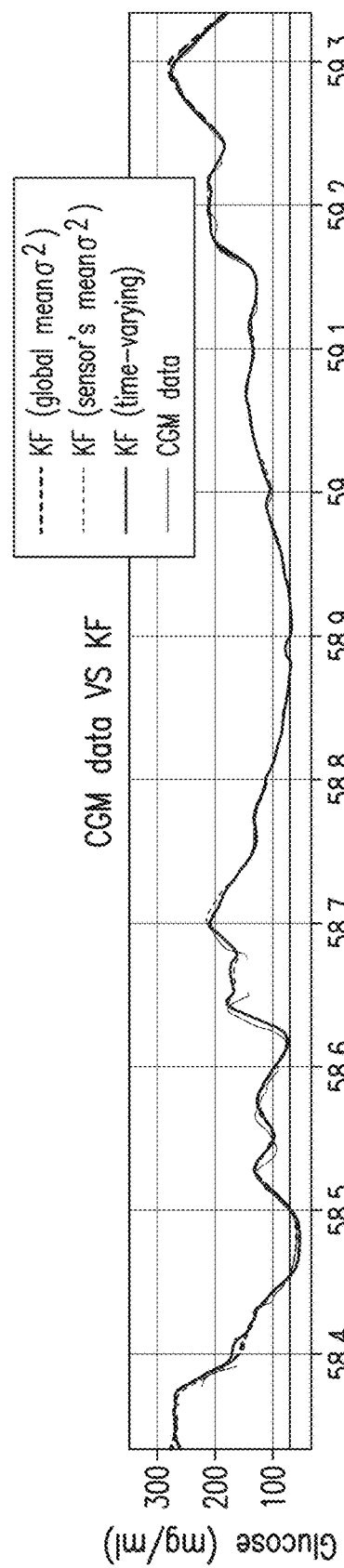
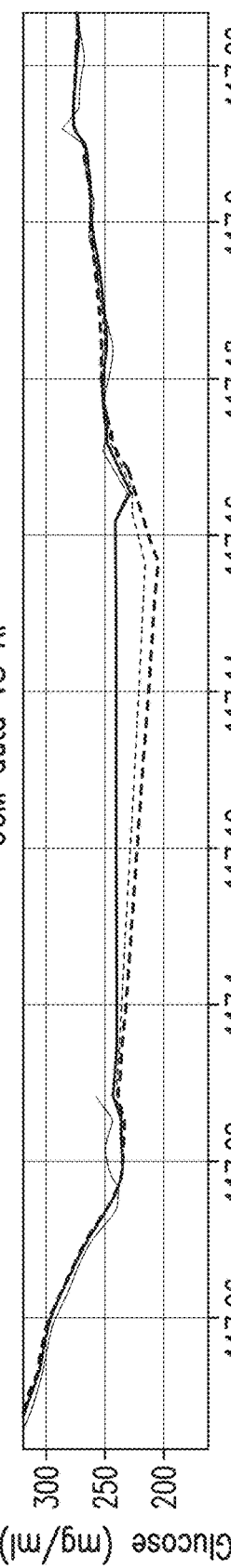
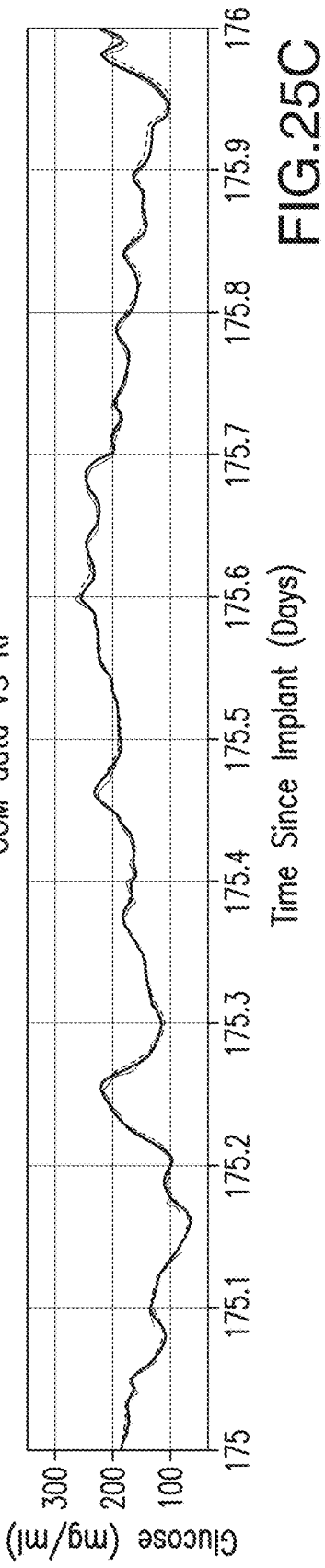
FIG.25A
FIG.25B
FIG.25C

FIG. 26

|  | YSI | | | | FS | | | |
| --- | --- | --- | --- | --- | --- | --- | --- | --- |
|  | MARD ± SD (%) | | MAD ± SD (mg/dl) | | MARD ± SD (%) | | MAD ± SD (mg/dl) | |
| Not filtered CGM | 10.97 | 2.91 | 13.52 | 6.17 | 13.75 | 2.49 | 15.39 | 6.36 |
| Filtered CGM | 12.25 | 2.96 | 16.85 | 8.43 | 15.46 | 3.14 | 19.95 | 8.75 |
| Filtered CGM (total $\sigma^2$) | 19.08 | 15.38 | 20.14 | 13.31 | 27.38 | 23.20 | 40.61 | 35.54 |
| Filtered CGM (sensor $\sigma^2$) | 18.55 | 14.05 | 19.59 | 12.13 | 27.38 | 23.41 | 40.59 | 34.70 |

FIG. 27

|  | ESOD ± SD (%) | | RMSE ± SD (mg/dl) | | SRG ± SD | | Time lag ± SD (min) | |
| --- | --- | --- | --- | --- | --- | --- | --- | --- |
| Not filtered CGM | 5284.53 | 1674.94 |  |  |  |  |  |  |
| Filtered CGM | 2066.80 | 498.50 | 7.53 | 4.72 | 0.60 | 0.07 | -1.24 | 2.24 |
| Filtered CGM (total $\sigma^2$) | 969.06 | 643.50 | 12.52 | 9.64 | 0.82 | 0.11 | -5.42 | 0.61 |
| Filtered CGM (sensor $\sigma^2$) | 985.44 | 631.65 | 12.30 | 10.41 | 0.81 | 0.11 | -5.14 | 1.75 |

FIG. 28

| CGM ROC (mg/dl/min) | | YSI ROC (mg/dl/min) | | | | | |
| --- | --- | --- | --- | --- | --- | --- | --- |
|  |  | <-2 | [-2,-1) | [-1,1] | (1,2] | >2 | Total |
| <-2 | Count | 46 | 73 | 24 | 1 | 0 | 144 |
|  | % within YSI | 47.9% | 10.8% | 0.3% | 0.1% | 0.0% |  |
| [-2,-1) | Count | 31 | 350 | 437 | 1 | 0 | 819 |
|  | % within YSI | 32.3% | 51.6% | 5.1% | 0.1% | 0.0% |  |
| [-1,1] | Count | 19 | 255 | 7703 | 360 | 20 | 8357 |
|  | % within YSI | 19.8% | 37.6% | 89.8% | 39.4% | 14.0% |  |
| (1,2] | Count | 0 | 0 | 385 | 425 | 36 | 846 |
|  | % within YSI | 0.0% | 0.0% | 4.5% | 46.5% | 25.2% |  |
| >2 | Count | 0 | 0 | 31 | 127 | 87 | 245 |
|  | % within YSI | 0.0% | 0.0% | 0.4% | 13.9% | 60.8% |  |
| Total | Count | 96 | 678 | 8580 | 914 | 143 | 10411 |

FIG. 29

| Filtered CGM ROC (mg/dl/min) | | YSI ROC (mg/dl/min) | | | | | |
|---|---|---|---|---|---|---|---|
| | | <-2 | [-2,-1) | [-1,1] | (1,2] | >2 | Total |
| <-2 | Count | 49 | 86 | 53 | 5 | 0 | 193 |
| | % within YSI | 50.5% | 12.7% | 0.6% | 0.5% | 0.0% | |
| [-2,-1) | Count | 25 | 337 | 524 | 7 | 0 | 893 |
| | % within YSI | 25.8% | 49.6% | 6.1% | 0.8% | 0.0% | |
| [-1,1] | Count | 23 | 255 | 7489 | 382 | 27 | 8176 |
| | % within YSI | 23.7% | 37.6% | 87.1% | 41.7% | 19.1% | |
| (1,2] | Count | 0 | 1 | 465 | 373 | 39 | 878 |
| | % within YSI | 0.0% | 0.1% | 5.4% | 40.7% | 27.7% | |
| >2 | Count | 0 | 0 | 65 | 149 | 75 | 289 |
| | % within YSI | 0.0% | 0.0% | 0.8% | 16.3% | 53.2% | |
| Total | Count | 97 | 679 | 8596 | 916 | 141 | 10429 |

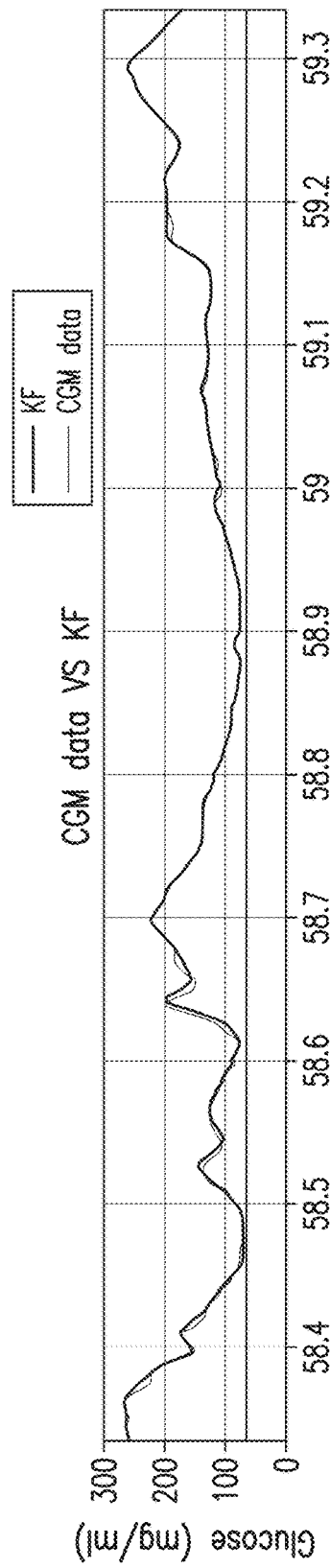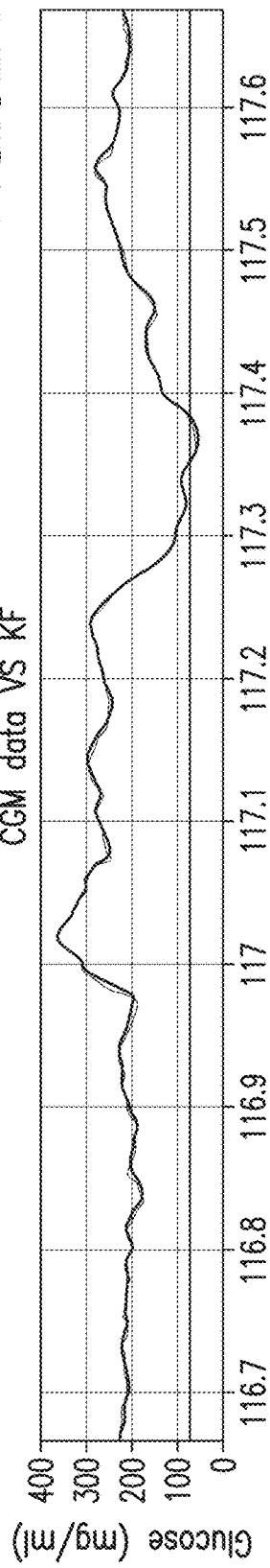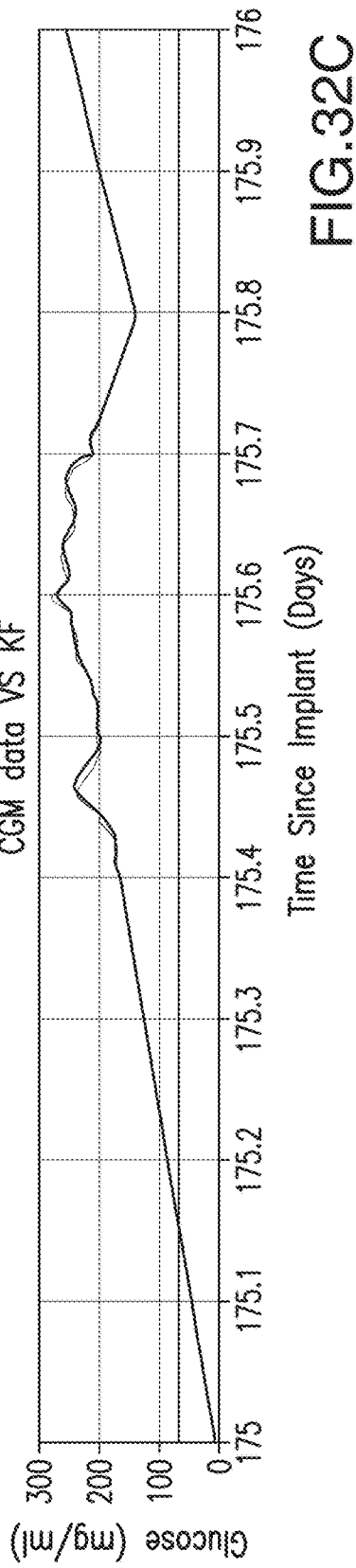

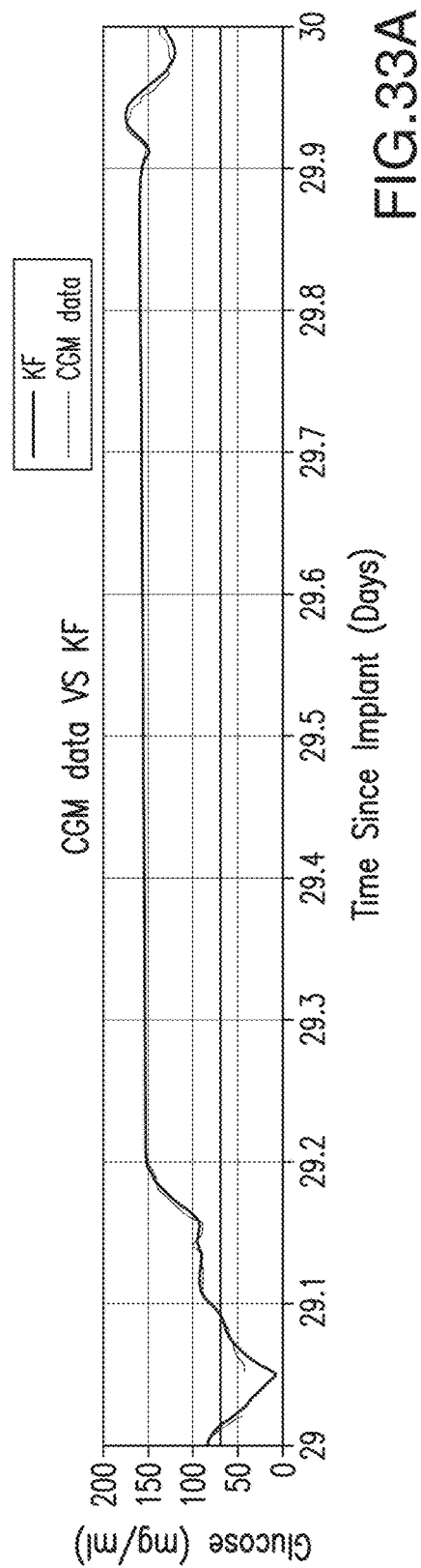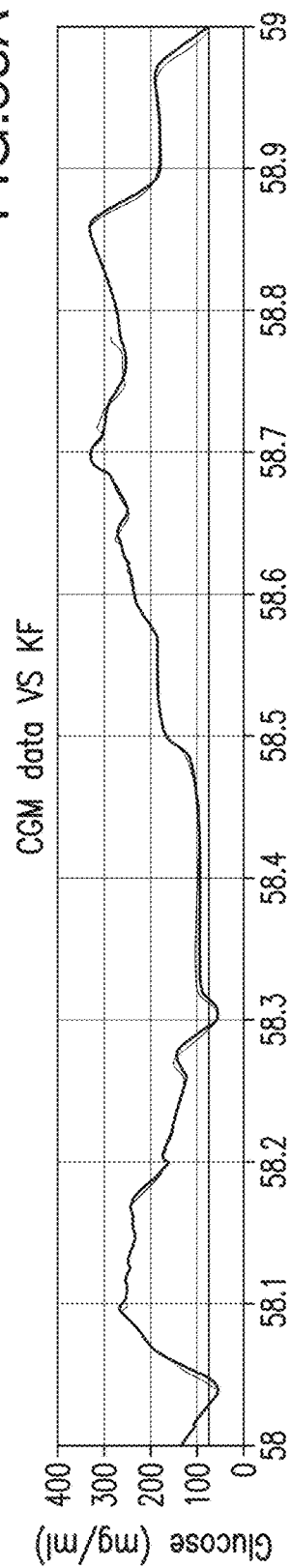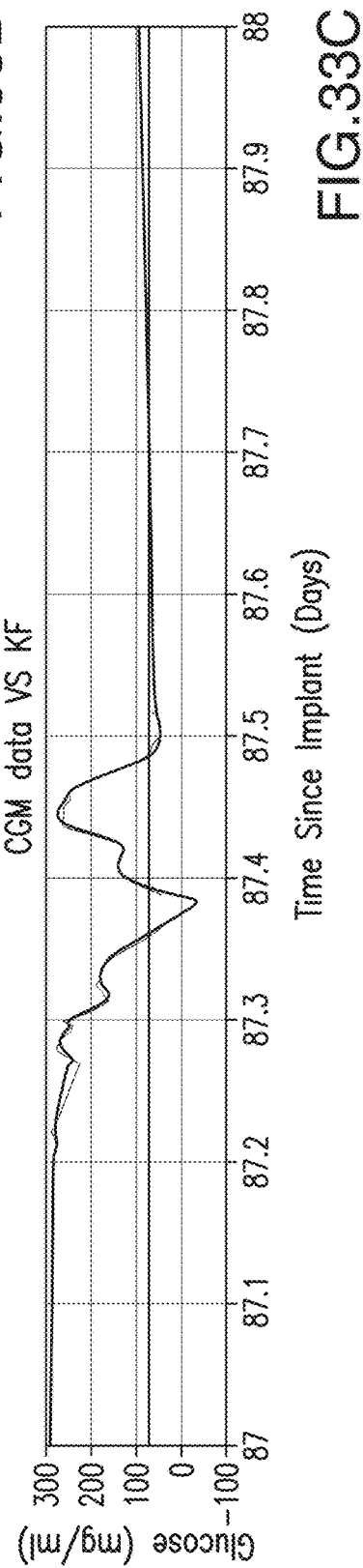

FIG. 36

| | YSI | | | | FS | | | |
|---|---|---|---|---|---|---|---|---|
| | MARD ± SD (%) | | MAD ± SD (mg/dl) | | MARD ± SD (%) | | MAD ± SD (mg/dl) | |
| Not filtered CGM | 9.98 | 2.55 | 12.23 | 6.21 | 12.50 | 1.77 | 13.81 | 8.21 |
| Filtered CGM | 11.60 | 2.76 | 17.82 | 11.89 | 15.06 | 2.31 | 22.45 | 11.00 |
| Filtered CGM (global $\sigma^2$) | 15.00 | 12.36 | 19.96 | 13.93 | 28.98 | 18.75 | 41.37 | 30.40 |
| Filtered CGM (sensor $\sigma^2$) | 14.60 | 10.85 | 19.63 | 13.08 | 29.07 | 19.40 | 40.70 | 28.81 |

FIG. 37

| | ESOD ± SD (%) | | RMSE ± SD (mg/dl) | | SRG ± SD | | Time lag ± SD (min) | |
|---|---|---|---|---|---|---|---|---|
| Not filtered CGM | 2667.84 | 1143.83 | | | | | | |
| Filtered CGM | 1371.61 | 542.03 | 6.00 | 1.72 | 0.46 | 0.11 | -0.90 | 2.05 |
| Filtered CGM (global $\sigma^2$) | 1093.83 | 924.82 | 12.95 | 9.01 | 0.60 | 0.19 | -5.30 | 1.04 |
| Filtered CGM (sensor $\sigma^2$) | 1113.25 | 974.08 | 12.99 | 9.73 | 0.59 | 0.21 | -5.29 | 1.04 |

FIG. 38

| CGM ROC (mg/dl/min) | | YSI ROC (mg/dl/min) | | | | | |
|---|---|---|---|---|---|---|---|
| | | <-2 | [-2,-1] | [-1,1] | (1,2] | >2 | Total |
| <-2 | Count | 70 | 76 | 26 | 4 | 0 | 176 |
| | % within YSI | 43.5% | 9.8% | 0.3% | 0.4% | 0.0% | |
| [-2,-1] | Count | 47 | 362 | 428 | 8 | 5 | 850 |
| | % within YSI | 29.2% | 46.5% | 4.9% | 0.8% | 1.7% | |
| [-1,1] | Count | 41 | 337 | 7955 | 464 | 80 | 8877 |
| | % within YSI | 25.5% | 43.3% | 90.5% | 43.7% | 26.7% | |
| (1,2] | Count | 2 | 2 | 339 | 444 | 67 | 854 |
| | % within YSI | 1.2% | 0.3% | 3.9% | 41.8% | 22.3% | |
| >2 | Count | 1 | 1 | 40 | 141 | 148 | 331 |
| | % within YSI | 0.6% | 0.1% | 0.5% | 13.3% | 49.3% | |
| Total | Count | 161 | 778 | 8788 | 1061 | 300 | 11088 |

FIG. 39

Table 4.8: ROC accuracy: concurrence of filtered CGM and YSI trends (Dataset 2)

| Filtered CGM ROC (mg/dl/min) | | YSI ROC (mg/dl/min) | | | | | Total |
|---|---|---|---|---|---|---|---|
| | | <-2 | [-2,-1] | [-1,1] | [1,2] | >2 | |
| <-2 | Count | 68 | 99 | 64 | 6 | 2 | 237 |
| | % within YSI | 41.0% | 12.5% | 0.7% | 0.6% | 0.7% | |
| [-2,-1] | Count | 41 | 334 | 479 | 18 | 9 | 881 |
| | % within YSI | 25.5% | 42.3% | 5.4% | 1.7% | 3.0% | |
| [-1,1] | Count | 49 | 347 | 7764 | 483 | 98 | 8741 |
| | % within YSI | 30.4% | 43.9% | 88.0% | 45.2% | 32.1% | |
| [1,2] | Count | 2 | 8 | 438 | 396 | 63 | 907 |
| | % within YSI | 1.2% | 1.0% | 5.0% | 37.0% | 20.7% | |
| >2 | Count | 3 | 2 | 73 | 166 | 133 | 377 |
| | % within YSI | 1.9% | 0.3% | 0.8% | 15.5% | 43.6% | |
| Total | Count | 161 | 790 | 8818 | 1069 | 305 | 11143 |

FIG. 43

| PH (min) | μ | ESOD ± SD (%) | | ESOD ± SD (%) | | RMSE ± SD (mg/dl) | |
|---|---|---|---|---|---|---|---|
| | | CGM SERIES | | POL PREDICTION | | | |
| 20 | 0.5 | | | 2515.56 | 550.52 | 24.63 | 5.20 |
| | 0.75 | | | 1930.45 | 428.72 | 28.43 | 5.38 |
| | 0.9 | | | 1785.97 | 425.83 | 35.72 | 6.35 |
| 30 | 0.5 | 2066.80 | 498.50 | 2822.16 | 601.07 | 34.99 | 6.87 |
| | 0.75 | | | 2004.86 | 434.05 | 37.30 | 6.83 |
| | 0.9 | | | 1806.30 | 427.26 | 42.49 | 7.41 |
| 40 | 0.5 | | | 3163.23 | 661.31 | 44.71 | 8.25 |
| | 0.75 | | | 2094.76 | 441.83 | 45.43 | 8.02 |
| | 0.9 | | | 1832.30 | 428.99 | 48.61 | 8.39 |
| | | CGM SERIES | | AR PREDICTION | | | |
| 20 | 0.5 | | | 4101.81 | 944.99 | 25.77 | 5.87 |
| | 0.75 | | | 2990.30 | 644.75 | 25.46 | 5.50 |
| | 0.9 | | | 2396.43 | 521.59 | 24.92 | 5.19 |
| 30 | 0.5 | 2066.80 | 498.50 | 5011.10 | 1150.82 | 38.79 | 8.47 |
| | 0.75 | | | 3462.34 | 729.12 | 37.16 | 7.72 |
| | 0.9 | | | 2573.82 | 542.43 | 34.74 | 6.84 |
| 40 | 0.5 | | | 5837.42 | 1256.08 | 50.70 | 10.23 |
| | 0.75 | | | 3929.29 | 780.29 | 47.94 | 9.42 |
| | 0.9 | | | 2764.77 | 548.99 | 43.67 | 8.11 |
| | | CGM SERIES | | S PREDICTION | | | |
| 20 | | | | 4064.68 | 1107.72 | 23.71 | 5.43 |
| 30 | | 2066.80 | 498.50 | 4811.34 | 1245.62 | 34.97 | 7.22 |
| 40 | | | | 5677.07 | 1345.60 | 45.66 | 8.65 |

FIG. 44

| PH (min) | μ | Delay ± SD (min) | | Gain (min) | Delay ± SD (min) | | Gain (min) | Delay ± SD (min) | | Gain (min) |
|---|---|---|---|---|---|---|---|---|---|---|
| | | POL PREDICTION | | | AR PREDICTION | | | S PREDICTION | | |
| 20 | 0.5 | 13.85 | 2.40 | 6.15 | 16.90 | 2.28 | 3.10 | | | |
| | 0.75 | 5.74 | 1.10 | 14.26 | 14.62 | 2.18 | 5.38 | 17.11 | 2.71 | 2.89 |
| | 0.9 | -9.81 | 3.09 | 29.81 | 10.54 | 1.56 | 9.46 | | | |
| 30 | 0.5 | 16.53 | 1.84 | 13.47 | 21.44 | 2.13 | 8.56 | | | |
| | 0.75 | 7.75 | 2.45 | 22.25 | 16.79 | 2.14 | 13.21 | 21.79 | 2.49 | 8.21 |
| | 0.9 | -7.46 | 3.50 | 37.46 | 11.49 | 1.99 | 18.51 | | | |
| 40 | 0.5 | 19.11 | 2.94 | 20.89 | 23.47 | 3.23 | 16.53 | | | |
| | 0.75 | 9.97 | 2.18 | 30.03 | 19.73 | 2.66 | 20.27 | 23.10 | 3.58 | 16.90 |
| | 0.9 | -6.10 | 2.62 | 46.10 | 12.73 | 2.51 | 27.27 | | | |

FIG. 45

| PH (min) | μ | 95th %ile delay ± SD (min) | 95th %ile gain (min) | 5th %ile delay ± SD (min) | 5th %ile gain (min) | Hypo delay ± SD (min) | Hypo gain (min) |
|---|---|---|---|---|---|---|---|
| | | | POL PREDICTION | | | | |
| 20 | 0.5 | -2.38 | 3.47 | 22.38 | -3.51 | 5.37 | 23.51 | -4.09 | 5.16 | 24.09 |
| 20 | 0.75 | 1.39 | 5.18 | 18.61 | -0.43 | 5.89 | 20.43 | -0.67 | 5.73 | 20.67 |
| 20 | 0.9 | 0.09 | 28.16 | 19.91 | 3.76 | 12.37 | 16.24 | 6.60 | 10.11 | 13.40 |
| 30 | 0.5 | 2.19 | 4.07 | 27.81 | 1.07 | 4.21 | 28.93 | -0.21 | 5.48 | 30.21 |
| 30 | 0.75 | 5.93 | 5.66 | 24.07 | 4.07 | 5.20 | 25.93 | 3.52 | 6.46 | 26.48 |
| 30 | 0.9 | 9.27 | 16.82 | 20.73 | 9.26 | 8.13 | 20.74 | 10.84 | 12.30 | 19.16 |
| 40 | 0.5 | 8.06 | 5.13 | 31.94 | 6.43 | 4.96 | 33.57 | 5.81 | 6.50 | 34.19 |
| 40 | 0.75 | 11.08 | 6.37 | 28.92 | 9.16 | 5.71 | 30.84 | 8.79 | 7.29 | 31.21 |
| 40 | 0.9 | 13.76 | 16.33 | 26.24 | 15.39 | 8.91 | 24.61 | 15.27 | 10.23 | 24.73 |
| | | | AR PREDICTION | | | | |
| 20 | 0.5 | -6.14 | 2.32 | 26.14 | -1.08 | 4.83 | 21.08 | -1.61 | 3.13 | 21.61 |
| 20 | 0.75 | -4.52 | 2.56 | 24.52 | 0.43 | 2.43 | 19.57 | 0.29 | 2.42 | 19.71 |
| 20 | 0.9 | -2.80 | 3.69 | 22.80 | 3.39 | 2.80 | 16.61 | 3.56 | 2.39 | 16.44 |
| 30 | 0.5 | -2.41 | 2.91 | 32.41 | 3.29 | 2.96 | 26.71 | 3.06 | 3.41 | 26.94 |
| 30 | 0.75 | -0.53 | 3.65 | 30.53 | 5.38 | 3.32 | 24.62 | 5.39 | 3.48 | 24.61 |
| 30 | 0.9 | 1.21 | 4.14 | 28.79 | 9.12 | 3.54 | 20.88 | 9.02 | 3.26 | 20.98 |
| 40 | 0.5 | 3.44 | 4.29 | 36.56 | 9.39 | 3.44 | 30.61 | 8.90 | 4.11 | 31.10 |
| 40 | 0.75 | 4.96 | 4.83 | 35.04 | 11.24 | 3.53 | 28.76 | 11.08 | 3.90 | 28.92 |
| 40 | 0.9 | 6.21 | 5.38 | 33.79 | 15.11 | 3.83 | 24.89 | 15.76 | 6.02 | 24.24 |
| | | | S PREDICTION | | | | |
| 20 | | -5.09 | 4.32 | 25.09 | -5.48 | 4.82 | 25.48 | -5.40 | 5.56 | 25.40 |
| 30 | | -0.26 | 6.12 | 30.26 | -0.64 | 4.89 | 30.64 | -1.31 | 6.70 | 31.31 |
| 40 | | 5.96 | 6.26 | 34.04 | 4.72 | 5.92 | 35.28 | 5.65 | 6.93 | 34.35 |

FIG. 46

| PH (min) | μ | # Peak ± sd | | # Nadir ± sd | | # Hypo ± sd | |
|---|---|---|---|---|---|---|---|
| CGM SERIES | | | | | | | |
| | | 83.57 | 28.57 | 126.88 | 42.19 | 139.07 | 72.27 |
| POL PREDICTION | | | | | | | |
| 20 | 0.5 | 156.26 | 61.88 | 219.33 | 91.08 | 225.33 | 108.83 |
| 20 | 0.75 | 137.57 | 53.03 | 198.45 | 75.77 | 204.62 | 95.93 |
| 20 | 0.9 | 95.24 | 32.88 | 146.55 | 46.21 | 152.79 | 67.65 |
| 30 | 0.5 | 199.79 | 80.15 | 267.43 | 112.53 | 270.57 | 127.59 |
| 30 | 0.75 | 163.83 | 64.48 | 227.48 | 89.99 | 230.81 | 104.48 |
| 30 | 0.9 | 105.10 | 37.45 | 161.76 | 51.43 | 164.67 | 71.58 |
| 40 | 0.5 | 246.29 | 98.69 | 312.81 | 132.75 | 316.43 | 143.63 |
| 40 | 0.75 | 189.45 | 73.99 | 254.10 | 99.90 | 255.59 | 112.77 |
| 40 | 0.9 | 115.50 | 41.75 | 174.43 | 57.60 | 176.88 | 74.27 |
| AR PREDICTION | | | | | | | |
| 20 | 0.5 | 184.45 | 77.34 | 199.71 | 80.21 | 209.05 | 104.06 |
| 20 | 0.75 | 170.83 | 69.09 | 187.02 | 73.39 | 195.79 | 96.67 |
| 20 | 0.9 | 144.29 | 55.34 | 163.12 | 60.73 | 172.57 | 85.61 |
| 30 | 0.5 | 260.52 | 11.91 | 239.24 | 104.97 | 245.17 | 121.46 |
| 30 | 0.75 | 228.50 | 93.78 | 214.50 | 90.25 | 222.09 | 109.03 |
| 30 | 0.9 | 175.09 | 68.19 | 179.79 | 69.07 | 186.93 | 90.63 |
| 40 | 0.5 | 330.07 | 136.39 | 274.79 | 123.52 | 280.79 | 137.73 |
| 40 | 0.75 | 279.93 | 114.53 | 241.55 | 105.83 | 247.24 | 119.54 |
| 40 | 0.9 | 204.83 | 78.17 | 195.09 | 77.83 | 201.19 | 97.18 |
| S PREDICTION | | | | | | | |
| 20 | 0.5 | 158.79 | 63.60 | 221.64 | 93.67 | 228.90 | 112.68 |
| 30 | 0.5 | 214.26 | 88.10 | 279.81 | 123.15 | 283.24 | 136.88 |
| 40 | 0.5 | 271.24 | 11.10 | 336.38 | 151.04 | 342.86 | 162.55 |

FIG. 47

| PH (min) | μ | RMSE ± SD (mg/dl) | | MARD ± SD (%) | | MAD ± SD (mg/dl) | |
|---|---|---|---|---|---|---|---|
| | | POL PREDICTION | | | | | |
| 20 | 0.5 | 79.97 | 24.57 | 41.14 | 10.28 | 84.87 | 43.29 |
| | 0.75 | 80.91 | 25.00 | 41.40 | 10.26 | 82.71 | 41.97 |
| | 0.9 | 80.93 | 26.09 | 40.78 | 10.69 | 83.38 | 41.32 |
| 30 | 0.5 | 82.96 | 24.71 | 43.11 | 10.21 | 83.39 | 41.29 |
| | 0.75 | 83.50 | 25.41 | 42.95 | 10.20 | 82.75 | 40.57 |
| | 0.9 | 82.79 | 26.49 | 41.79 | 10.69 | 83.88 | 41.23 |
| 40 | 0.5 | 86.26 | 24.98 | 45.21 | 10.10 | NaN | NaN |
| | 0.75 | 86.37 | 26.05 | 44.53 | 10.05 | NaN | NaN |
| | 0.9 | 84.80 | 27.01 | 42.82 | 10.82 | NaN | NaN |
| | | AR PREDICTION | | | | | |
| 20 | 0.5 | 80.25 | 24.48 | 41.44 | 10.36 | 88.95 | 46.34 |
| | 0.75 | 80.49 | 24.70 | 41.40 | 10.42 | 87.28 | 45.91 |
| | 0.9 | 80.22 | 25.01 | 40.85 | 10.45 | 84.98 | 43.86 |
| 30 | 0.5 | 84.58 | 24.94 | 43.98 | 10.35 | 89.87 | 47.10 |
| | 0.75 | 84.33 | 25.19 | 43.58 | 10.31 | 87.37 | 46.09 |
| | 0.9 | 83.21 | 25.61 | 42.32 | 10.33 | 85.49 | 43.19 |
| 40 | 0.5 | 89.30 | 24.69 | 46.94 | 10.35 | NaN | NaN |
| | 0.75 | 88.47 | 25.47 | 45.96 | 10.07 | NaN | NaN |
| | 0.9 | 86.32 | 26.16 | 43.82 | 10.07 | NaN | NaN |
| | | S PREDICTION | | | | | |
| 20 | | 79.56 | 24.33 | 40.93 | 10.15 | 85.90 | 44.29 |
| 30 | | 82.92 | 24.49 | 43.08 | 10.26 | NaN | NaN |
| 40 | | 86.31 | 24.26 | 45.65 | 10.33 | NaN | NaN |

FIG. 48

| POL prediction ROC (mg/dl/min) | | YSI ROC (mg/dl/min) | | | | | Total |
|---|---|---|---|---|---|---|---|
| | | <-2 | [-2,-1) | [-1,1] | (1,2] | >2 | |
| <-2 | Count | 4 | 11 | 118 | 26 | 4 | 163 |
| | % within YSI | 3.9% | 1.6% | 1.3% | 2.7% | 2.5% | |
| [-2,-1) | Count | 4 | 100 | 609 | 69 | 10 | 792 |
| | % within YSI | 3.9% | 14.2% | 6.9% | 7.2% | 6.1% | |
| [-1,1] | Count | 80 | 519 | 7269 | 741 | 128 | 8737 |
| | % within YSI | 78.4% | 73.6% | 82.7% | 76.9% | 78.5% | |
| (1,2] | Count | 10 | 61 | 652 | 104 | 13 | 840 |
| | % within YSI | 9.8% | 8.7% | 7.4% | 10.8% | 8.0% | |
| >2 | Count | 4 | 14 | 139 | 24 | 8 | 189 |
| | % within YSI | 3.9% | 2.0% | 1.6% | 2.5% | 4.9% | |
| Total | Count | 102 | 705 | 8787 | 964 | 163 | 10721 |

FIG. 49

| AR prediction ROC (mg/dl/min) | | YSI ROC (mg/dl/min) | | | | | Total |
|---|---|---|---|---|---|---|---|
| | | <-2 | [-2,-1) | [-1,1] | (1,2] | >2 | |
| <-2 | Count | 4 | 38 | 214 | 35 | 12 | 303 |
| | % within YSI | 3.9% | 5.4% | 2.4% | 3.6% | 7.3% | |
| [-2,-1) | Count | 10 | 103 | 773 | 87 | 11 | 984 |
| | % within YSI | 9.8% | 14.6% | 8.8% | 9.0% | 6.7% | |
| [-1,1] | Count | 75 | 459 | 6816 | 687 | 108 | 8145 |
| | % within YSI | 73.5% | 65.1% | 77.5% | 71.2% | 65.9% | |
| (1,2] | Count | 7 | 64 | 666 | 107 | 12 | 856 |
| | % within YSI | 6.9% | 9.1% | 7.6% | 11.1% | 7.3% | |
| >2 | Count | 6 | 41 | 322 | 49 | 21 | 439 |
| | % within YSI | 5.9% | 5.8% | 3.7% | 5.1% | 12.8% | |
| Total | Count | 102 | 705 | 8791 | 965 | 164 | 10727 |

FIG. 50

| S prediction ROC (mg/dl/min) | | YSI ROC (mg/dl/min) | | | | | Total |
|---|---|---|---|---|---|---|---|
| | | <-2 | [-2,-1] | [-1,1] | (1,2] | >2 | |
| <-2 | Count | 8 | 58 | 359 | 50 | 10 | 485 |
| | % within YSI | 7.8% | 8.2% | 4.1% | 5.2% | 6.1% | |
| [-2,-1] | Count | 10 | 104 | 829 | 92 | 17 | 1052 |
| | % within YSI | 9.8% | 14.8% | 9.4% | 9.5% | 10.4% | |
| [-1,1] | Count | 70 | 418 | 6413 | 630 | 99 | 7630 |
| | % within YSI | 68.6% | 59.4% | 73.0% | 65.4% | 60.7% | |
| (1,2] | Count | 9 | 73 | 791 | 131 | 14 | 1018 |
| | % within YSI | 8.8% | 10.4% | 9.0% | 13.6% | 8.6% | |
| >2 | Count | 5 | 51 | 391 | 61 | 23 | 531 |
| | % within YSI | 4.9% | 7.2% | 4.5% | 6.3% | 14.1% | |
| Total | Count | 102 | 704 | 8783 | 964 | 163 | 10716 |

FIG. 54

| PH (min) | μ | ESOD ± SD (%) | | ESOD ± SD (%) | | RMSE ± SD (mg/dl) | |
|---|---|---|---|---|---|---|---|
| | | CGM SERIES | | POL PREDICTION | | | |
| 20 | 0.5 | | | 1555.20 | 381.22 | 23.20 | 4.55 |
| | 0.75 | | | 841.12 | 262.36 | 27.10 | 5.14 |
| | 0.9 | | | 584.12 | 282.20 | 34.46 | 6.25 |
| 30 | 0.5 | 1095.11 | 369.30 | 1892.84 | 445.51 | 33.60 | 6.35 |
| | 0.75 | | | 933.54 | 264.98 | 36.03 | 6.64 |
| | 0.9 | | | 598.84 | 280.06 | 41.28 | 7.40 |
| 40 | 0.5 | | | 2221.46 | 511.54 | 43.44 | 8.10 |
| | 0.75 | | | 1032.91 | 278.35 | 44.26 | 8.15 |
| | 0.9 | | | 616.41 | 280.43 | 47.46 | 8.64 |
| | | CGM SERIES | | AR PREDICTION | | | |
| 20 | 0.5 | | | 3090.70 | 780.52 | 24.02 | 5.24 |
| | 0.75 | | | 2046.68 | 510.59 | 23.85 | 5.06 |
| | 0.9 | | | 1439.37 | 380.53 | 23.43 | 4.79 |
| 30 | 0.5 | 1095.11 | 369.30 | 3955.31 | 969.67 | 37.21 | 7.98 |
| | 0.75 | | | 2540.09 | 612.53 | 35.75 | 7.43 |
| | 0.9 | | | 1631.37 | 409.04 | 33.41 | 6.56 |
| 40 | 0.5 | | | 4714.07 | 1148.06 | 49.58 | 10.19 |
| | 0.75 | | | 3012.27 | 719.95 | 46.92 | 9.51 |
| | 0.9 | | | 1824.27 | 439.17 | 42.60 | 8.29 |
| | | CGM SERIES | | S PREDICTION | | | |
| 20 | | | | 2933.16 | 808.28 | 22.19 | 4.42 |
| 30 | | 1095.11 | 369.30 | 3748.25 | 983.11 | 33.41 | 6.37 |
| 40 | | | | 4511.09 | 1145.10 | 44.19 | 8.20 |

FIG. 55

| PH (min) | μ | Delay ± SD (min) | | Gain (min) | Delay ± SD (min) | | Gain (min) | Delay ± SD (min) | | Gain (min) |
|---|---|---|---|---|---|---|---|---|---|---|
| | | POL PREDICTION | | | AR PREDICTION | | | S PREDICTION | | |
| 20 | 0.5 | 14.99 | 2.27 | 5.01 | 17.30 | 2.31 | 2.70 | | | |
| | 0.75 | 6.15 | 1.64 | 13.85 | 15.33 | 1.57 | 4.67 | 17.32 | 2.72 | 2.68 |
| | 0.9 | -10.42 | 2.88 | 30.42 | 10.90 | 1.272 | 9.10 | | | |
| 30 | 0.5 | 16.91 | 1.95 | 13.09 | 21.69 | 2.041 | 8.31 | | | |
| | 0.75 | 8.45 | 2.56 | 21.55 | 17.30 | 2.33 | 12.70 | 22.08 | 2.63 | 7.93 |
| | 0.9 | -8.49 | 3.65 | 38.49 | 11.93 | 2.27 | 18.07 | | | |
| 40 | 0.5 | 19.77 | 3.13 | 20.23 | 24.02 | 3.176 | 15.98 | | | |
| | 0.75 | 10.58 | 2.47 | 29.42 | 20.14 | 2.93 | 19.86 | 23.76 | 3.88 | 16.24 |
| | 0.9 | -6.78 | 3.82 | 46.78 | 13.47 | 2.77 | 26.53 | | | |

FIG. 56

| PH (min) | μ | 95th %ile delay ± SD (min) | 95th %ile gain (min) | 5th %ile delay ± SD (min) | 5th %ile gain (min) | Hypo delay ± SD (min) | Hypo gain (min) |
|---|---|---|---|---|---|---|---|
| | | | | POL PREDICTION | | | |
| 20 | 0.5 | -2.46 | 2.40 | 22.46 | -2.99 | 3.66 | 22.99 | -3.35 | 3.18 | 23.35 |
| 20 | 0.75 | 0.95 | 3.41 | 19.05 | 0.27 | 4.49 | 19.73 | -0.02 | 4.71 | 20.02 |
| 20 | 0.9 | -1.56 | 21.27 | 21.56 | 4.44 | 14.85 | 15.56 | 5.18 | 17.82 | 14.82 |
| 30 | 0.5 | 1.69 | 3.67 | 28.31 | 0.72 | 3.40 | 29.28 | 0.26 | 4.26 | 29.74 |
| 30 | 0.75 | 5.50 | 4.38 | 24.50 | 4.11 | 4.52 | 25.89 | 3.97 | 5.71 | 26.03 |
| 30 | 0.9 | 6.35 | 13.59 | 23.65 | 9.33 | 11.17 | 20.66 | 9.97 | 11.06 | 20.03 |
| 40 | 0.5 | 7.26 | 4.20 | 32.74 | 5.99 | 5.09 | 34.01 | 5.793 | 5.79 | 34.21 |
| 40 | 0.75 | 11.29 | 5.64 | 28.72 | 9.04 | 5.34 | 30.96 | 9.490 | 6.49 | 30.51 |
| 40 | 0.9 | 11.77 | 12.88 | 28.23 | 14.97 | 9.99 | 25.03 | 16.49 | 11.42 | 23.51 |
| | | | | AR PREDICTION | | | |
| 20 | 0.5 | -6.71 | 2.38 | 26.72 | -0.93 | 4.45 | 20.94 | -1.30 | 3.49 | 21.30 |
| 20 | 0.75 | -5.21 | 2.64 | 25.21 | 0.35 | 2.57 | 19.65 | 0.37 | 2.41 | 19.63 |
| 20 | 0.9 | -3.57 | 3.99 | 23.57 | 3.30 | 3.07 | 16.70 | 3.16 | 2.44 | 16.84 |
| 30 | 0.5 | -3.22 | 4.09 | 33.22 | 3.23 | 2.84 | 26.77 | 2.94 | 2.75 | 27.06 |
| 30 | 0.75 | -1.52 | 4.21 | 31.52 | 4.91 | 3.05 | 25.09 | 4.91 | 3.46 | 25.09 |
| 30 | 0.9 | -0.25 | 5.35 | 30.25 | 8.73 | 3.99 | 21.27 | 8.91 | 3.16 | 21.09 |
| 40 | 0.5 | 2.10 | 5.55 | 37.90 | 9.04 | 3.77 | 30.96 | 8.96 | 3.55 | 31.31 |
| 40 | 0.75 | 3.30 | 5.45 | 36.70 | 10.62 | 3.36 | 29.38 | 10.51 | 3.91 | 29.49 |
| 40 | 0.9 | 5.04 | 6.65 | 34.95 | 14.36 | 4.45 | 25.64 | 14.65 | 3.95 | 25.35 |
| | | | | S PREDICTION | | | |
| 20 | | -4.50 | 2.47 | 24.50 | -4.34 | 3.62 | 24.34 | -4.49 | 2.68 | 24.49 |
| 30 | | -0.73 | 4.47 | 30.73 | -0.99 | 3.50 | 30.99 | -1.02 | 3.88 | 31.02 |
| 40 | | 5.5.22 | 5.38 | 34.78 | 4.57 | 4.90 | 35.43 | 4.75 | 4.67 | 35.25 |

FIG. 57

| PH (min) | μ | # Peak ± sd | | # Nadir ± sd | | # Hypo ± sd | |
|---|---|---|---|---|---|---|---|
| | | CGM SERIES | | | | | |
| | | 78.19 | 33.68 | 120.43 | 48.38 | 128.74 | 72.34 |
| | | POL PREDICTION | | | | | |
| 20 | 0.5 | 143.26 | 68.02 | 206.43 | 96.81 | 207 | 109.06 |
| 20 | 0.75 | 127.45 | 58.93 | 187.48 | 81.33 | 188.88 | 96.61 |
| 20 | 0.9 | 86.98 | 35.85 | 135.50 | 51.17 | 141.83 | 69.79 |
| 30 | 0.5 | 185 | 90.25 | 249.21 | 119.86 | 248.26 | 125.22 |
| 30 | 0.75 | 153.02 | 70.66 | 213.26 | 94.30 | 213.79 | 103.97 |
| 30 | 0.9 | 96.86 | 40.13 | 148.74 | 56.07 | 152.55 | 72.54 |
| 40 | 0.5 | 228.38 | 109.25 | 292.86 | 141.77 | 291.29 | 143.48 |
| 40 | 0.75 | 177.93 | 81.50 | 239.62 | 107.16 | 237.52 | 113.70 |
| 40 | 0.9 | 106.76 | 45.63 | 161.21 | 62.39 | 162.88 | 75.98 |
| | | AR PREDICTION | | | | | |
| 20 | 0.5 | 167.95 | 85.25 | 187.91 | 89.15 | 190.86 | 102.50 |
| 20 | 0.75 | 156.91 | 77.84 | 177.12 | 80.72 | 179.59 | 95.70 |
| 20 | 0.9 | 132.33 | 61.93 | 153.69 | 66.75 | 159.26 | 85.47 |
| 30 | 0.5 | 239.14 | 116.82 | 224.33 | 112.06 | 224.02 | 119.24 |
| 30 | 0.75 | 210 | 100.37 | 203.26 | 98.49 | 203.69 | 107.78 |
| 30 | 0.9 | 163.02 | 73.35 | 169.69 | 75.97 | 173.38 | 91.22 |
| 40 | 0.5 | 307.33 | 146.15 | 258.41 | 131.45 | 257.17 | 135.88 |
| 40 | 0.75 | 262.48 | 123.02 | 227.86 | 113.15 | 227.64 | 118.21 |
| 40 | 0.9 | 193.09 | 86.43 | 184.36 | 85.09 | 186.14 | 96.59 |
| | | S PREDICTION | | | | | |
| 20 | 0.5 | 144.02 | 69.75 | 206.45 | 101.14 | 207.91 | 112.41 |
| 30 | 0.5 | 196.88 | 97.42 | 259.69 | 129.46 | 259.33 | 135.98 |
| 40 | 0.5 | 250.98 | 121.59 | 314.38 | 159.71 | 311.74 | 160.37 |

FIG. 58

| PH (min) | μ | RMSE ± SD (mg/dl) | | MARD ± SD (%) | | MAD ± SD (mg/dl) | |
|---|---|---|---|---|---|---|---|
| | | \multicolumn{6}{c}{POL PREDICTION} | | | | | |
| 20 | 0.5 | 78.01 | 26.39 | 40.34 | 12.38 | 84.76 | 40.48 |
| | 0.75 | 78.95 | 26.65 | 40.68 | 12.43 | 85.77 | 41.94 |
| | 0.9 | 79.58 | 28.19 | 40.56 | 12.57 | 87.81 | 42.41 |
| 30 | 0.5 | 80.89 | 25.95 | 42.33 | 12.49 | 86.45 | 41.04 |
| | 0.75 | 81.64 | 26.62 | 42.27 | 12.24 | 87.52 | 44.50 |
| | 0.9 | 81.53 | 28.59 | 41.83 | 12.56 | 89.13 | 43.61 |
| 40 | 0.5 | 84.14 | 25.31 | 44.29 | 11.68 | 88.51 | 44.67 |
| | 0.75 | 84.57 | 26.65 | 43.99 | 11.62 | 89.63 | 47.49 |
| | 0.9 | 83.60 | 29.11 | 43.15 | 12.54 | 89.88 | 44.78 |
| | | \multicolumn{6}{c}{AR PREDICTION} | | | | | |
| 20 | 0.5 | 81.21 | 23.59 | 40.64 | 12.37 | 86.40 | 40.42 |
| | 0.75 | 81.27 | 23.81 | 40.61 | 12.55 | 86.59 | 40.81 |
| | 0.9 | 80.67 | 24.35 | 40.15 | 12.75 | 86.79 | 42.03 |
| 30 | 0.5 | 86.34 | 22.40 | 43.25 | 12.42 | 90.06 | 40.73 |
| | 0.75 | 85.59 | 22.97 | 42.95 | 12.56 | 89.14 | 41.94 |
| | 0.9 | 83.62 | 24.25 | 41.79 | 12.89 | 89.00 | 44.36 |
| 40 | 0.5 | 91.87 | 21.10 | 46.16 | 12.04 | 93.62 | 43.95 |
| | 0.75 | 90.07 | 22.18 | 45.21 | 12.09 | 92.28 | 46.12 |
| | 0.9 | 86.89 | 23.92 | 43.46 | 12.32 | 92.15 | 49.17 |
| | | \multicolumn{6}{c}{S PREDICTION} | | | | | |
| 20 | | 80.41 | 23.44 | 40.06 | 11.95 | 85.09 | 40.62 |
| 30 | | 84.12 | 22.97 | 42.30 | 12.20 | 86.76 | 40.71 |
| 40 | | 88.51 | 22.13 | 44.65 | 11.90 | 88.91 | 42.94 |

FIG. 59

| POL prediction ROC (mg/dl/min) | | YSI ROC (mg/dl/min) | | | | | Total |
|---|---|---|---|---|---|---|---|
| | | <-2 | [-2,-1] | [-1,1] | (1,2] | >2 | |
| <-2 | Count | 7 | 28 | 115 | 16 | 7 | 173 |
| | % within YSI | 4.1% | 3.4% | 1.3% | 1.5% | 2.1% | |
| [-2,-1] | Count | 10 | 102 | 666 | 93 | 30 | 901 |
| | % within YSI | 5.8% | 12.4% | 7.5% | 8.5% | 9.0% | |
| [-1,1] | Count | 133 | 618 | 7296 | 850 | 251 | 9148 |
| | % within YSI | 77.3% | 74.9% | 82.3% | 77.9% | 75.1% | |
| (1,2] | Count | 18 | 57 | 654 | 107 | 34 | 870 |
| | % within YSI | 10.5% | 6.9% | 7.4% | 9.8% | 10.2% | |
| >2 | Count | 4 | 20 | 132 | 25 | 12 | 193 |
| | % within YSI | 2.3% | 2.4% | 1.5% | 2.3% | 3.6% | |
| Total | Count | 172 | 825 | 8863 | 1091 | 334 | 11285 |

FIG. 60

| AR prediction ROC (mg/dl/min) | | YSI ROC (mg/dl/min) | | | | | Total |
|---|---|---|---|---|---|---|---|
| | | <-2 | [-2,-1] | [-1,1] | (1,2] | >2 | |
| <-2 | Count | 15 | 43 | 228 | 22 | 17 | 325 |
| | % within YSI | 8.7% | 5.2% | 2.6% | 2.0% | 5.1% | |
| [-2,-1] | Count | 14 | 102 | 787 | 100 | 39 | 1042 |
| | % within YSI | 8.1% | 12.4% | 8.9% | 9.2% | 11.7% | |
| [-1,1] | Count | 111 | 581 | 6827 | 807 | 224 | 8550 |
| | % within YSI | 64.5% | 70.4% | 77.0% | 74.0% | 67.1% | |
| (1,2] | Count | 21 | 58 | 670 | 101 | 34 | 884 |
| | % within YSI | 12.2% | 7.0% | 7.6% | 9.3% | 10.2% | |
| >2 | Count | 11 | 41 | 353 | 61 | 20 | 486 |
| | % within YSI | 6.4% | 5.0% | 4.0% | 5.6% | 6.0% | |
| Total | Count | 172 | 825 | 8865 | 1091 | 334 | 11287 |

FIG. 61

| S prediction ROC (mg/dl/min) | | YSI ROC (mg/dl/min) | | | | | Total |
|---|---|---|---|---|---|---|---|
| | | <-2 | [-2,-1) | [-1,1] | (1,2] | >2 | |
| <-2 | Count | 16 | 50 | 380 | 43 | 29 | 518 |
| | % within YSI | 9.3% | 6.1% | 4.3% | 3.9% | 8.7% | |
| [-2,-1) | Count | 23 | 108 | 873 | 113 | 39 | 1156 |
| | % within YSI | 13.4% | 13.1% | 9.8% | 10.4% | 11.7% | |
| [-1,1] | Count | 100 | 533 | 6350 | 752 | 195 | 7930 |
| | % within YSI | 58.1% | 64.6% | 71.6% | 68.9% | 58.4% | |
| (1,2] | Count | 19 | 82 | 793 | 112 | 44 | 1050 |
| | % within YSI | 11.0% | 9.9% | 8.9% | 10.3% | 13.2% | |
| >2 | Count | 14 | 52 | 467 | 71 | 27 | 631 |
| | % within YSI | 8.1% | 6.3% | 5.3% | 6.5% | 8.1% | |
| Total | Count | 172 | 825 | 8863 | 1091 | 334 | 11285 |

FIG. 62

| Variable | Measure | Cohort (n=44) |
|---|---|---|
| Age | [years] (SD) | 38 (11.7) |
| Sex, male | [n] (%) | 26 (59) |
| Body mass index > 25 kg/m² | [n] (%) | 27 (61) |
| Diabetes duration | [years] (SD) | 22.7 (13.6) |
| HbA1c | [years] (SD) | 62 (12) |
|  | [%] (SD) | 7.8 (1.0) |
| Insulin pump - use | [n] (%) | 13 (29.5) |
| CGM use before study | [n] (%) | 23 (52.3) |

FIG. 63

| Age | ≥ 18 years of age |
|---|---|
| Diagnosis | DM, MDI or insulin pump therapy |
| Able to comply with procedures | Understand study procedure and risks, willing to comply with protocol requirements |
| Medical Conditions | • Severe hypoglycemia, past 6 months<br>• Ketoacidosis, past 6 months<br>• Known microvascular complications<br>• Requiring MRI<br>• Chronic infection (with AB use) |
| Concomitant meds | • Chemotherapy for any form of cancer<br>• Immunosuppressant therapy<br>• Chronic systemic glucocorticoids<br>• Anti-coagulant therapy |

FIG. 64

| Sensor | Duration (days) | CGM # | CGM Sampling (min) | YSI # | YSI Session # | YSI Sampling (min) | SMBG # |
|---|---|---|---|---|---|---|---|
| 'S23269' | 180 | 50654 | 5 | 359 | 7 | 13 | 650 |
| 'S23814' | 70 | 18854 | 6 | 238 | 3 | 15 | 423 |
| 'S23852' | 94 | 25546 | 5 | 361 | 4 | 15 | 665 |
| 'S23943' | 68 | 19587 | 5 | 251 | 3 | 15 | 387 |
| 'S8493' | 121 | 32633 | 5 | 374 | 5 | 15 | 663 |
| 'S8502' | 141 | 26838 | 8 | 331 | 5 | 15 | 591 |
| 'S8510' | 121 | 33310 | 5 | 360 | 5 | 15 | 420 |
| 'S8513' | 121 | 34210 | 5 | 355 | 5 | 9 | 660 |
| 'S8523' | 132 | 33716 | 5 | 325 | 5 | 16 | 405 |
| 'S8525' | 115 | 25850 | 6 | 254 | 5 | 15 | 485 |
| 'S8526' | 119 | 26033 | 7 | 332 | 5 | 15 | 667 |
| 'S8527' | 121 | 34811 | 5 | 354 | 5 | 14 | 823 |
| 'S8529' | 121 | 33327 | 5 | 376 | 5 | 15 | 427 |
| 'S8530' | 113 | 32418 | 5 | 339 | 5 | 10 | 986 |
| 'S8583' | 121 | 34016 | 5 | 360 | 5 | 10 | 728 |
| 'S8584' | 128 | 34806 | 5 | 214 | 5 | 14 | 904 |
| 'S8589' | 90 | 25961 | 5 | 258 | 4 | 30 | 649 |
| 'S8603' | 113 | 30588 | 5 | 316 | 4 | 30 | 965 |
| 'S8609' | 121 | 34168 | 5 | 310 | 5 | 15 | 427 |
| 'S8610' | 121 | 34865 | 5 | 364 | 5 | 15 | 370 |
| 'S8614' | 90 | 26321 | 5 | 275 | 4 | 15 | 406 |
| 'S8616' | 89 | 25570 | 5 | 270 | 4 | 15 | 328 |
| 'S8621' | 121 | 33847 | 5 | 373 | 5 | 15 | 830 |
| 'S8623' | 111 | 31612 | 5 | 287 | 4 | 15 | 354 |
| 'S8624' | 121 | 31260 | 6 | 349 | 5 | 15 | 807 |
| 'S8657' | 89 | 24031 | 5 | 277 | 4 | 15 | 594 |
| 'S8668' | 100 | 28628 | 5 | 286 | 4 | 12 | 562 |
| 'S8671' | 73 | 21031 | 5 | 344 | 3 | 15 | 764 |
| 'S8675' | 51 | 10340 | 7 | 393 | 5 | 15 | 596 |
| 'S8684' | 86 | 21387 | 6 | 218 | 3 | 15 | 391 |
| 'S8686' | 73 | 23074 | 5 | 250 | 3 | 15 | 387 |
| 'S8688' | 110 | 30593 | 5 | 364 | 5 | 15 | 425 |
| 'S8690' | 90 | 25768 | 5 | 277 | 4 | 16 | 409 |
| 'S8693' | 90 | 24882 | 5 | 279 | 4 | 15 | 543 |
| 'S8694' | 91 | 25103 | 5 | 223 | 3 | 15 | 296 |
| 'S8697' | 120 | 33219 | 5 | 321 | 5 | 14 | 648 |
| 'S8703' | 90 | 24386 | 5 | 291 | 4 | 15 | 501 |
| 'S8870' | 106 | 28119 | 5 | 278 | 4 | 15 | 285 |
| 'S8897' | 66 | 18022 | 5 | 238 | 3 | 15 | 479 |
| 'S8949' | 93 | 25430 | 5 | 251 | 4 | 10 | 721 |
| 'S8952' | 88 | 25749 | 5 | 281 | 4 | 15 | 318 |
| 'S8962' | 92 | 19105 | 7 | 279 | 4 | 17 | 278 |

FIG. 65

| Sensor | Duration (days) | CGM # | CGM Sampling (min) | YSI # | YSI Session # | YSI Sampling (min) | SMBG # |
|---|---|---|---|---|---|---|---|
| 'S23269' | 180 | 50688 | 5 | 400 | 7 | 13 | 662 |
| 'S23814' | 71 | 16887 | 6 | 245 | 3 | 15 | 433 |
| 'S23853' | 94 | 25546 | 5 | 278 | 4 | 15 | 674 |
| 'S23943' | 69 | 19771 | 5 | 257 | 3 | 15 | 387 |
| 'S8493' | 121 | 32633 | 5 | 392 | 5 | 15 | 666 |
| 'S8502' | 141 | 26838 | 8 | 366 | 5 | 15 | 604 |
| 'S8510' | 121 | 32310 | 5 | 379 | 5 | 15 | 422 |
| 'S8513' | 121 | 34310 | 5 | 372 | 5 | 9 | 671 |
| 'S8523' | 122 | 33716 | 5 | 373 | 5 | 16 | 437 |
| 'S8525' | 115 | 25850 | 6 | 333 | 5 | 15 | 498 |
| 'S8526' | 119 | 26023 | 7 | 379 | 5 | 15 | 675 |
| 'S8527' | 121 | 34811 | 5 | 365 | 5 | 14 | 836 |
| 'S8529' | 121 | 33327 | 5 | 398 | 5 | 15 | 429 |
| 'S8530' | 113 | 32418 | 5 | 360 | 5 | 10 | 1012 |
| 'S8582' | 121 | 34016 | 5 | 393 | 5 | 5 | 980 |
| 'S8584' | 128 | 34806 | 5 | 269 | 5 | 14 | 915 |
| 'S8589' | 90 | 25961 | 5 | 287 | 4 | 15 | 699 |
| 'S8603' | 113 | 30588 | 5 | 374 | 4 | 15 | 980 |
| 'S8609' | 121 | 34168 | 5 | 321 | 5 | 15 | 430 |
| 'S8610' | 121 | 34965 | 5 | 412 | 5 | 15 | 372 |
| 'S8614' | 90 | 26321 | 5 | 322 | 4 | 15 | 408 |
| 'S8616' | 89 | 25570 | 5 | 277 | 4 | 15 | 328 |
| 'S8621' | 121 | 32848 | 5 | 399 | 5 | 15 | 876 |
| 'S8623' | 111 | 31636 | 5 | 317 | 4 | 15 | 355 |
| 'S8624' | 121 | 31260 | 6 | 390 | 5 | 15 | 814 |
| 'S8657' | 89 | 24091 | 5 | 287 | 4 | 15 | 599 |
| 'S8668' | 100 | 28639 | 5 | 323 | 4 | 5 | 568 |
| 'S8671' | 79 | 21109 | 5 | 283 | 3 | 15 | 778 |
| 'S8675' | 51 | 10352 | 7 | 331 | 5 | 15 | 637 |
| 'S8684' | 86 | 21290 | 6 | 237 | 3 | 15 | 403 |
| 'S8686' | 81 | 22138 | 5 | 275 | 3 | 15 | 389 |
| 'S8688' | 110 | 30593 | 5 | 387 | 5 | 15 | 427 |
| 'S8690' | 90 | 25768 | 5 | 278 | 4 | 16 | 420 |
| 'S8693' | 90 | 24882 | 5 | 292 | 4 | 15 | 571 |
| 'S8694' | 92 | 25521 | 5 | 262 | 3 | 15 | 228 |
| 'S8697' | 130 | 33219 | 5 | 342 | 5 | 14 | 663 |
| 'S8703' | 90 | 24386 | 5 | 310 | 4 | 15 | 505 |
| 'S8870' | 90 | 23663 | 5 | 286 | 4 | 15 | 286 |
| 'S8897' | 66 | 18023 | 5 | 278 | 3 | 15 | 485 |
| 'S8949' | 93 | 25420 | 5 | 300 | 4 | 10 | 748 |
| 'S8952' | 88 | 25749 | 5 | 399 | 4 | 15 | 321 |
| 'S8962' | 92 | 19105 | 7 | 305 | 4 | 5 | 284 |

REAL-TIME DENOISING AND PREDICTION FOR A CONTINUOUS GLUCOSE MONITORING SYSTEM

CROSS-REFERENCE TO RELATED APPLICATION

This application claims the benefit of priority to U.S. Provisional Application Ser. No. 62/329,760, filed on Apr. 29, 2016, which is incorporated herein by reference in its entirety.

BACKGROUND

Field of Invention

The present invention relates generally to determining a concentration of analyte in a medium (e.g., interstitial fluid) of a living animal using a sensor implanted (partially or completely) in the living animal. Specifically, the present invention relates to real-time denoising a raw signal including an analyte-modulated component and converting the processed signal to an analyte concentration.

Discussion of the Background

Diabetes is a chronic disease that affects about 300 million people in the world. Diabetes therapy is mainly based on insulin, diet, drug administration, and physical exercise, tuned according to Self-Monitoring of Blood Glucose (SMBG) values collected three to four times a day. However, the metabolic control based on SMBG is usually suboptimal, and glucose concentration often exceeds the normal range thresholds (70-180 mg/dl). In the past few years, the achievement of a more accurate control seems possible due to the development of Continuous Glucose Monitoring (CGM) devices. These devices allow measuring glucose concentration for several days in a quasi-time-continuous manner, e.g., every minute, every five minutes, or every ten minutes.

The performance of modern CGM sensors is still considered, however, inferior to that of SMBG measurements and laboratory systems. This is critical both for daily life therapy and in research clinical trials: CGM sensors are not approved to be used in place of SMBG for therapy adjustment and the suboptimal performance of CGM could negatively influence the correct functioning of applications based on it. In particular, three issues of relevance can be pointed out. First, the presence of random noise makes CGM data uncertain. Second, when comparing CGM with "gold standard" blood glucose references measured by laboratory instruments, delays, caused by blood-to-interstitium glucose transport and sensor processing time, and systematic underestimations/overestimations due to calibration problems are visible. Third, generating alerts some time before the CGM profile crosses hypoglycemic/hyperglycemic thresholds may help the mitigation of hypoglycemic/hyperglycemic critical events. Thus, there is presently a need in the art for an improved analyte monitoring systems.

SUMMARY

The present invention overcomes the disadvantages of prior systems by (i) denoising raw signals using a real-time filtering technique and/or (ii) providing a more accurate and/or reliable predictions of analyte concentration. Further variations encompassed within the systems and methods are described in the detailed description of the invention below.

One aspect of the present invention may provide an analyte monitoring system including an analyte sensor and a transmitter. The analyte sensor may include an indicator element that exhibits one or more detectable properties based on an amount or concentration of an analyte in proximity to the indicator element. The analyte sensor may be configured to generate one or more raw signals indicative of one or more analyte amounts or concentrations. The transmitter may be configured to (i) receive from the analyte sensor one or more raw signals indicative of analyte concentration and (ii) denoise the raw signal using a real-time filtering technique with one or more time-varying parameters.

In some embodiments, the real-time filtering technique includes Kalman filtering. In some embodiments, the real-time filtering technique compensates for the presence of one or more missing values in the received one or more raw signals.

In some embodiments, the real-time filtering technique may include estimating the one or more time-varying parameters. In some embodiments, the one or more time-varying parameters may include an error variance $\sigma$. In some embodiments, the one or more time-varying parameters may include a parameter $\lambda^2$, where $\lambda$ represents a degree to which a slope from a current time window is desired to be close to the slope from a previous time window. In some embodiments, the one or more time-varying parameters may be estimated occasionally. In some embodiments, the one or more time-varying parameters may be estimated every 144 minutes using the last 6 hours of data. In some embodiments, the one or more time-varying parameters may be estimated using a stochastically based smoothing criterion that is based on data of a burn-in interval. In some embodiments, the transmitter may be further configured to predict ahead of time an analyte concentration based on one or more of the received one or more raw signals.

Another aspect of the present invention may provide an analyte monitoring system including an analyte sensor and a transmitter. The analyte sensor may include an indicator element that exhibits one or more detectable properties based on an amount or concentration of an analyte in proximity to the indicator element. The analyte sensor may be configured to generate one or more raw signals indicative of one or more analyte amounts or concentrations. The transmitter may be configured to (i) receive from the analyte sensor one or more raw signals indicative of analyte concentration and (ii) predict ahead of time an analyte concentration based on one or more of the received one or more raw signals using one or more prediction models.

In some embodiments, the transmitter may be configured to use a forgetting factor $\mu$ to regulates how the received one or more raw signals are used to predict ahead of time the analyte concentration. In some embodiments, the one or more prediction models may include a first-order polynomial model. In some embodiments, the one or more prediction models may include a first-order autoregressive model. In some embodiments, the one or more prediction models may include Kalman filtering. In some embodiments, the one or more prediction models may include one or more artificial neural networks.

Still another aspect of the invention may provide an analyte monitoring method. The analyte monitoring method may include using an analyte sensor to generate one or more raw signals indicative of one or more analyte amounts or concentrations. The analyte sensor may include an indicator element that exhibits one or more detectable properties based on an amount or concentration of an analyte in proximity to the indicator element. The analyte monitoring method may include using a transmitter to receive from the analyte sensor one or more raw signals indicative of analyte concentration. The analyte monitoring method may include using the transmitter to denoise the raw signal using a real-time filtering technique with one or more time-varying parameters.

Yet another aspect of the invention may provide an analyte monitoring method. The analyte monitoring method may include using an analyte sensor to generate one or more raw signals indicative of one or more analyte amounts or concentrations. The analyte sensor may include an indicator element that exhibits one or more detectable properties based on an amount or concentration of an analyte in proximity to the indicator element. The analyte monitoring method may include using a transmitter to receive from the analyte sensor one or more raw signals indicative of analyte concentration. The analyte monitoring method may include using the transmitter to predict ahead of time an analyte concentration based on one or more of the received one or more raw signals using one or more prediction models.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIG. 18 is a table illustrating ROC accuracy with respect to the concurrence of CGM and hexokinase trends embodying aspects of the present invention.

FIGS. 20A, 20B, and 20C are graphs showing estimated error variance day-by-day (thin line with circles) with sensor's mean (thin line) and global mean error variance (thick line) for three different sensors.

FIGS. 22A-22C are graphs illustrating CGM data (thin line) versus KF series (thick line) for a representative sensor during first, second, and third time periods, respectively.

FIGS. 25A-25C are graphs illustrating KF series with time-varying (thick line), global (thick dashed line) or sensor individualized (thin dashed line) parameters versus CGM data (thin line) for a representative sensor during first, second, and third time windows, respectively.

FIG. 26 is a table illustrating Kalman Filter accuracy metrics.

FIG. 27 is a table illustrating Kalman Filter regularity metrics.

FIG. 28 is a table illustrating ROC accuracy with respect to the concurrence of CGM and YSI trends.

FIG. 29 is a table illustrating ROC accuracy with respect to the concurrence of filtered CGM and YSI trends.

FIGS. 32A-32C are graphs illustrating CGM data (thin line) VS KF series (thick line) for a representative sensor during three different time windows.

FIGS. 33A-33C are graphs illustrating CGM data (thin line) VS KF series (thick line) for a representative sensor during three different time periods.

FIG. 36 is a table showing Kalman Filter accuracy metrics.

FIG. 37 is a table showing Kalman Filter regularity metrics.

FIG. 38 is a table showing ROC accuracy with respect to concurrence of CGM and YSI trends.

FIG. 39 is a table showing ROC accuracy with respect to concurrence of CGM and YSI trends.

FIG. 43 is a table illustrating original versus predicted time-series performance.

FIG. 44 is a table illustrating time delay and gain between original and predicted series, calculated with cross-correlation.

FIG. 45 is a table illustrating time delay and gain between original and predicted series at threshold crossing.

FIG. 46 is a table illustrating number of peaks, nadirs and hypoglycemic events.

FIG. 47 is a table illustrating prediction versus YSI performance at clinical session.

FIG. 48 is a table illustrating ROC accuracy with respect to the concurrence of POL(1) prediction and YSI trends.

FIG. 49 is a table illustrating ROC accuracy with respect to the concurrence of AR(1) prediction and YSI trends.

FIG. 50 is a table illustrating ROC accuracy with respect to the concurrence of S prediction and YSI trends.

FIG. 54 is table showing original VS predicted time-series performance.

FIG. 55 is table showing time delay and gain between original and predicted series, calculated with cross-correlation.

FIG. 56 is table showing time delay and gain between original and predicted series at threshold crossing.

FIG. 57 is table showing a number of peaks, nadirs and hypoglycemic events.

FIG. 58 is table showing prediction versus YSI performance at clinical session.

FIG. 59 is table showing ROC accuracy with respect to the concurrence of POL(1) prediction and YSI trends.

FIG. 60 is table showing ROC accuracy with respect to the concurrence of AR(1) prediction and YSI trends.

FIG. 61 is table showing ROC accuracy with respect to the concurrence of S prediction and YSI trends.

FIG. 62 is a table showing baseline characteristics.

FIG. 63 is a table showing in-exclusive criteria.

FIG. 64 is a table showing PRECISE study Dataset 1 information.

FIG. 65 is a table showing PRECISE study Dataset 2 information.

DETAILED DESCRIPTION OF PREFERRED EMBODIMENTS

Figure 1:
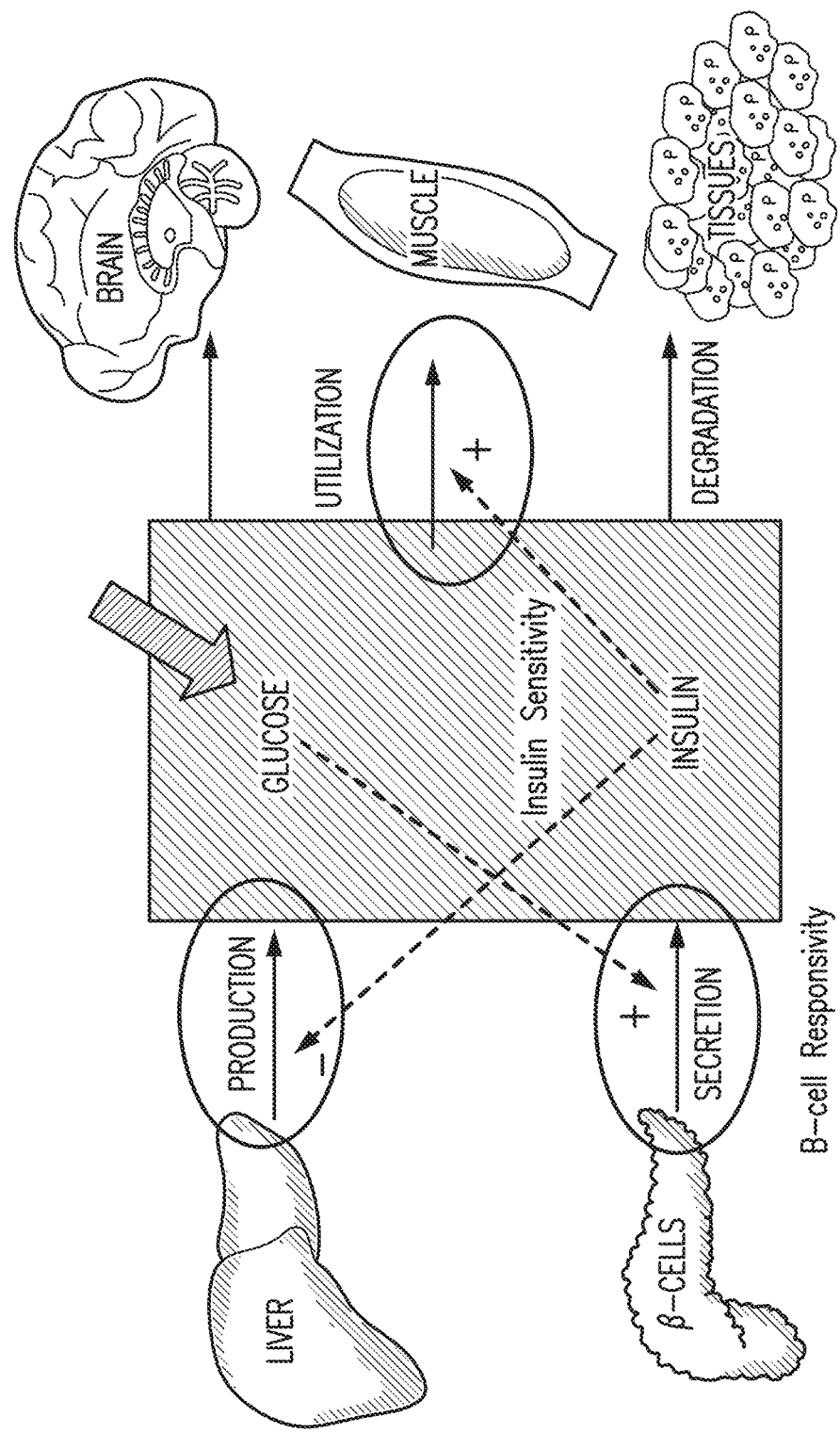
FIG. 1 is a schematic view illustrating a glucose-insulin control system.

The nature of CGM data can open the doors to the realization of investigations and applications that were hindered by the sparseness of SMBG measurements. Retrospective data analysis of CGM readings can be very useful in tuning/refining diabetes therapy. In a real-time perspective, a natural application of CGM devices concerns with the early detection of hypo/hyperglycemic episodes. For instance, by comparing the currently measured (or predicted ahead of time) glucose level with a given hypo/hyper threshold, an alert could be generated. Moreover, CGM sensors are a key element of Artificial Pancreas (AP) research prototypes, i.e., minimally invasive systems for subcutaneous insulin infusion driven by a closed-loop control algorithm. Unfortunately, the performance of alert systems implemented in commercial devices, is still rather poor, with a percentage of false alerts of the order of 50%. Moreover, the currently available transcutaneous CGM systems have short lifespan and require replacement every 5/7 days. Sensor in vivo lifetime may be limited by stability of the enzymes used for glucose recognition, by bio-fouling at the surface of the sensor electrodes, by ongoing inflammatory responses surrounding the sensors as a consequence of the partial implantation (i.e., sensor protrudes through the skin), or by a combination of these effects.

To overcome these limitations, some analyte monitoring systems may include a long-term sensor (e.g., a fully subcutaneously long-term implantable sensor that uses a fluorescent, non-enzymatic (such as bisboronic acid based) glucose indicating hydrogel and a miniaturized optical detection system). In some embodiments, the analyte monitoring system may include use a single sensor for continuous display of accurate analyte values for three months, even up to six months. However, the performance of the analyte monitoring system may still be suboptimal in terms of accuracy and precision.

With the aim to render analyte data more reliable and more accurate, a "smart sensor" architecture concept that consists of an analyte sensor and circuitry configured to perform one or more of denoising, signal enhancement, and prediction has been developed. The present invention has the aim of improving the performance and the accuracy of analyte monitoring systems. The content is organized as follows. Section 1 describes briefly what diabetes is, and how it can be controlled through CGM devices. In Section 2, an analyte monitoring system is widely described, while in Section 3 the database used is presented. In Sections 4 and 5, methods, implementation notes and results of, respectively, denoising and prediction analyses are explained.

1. Diabetes and its Control

1.1 The Glucose-Insulin Regulatory System

The study of glucose metabolism is fundamental both from a physiological point of view, because glucose is the main source of energy for the whole body cells, and from a pathological point of view, because a malfunction of this system would lead to phenomena of glucose intolerance or, in the worst case, to diabetes. The concentration of glucose in healthy subjects is tightly regulated by a complex neuro-hormonal control system. Insulin, which is secreted by the β-cells of the pancreas, is the primary regulator of glucose homeostasis, by promoting its use by tissues and inhibiting its endogenous production. On the other side, hormones such as glucagon, epinephrine, cortisol, and growth hormone play the role, on different time scales, to prevent hypoglycemia. Glucose is generally absorbed by the gastro-intestinal tract through food digestion after a meal or, in fasting condition, it is provided primarily by the liver. Glucose is distributed and used in the whole body. Based on the specific needs and roles in its regulation, tissues and organs can be classified as (i) insulin-independent, (ii) insulin-dependent, and (iii) gluco-sensors. In insulin-independent tissues and organs, such as the central nervous system and erythrocytes, glucose is the substrate of choice and its extraction takes place at a constant speed, regardless of insulin concentration. In insulin-dependent tissues and organs, such as muscle, adipose tissue and liver, the utilization of glucose by these tissues is phasic; in fact, it is modulated by the amount of circulating insulin. Gluco-sensors, such as pancreas β-cells, the liver, and the hypothalamus, are sensitive to glucose concentration and could provide a proper secretory response.

In FIG. 1, a schematic representation of the glucose-insulin control system is shown. In the upper part, the production of glucose, mainly provided by the liver and its utilization, mediated and not by insulin action, is shown. In the lower part, the secretion of insulin from of the β-cells and its degradation by tissues are shown. Dashed arrows show the mutual control between glucose and insulin, where insulin promotes glucose utilization and inhibits its production, while glucose stimulates insulin secretion. In a well-regulated control system, the control system is in closed loop form: glucose stimulates insulin secretion and this, in turn, acts on glucose production and utilization. An imbalance of this feedback control system can lead to diseases such as diabetes.

1.2 Diabetes

Diabetes is a chronic disease characterized by either an autoimmune destruction of pancreas β-cells, leading to insulin deficiency (Type 1 Diabetes Mellitus, T1DM), or by insulin resistance (Type 2 Diabetes Mellitus, T2DM) which may be combined with impaired insulin secretion. As a result, in diabetic subjects the plasma glycemic level exceeds the normal range, with several long- and short-term complications. It is expected that by the year 2030 there may be close to 400 million people with diabetes. At least 50% of the entire diabetic population is unaware of its condition and, in many countries, the portion of the entire diabetic population is unaware of its condition reaches 80%. Every year 3.8 million deaths are caused by complications due to diabetes and, in fact, it is considered currently the fourth leading cause of death worldwide.

1.2.1 Type 1 Diabetes

Type 1 diabetes is the form of diabetes that results from autoimmune destruction of insulin-producing β-cells of the pancreas. The insulin deficiency results in the inability of cells (in particular fat and muscle) to utilize and store glucose, with immediate consequences. These consequences include (i) accumulation of glucose in plasma which leads to strong hyperglycemia, to exceed the threshold of renal reabsorption causing glycosuria, polyuria and polydipsia, and (ii) use of alternative sources of energy such as the lipid reserves, bringing the loss of body fat and protein reserves with loss of lean body mass. Type 1 diabetes is less than 10% of cases of diabetes and it is a disease of childhood thus affecting mostly children and adolescents, more rarely young adults (90%<20 years).

1.2.2 Type 2 Diabetes

Type 2 diabetes is characterized by three physiological abnormalities: impaired insulin secretion, insulin resistance, and overproduction of endogenous glucose. It is the most common type of diabetes (more than 90% of cases), and it is a typically disease of mature age (>40 years), even if it starts to affect patients getting younger. The pathogenesis of type 2 diabetes is caused by a combination of lifestyle (obesity, lack of physical activity, etc.) and genetic factors. This form of diabetes frequently goes undiagnosed for many years because the hyperglycemia develops gradually and at earlier stages it is often not severe enough for the patient to notice any of the classic symptoms of diabetes. Whereas patients with this form of diabetes may have insulin levels that appear normal or elevated, the higher blood glucose levels would be expected to result in even higher insulin values it they had their β-cell function been normal. Thus, insulin secretion is defective in these patients and insufficient to compensate glucose levels due to insulin resistance. Insulin resistance may improve with weight reduction and/or pharmacological treatment of hyperglycemia but is seldom restored to normal.

1.2.3 Complications

All forms of diabetes increase the risk of long-term complications, which are mainly related to damage to blood vessels. In fact, diabetes doubles the risk of cardiovascular disease. The main "macrovascular" diseases (related to atherosclerosis of larger arteries) are ischemic heart disease (angina and myocardial infarction), stroke and peripheral vascular disease. While the main "microvascular" complications (damage to the small blood vessels) are: (i) diabetic retinopathy, (ii) diabetic nephropathy, (iii) and diabetic neuropathy. Diabetic retinopathy (70% T1DM, 40% T2DM) affects blood vessel formation in the retina of the eye, leading to visual symptoms, reduced vision, and potentially blindness. With diabetic nephropathy (20-30% of diabetic patients), the impact of diabetes on the kidneys can lead to scarring changes in the kidney tissue, loss of small or progressively larger amounts of protein in the urine, and eventually chronic kidney disease requiring dialysis. Diabetic neuropathy (20-40% of diabetic patients) is the impact of diabetes on the nervous system, most commonly causing numbness, tingling and pain in the feet and also increasing the risk of skin damage due to altered sensation. Together with vascular disease in the legs, neuropathy contributes to the risk of diabetes-related foot problems (such as diabetic foot ulcers) that can be difficult to treat and occasionally require amputation.

Short-term complications may be caused by either hypoglycemia or hyperglycemia. The first case occurs in people with diabetes treated with insulin or hypoglycemic agents and is more common in people who miss or delay meals after an insulin bolus or do physical activity unexpectedly, causing an increase in glucose utilization by tissues. The second case, diabetic ketoacidosis, occurs usually in young people with type 1 diabetes, and the main cause is the absolute or relative deficiency of insulin. Among the risks are cerebral edema, hyperchloremic acidosis, lactic acidosis, infections, gastric dilation, erosion and thromboembolism. Another complication that affects, however, subjects with type 2 diabetes is the hyperglycemic-hyperosmolar syndrome (mortality 10-60%) characterized by hyperosmolarity (plasma osmolality>320 mosm/kg), severe hyperglycemia (blood glucose>600 mg/dl), marked dehydration, the absence of acidosis.

1.3 Control of Diabetes

For decades, the evaluation of the patient's glycemic control was based solely on glycosuria. Then, with the introduction of self-home capillary blood glucose, a fundamental level of quality was reached. At the end of the 70s, integrated indexes such as HbA1c and glycated proteins were joined. But, until now, the SMBG remained an indispensable element, enabling enormous progress, both in clinical terms, making possible to pass towards a real self-care, and in terms of knowledge, documenting a number of aspects of the physiology and pathophysiology of glucose homeostasis that were previously only intuited.

However, because of the wide and rapid variations in blood glucose due to physical activity, diet, and pharmacological therapy, SMBG values are not sufficient to identify episodes of post-prandial hyperglycemia and especially those of hypoglycemia caused by an overdose of insulin. Since 2000 it has been possible to use techniques for continuous monitoring of blood glucose throughout the day, trying to limit the invasiveness (minimally invasive or non-invasive). In particular, systems have been proposed for Continuous Glucose Monitoring (CGM), which have the advantage of being able to provide almost continuous glucose measurement, essential to recognize critical events in real time.

The standard treatment for patients with diabetes, especially for T1DM, is therefore based on multiple daily injections of insulin (bolus and basal doses), diet and exercise, tuned according to self-monitoring of blood glucose (SMBG) levels 3 to 4 times a day. Thanks to the availability of CGM sensors and insulin delivery systems has been possible to improve the management of diabetes. The SMBG however is still remained fundamental for control therapy due to possible systematic and random errors of CGM sensors, becoming of considerable importance the calibration procedure enabled by SMBG values.

1.3.1 Continuous Glucose Monitoring Systems

The difference between SMBG and CGM is evident: the amount of additional information that can be obtained from a tool that performs frequent measurements, without requiring the active intervention of the patient, even in times of the day which cannot be analyzed in detail with the traditional systems. This difference is exemplified in glycemic profile shown in FIG. 2: a trend apparently satisfactory, if judged by isolated points detected with SMBG, reveals significant glucose excursions when the observation is made in a "continuous" way. Therefore, SMBG provides a limited and isolated number of accurate measurements, thus only roughly indicative of the overall picture, instead CGM, if correctly calibrated, gives a more detailed and representative picture of the real clinical situation.

Figure 2:
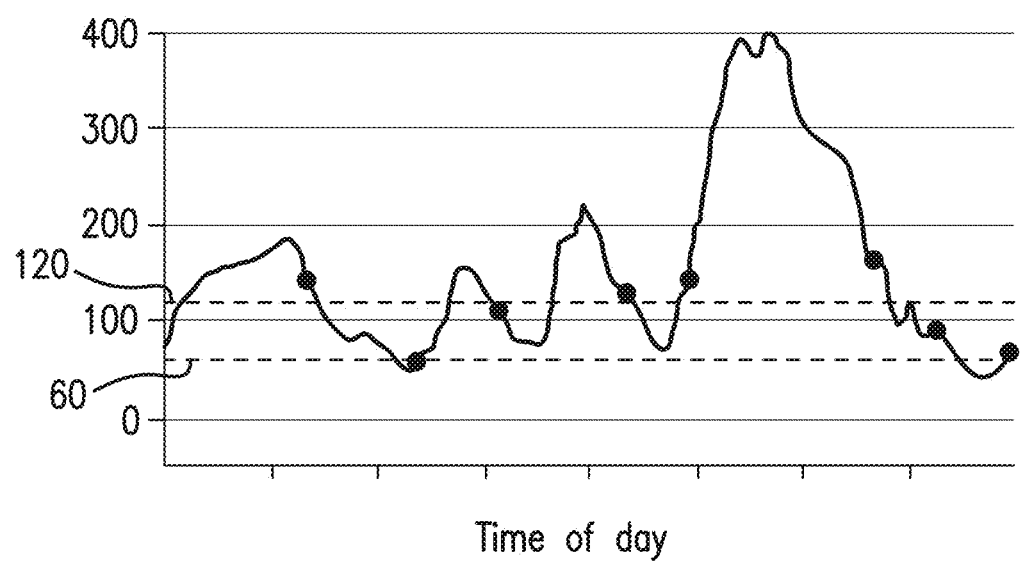
FIG. 2 is a chart comparing between glycemic profiles obtained with self-monitoring of blood glucose (SMBG) system (filled circles) and continuous glucose monitoring (CGM) system (continuous line).

FIG. 2: Comparison between glycemic profiles obtained with SMBG (filled circles) and CGM (continuous line)

The first CGM systems offered only an "offline" interpretation of the glucose profiles after disconnecting the sensor and uploading the results.

In the past years, "online" or "real-time" continuous glucose monitoring systems have become available, allowing direct feedback of glucose levels. Some CGM devices have been approved by the U.S. Food and Drug Administration (FDA) and are available by prescription: these provide real-time measurements of glucose levels, with glucose levels displayed at 5-minute or 1-minute intervals. Users can set alarms to alert them when glucose levels are too low or too high. Special software is available to download data from the devices to a computer for tracking and analysis of patterns and trends, and the systems can display trend graphs on the monitor screen.

Conventionally, it is usual to distinguish continuous glucose monitoring devices in: (i) minimally invasive sensors (e.g., with systems of micro dialysis, based on ionophoresis, or based on electrochemistry), (ii) non-invasive sensors (e.g., based on spectroscopy or based on light scattering), and (iii) totally implantable glucose sensors (e.g., intravascular or subcutaneous).

In this application, the focus is on a subcutaneous totally implantable, abiotic and fluorescent-based instrumentation CGM system. However, embodiments of the invention are applicable to analyte monitoring systems including different types of analyte sensors.

2. The Analyte Monitoring System 2.1 Components

Figure 3:
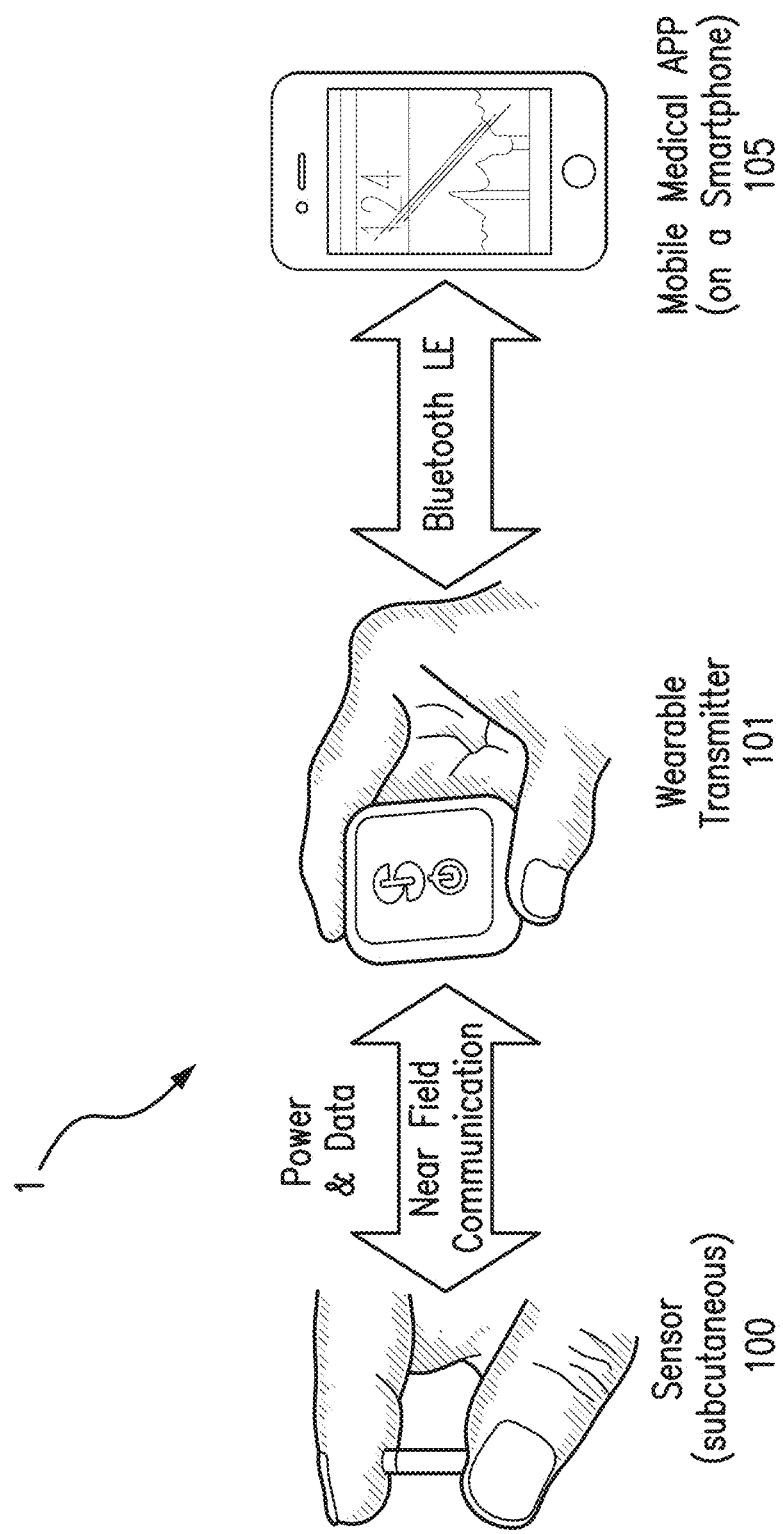
FIG. 3 is a schematic view illustrating an analyte monitoring system embodying aspects of the present invention.

FIG. 3 is a schematic view of an analyte monitoring system 1 embodying aspects of the present invention. The analyte monitoring system 1 may be a continuous analyte monitoring system (e.g., a CGM system). In some embodiments, the analyte monitoring system 1 may include one or more of an analyte sensor 100, a transmitter 101, and a display device 105. In some embodiments, the sensor 100 may be small, fully subcutaneously insertable sensor measures analyte (e.g., glucose) concentrations in a medium (e.g., interstitial fluid) of a living animal (e.g., a living human). However, this is not required, and, in some alternative embodiments, the sensor 100 may be a partially insertable (e.g, transcutaneous) sensor or a fully external sensor. In some embodiments, the transmitter 101 may be an externally worn transmitter (e.g., attached via an armband, wristband, waistband, or adhesive patch). In some embodiments, the transmitter 101 may remotely power and communicate with the inserted sensor to initiate and receive the measurements (e.g., via near field communication). However, this is not required, and, in some alternative embodiments, the transmitter 101 may power and/or communicate with the sensor 100 via one or more wired connections. In some embodiments, the transmitter 101 may communicate information (e.g., one or more analyte concentrations) wirelessly (e.g., via a Bluetooth™ communication standard such as, for example and without limitation Bluetooth Low Energy) to a hand held application running on a display device 105 (e.g., smartphone). In some embodiments, information can be downloaded from the transmitter 101 through a Universal Serial Bus (USB) port. In some embodiments, the analyte monitoring system 1 may include a web interface for plotting and sharing of uploaded data.

Figure 4:
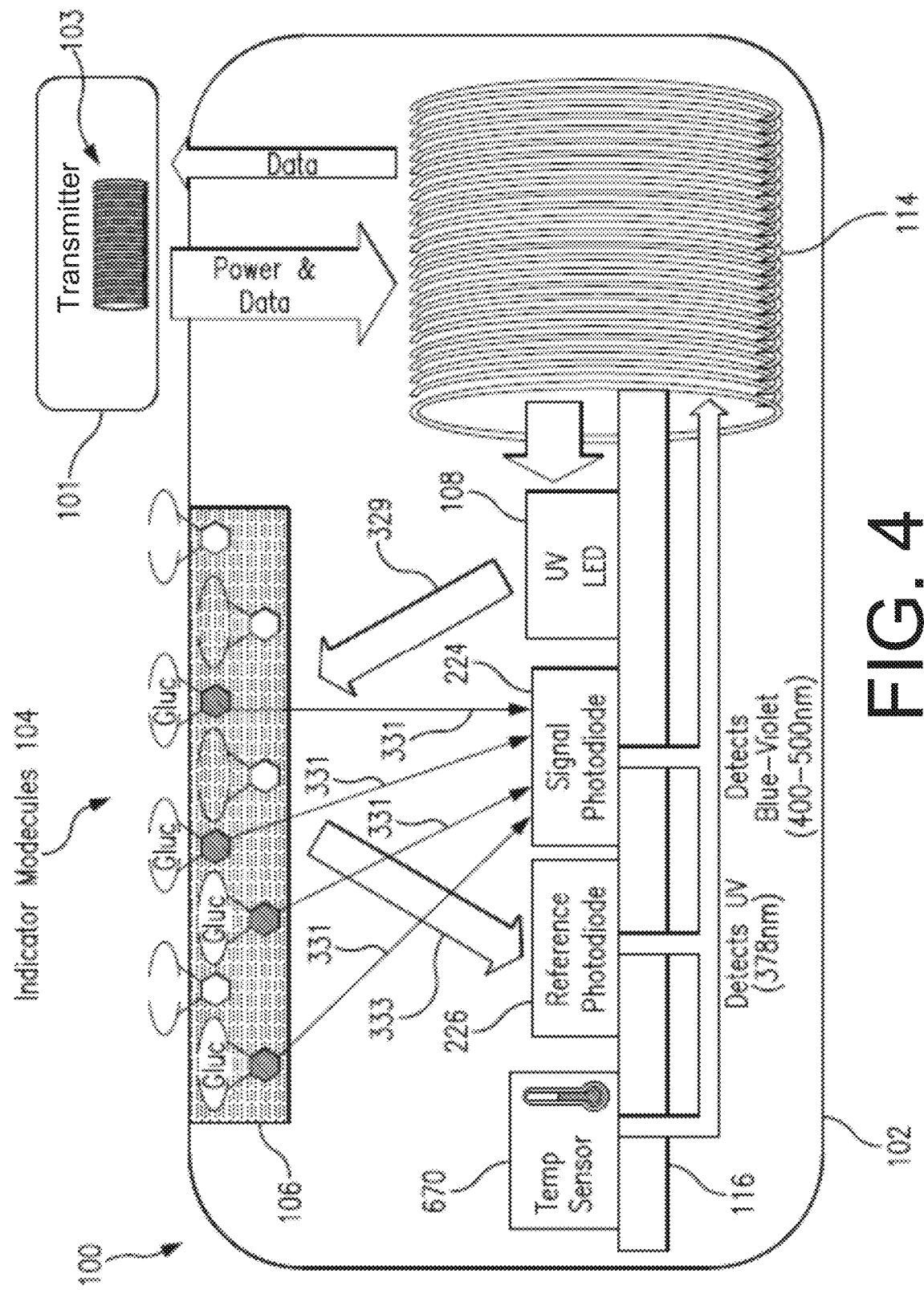
FIG. 4 is a schematic view illustrating a sensor and transmitter of an analyte monitoring system embodying aspects of the present invention.

In some embodiments, as illustrated in FIG. 4, the transmitter 101 may include an inductive element 103, such as, for example, a coil. The transmitter 101 may generate an electromagnetic wave or electrodynamic field (e.g., by using a coil) to induce a current in an inductive element 114 of the sensor 100, which powers the sensor 100. The transmitter 101 may also convey data (e.g., commands) to the sensor 100. For example, in a non-limiting embodiment, the transmitter 101 may convey data by modulating the electromagnetic wave used to power the sensor 100 (e.g., by modulating the current flowing through a coil 103 of the transmitter 101). The modulation in the electromagnetic wave generated by the transmitter 101 may be detected/extracted by the sensor 100. Moreover, the transmitter 101 may receive data (e.g., measurement information) from the sensor 100. For example, in a non-limiting embodiment, the transmitter 101 may receive data by detecting modulations in the electromagnetic wave generated by the sensor 100, e.g., by detecting modulations in the current flowing through the coil 103 of the transmitter 101.

The inductive element 103 of the transmitter 101 and the inductive element 114 of the sensor 100 may be in any configuration that permits adequate field strength to be achieved when the two inductive elements are brought within adequate physical proximity.

In some non-limiting embodiments, as illustrated in FIG. 4, the sensor 100 may be encased in a sensor housing 102 (i.e., body, shell, capsule, or encasement), which may be rigid and biocompatible. The sensor 100 may include an analyte indicator element 106, such as, for example, a polymer graft coated, diffused, adhered, or embedded on or in at least a portion of the exterior surface of the sensor housing 102. The analyte indicator element 106 (e.g., polymer graft) of the sensor 100 may include indicator molecules 104 (e.g., fluorescent indicator molecules) exhibiting one or more detectable properties (e.g., optical properties) based on the amount or concentration of the analyte in proximity to the analyte indicator element. In some embodiments, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from the analyte indicator element 106 as reflection light 333. In some non-limiting embodiments, one or more of the photodetectors may be covered by one or more filters that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the sensor 100 may include a temperature transducer 670. In some non-limiting embodiments, the sensor 100 may include a drug-eluting polymer matrix that disperses one or more therapeutic agents (e.g., an anti-inflammatory drug).

In some embodiments, as illustrated in FIG. 4, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to semiconductor substrate 116 and/or a core (e.g., a ferrite core) for the inductive element 114. In some embodiments, the semiconductor substrate 116 and/or a core may provide communication paths between the various secured components.

In some embodiments, the one or more of the sensor housing 102, analyte indicator element 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transmitter 101 may be as described in one or more of U.S. application Ser. Nos. 13/761,839, 13/937,871, and 13/650,016.

Although in some embodiments, as illustrated in FIGS. 3 and 4, the sensor 100 may be an optical sensor, this is not required, and, in one or more alternative embodiments, sensor 100 may be a different type of analyte sensor, such as, for example, a diffusion sensor or a pressure sensor. Also, although in some embodiments, as illustrated in FIGS. 3 and 4, the analyte sensor 100 may be a fully implantable sensor, this is not required, and, in some alternative embodiments, the sensor 100 may be a transcutaneous sensor having a wired connection to the transmitter 101. For example, in some alternative embodiments, the sensor 100 may be located in or on a transcutaneous needle (e.g., at the tip thereof). In these embodiments, instead of wirelessly communicating using inductive elements 103 and 114, the sensor 100 and transmitter 101 may communicate using one or more wires connected between the transmitter 101 and the transmitter transcutaneous needle that includes the sensor 100. For another example, in some alternative embodiments, the sensor 100 may be located in a catheter (e.g., for intravenous blood glucose monitoring) and may communicate (wirelessly or using wires) with the transmitter 101.

In some embodiments, the sensor 100 may include a transmitter interface device. In some embodiments where the sensor 100 includes an antenna (e.g., inductive element 114), the transmitter interface device may include the antenna (e.g., inductive element 114) of sensor 100. In some of the transcutaneous embodiments where there exists a wired connection between the sensor 100 and the transmitter 101, the transmitter interface device may include the wired connection.

Figure 5:
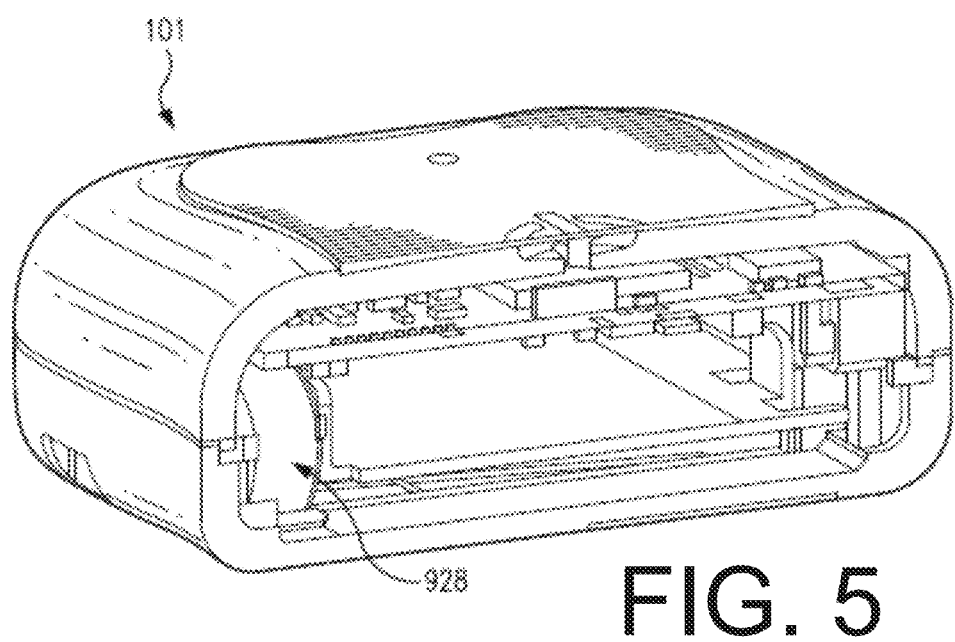
FIG. 5 is cross-sectional, perspective view of a transmitter embodying aspects of the invention.
Figure 6:
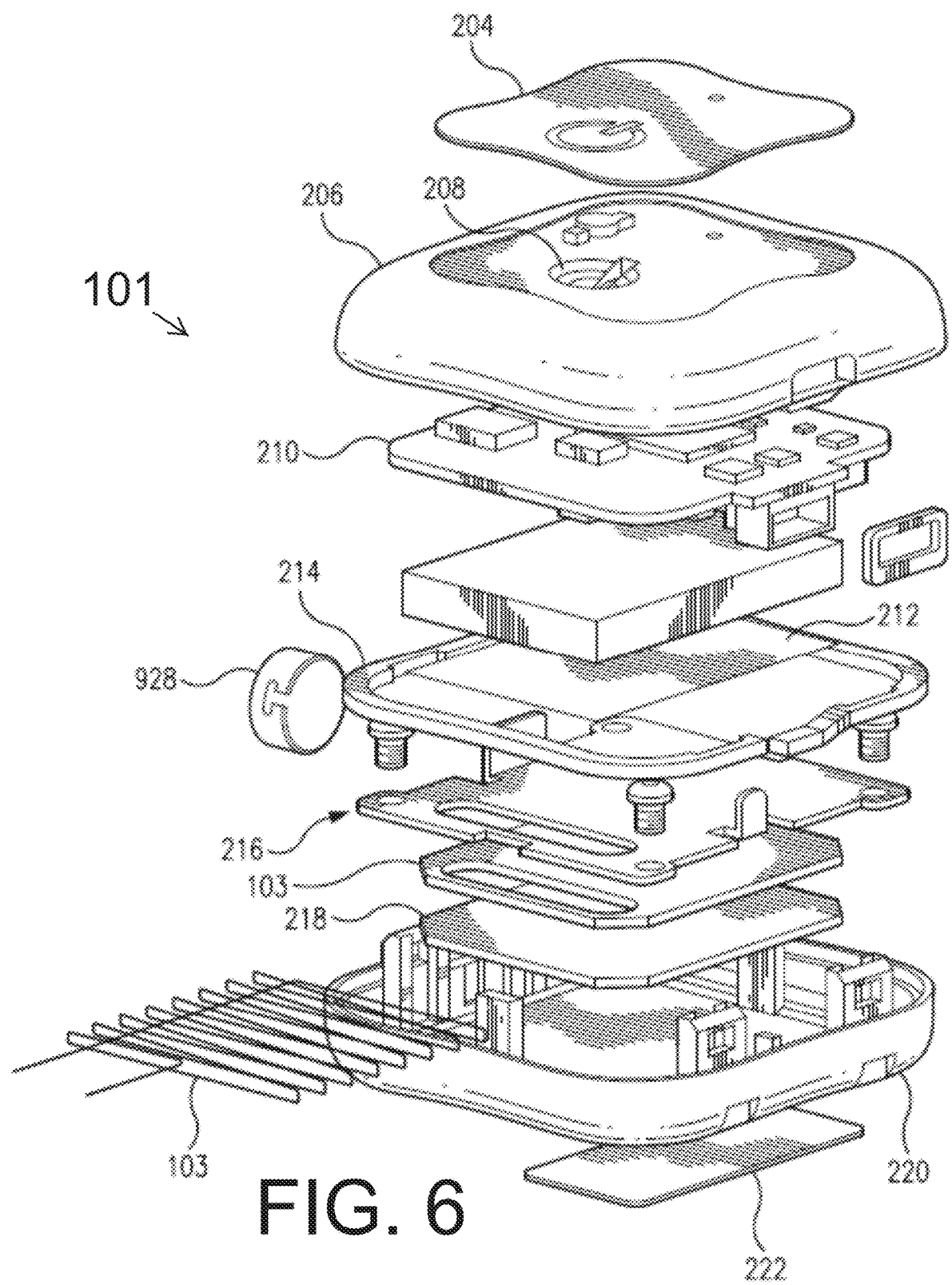
FIG. 6 is an exploded, perspective view of a transmitter embodying aspects of the invention.

FIGS. 5 and 6 are cross-sectional and exploded views, respectively, of a non-limiting embodiment of the transmitter 101, which may be included in the analyte monitoring system illustrated in FIGS. 3 and 4. As illustrated in FIG. 6, in some non-limiting embodiments, the transmitter 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting embodiments, the vibration motor 928 may be attached to the front housing 206 or back housing 220 such that the battery 212 does not dampen the vibration of vibration motor 928. In a non-limiting embodiment, the transmitter electronics may be assembled using standard surface mount device (SMD) reflow and solder techniques.

In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transmitter assembly process may be performed at one or more electronics houses, which may be internal, external, or a combination thereof. In some embodiments, the assembled transmitter 101 may be programmed and functionally tested. In some embodiments, assembled transmitters 101 may be packaged into their final shipping containers and be ready for sale.

In some embodiments, as illustrated in FIGS. 5 and 6, the antenna 103 may be contained within the housing 206 and 220 of the transmitter 101. In some embodiments, the antenna 103 in the transmitter 101 may be small and/or flat so that the antenna 103 fits within the housing 206 and 220 of a small, lightweight transmitter 101. In some embodiments, the antenna 103 may be robust and capable of resisting various impacts. In some embodiments, the transmitter 101 may be suitable for placement, for example, on an abdomen area, upper-arm, wrist, or thigh of a patient body. In some non-limiting embodiments, the transmitter 101 may be suitable for attachment to a patient body by means of a biocompatible patch. Although, in some embodiments, the antenna 103 may be contained within the housing 206 and 220 of the transmitter 101, this is not required, and, in some alternative embodiments, a portion or all of the antenna 103 may be located external to the transmitter housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 7:
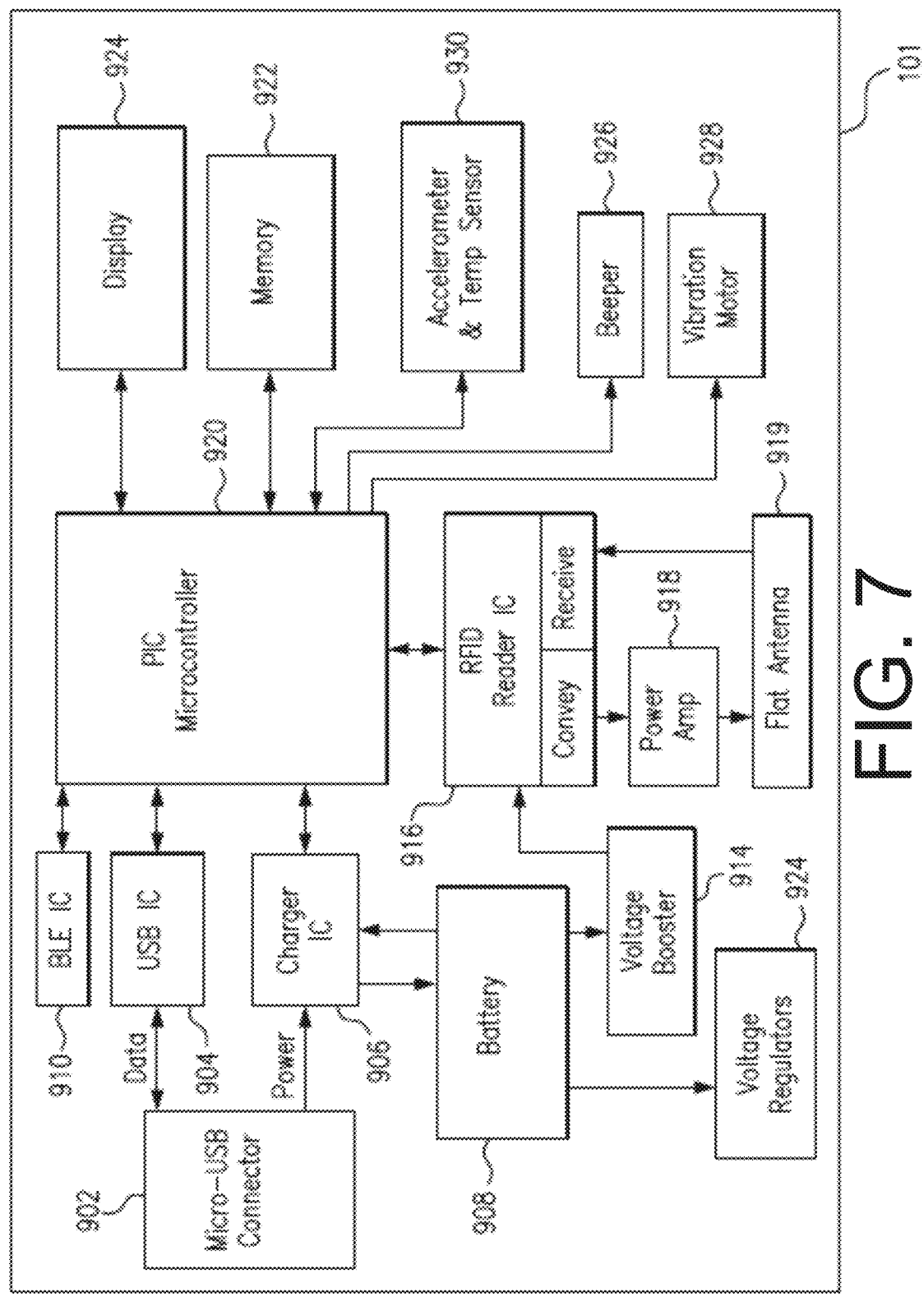
FIG. 7 is a schematic view illustrating a transmitter embodying aspects of the present invention.

FIG. 7 is a schematic view of an external transmitter 101 according to a non-limiting embodiment. In some embodiments, the transmitter 101 may have a connector 902, such as, for example, a Micro-Universal Serial Bus (USB) connector. The connector 902 may enable a wired connection to an external device, such as a personal computer (e.g., personal computer 109) or a display device 105 (e.g., a smartphone).

The transmitter 101 may exchange data to and from the external device through the connector 902 and/or may receive power through the connector 902. The transmitter 101 may include a connector integrated circuit (IC) 904, such as, for example, a USB-IC, which may control transmission and receipt of data through the connector 902. The transmitter 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transmitter 101 may include one or more connectors in addition to (or as an alternative to) Micro-USB connector 904. For example, in one alternative embodiment, the transmitter 101 may include a spring-based connector (e.g., Pogo pin connector) in addition to (or as an alternative to) Micro-USB connector 904, and the transmitter 101 may use a connection established via the spring-based connector for wired communication to a personal computer (e.g., personal computer 109) or a display device 105 (e.g., a smartphone) and/or to receive power, which may be used, for example, to charge the battery 908.

In some embodiments, the transmitter 101 may have a wireless communication IC 910, which enables wireless communication with an external device, such as, for example, one or more personal computers (e.g., personal computer 109) or one or more display devices 105 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna). In some non-limiting embodiments, the antenna of the wireless communication IC 910 may be entirely contained within the housing (e.g., housing 206 and 220) of the transmitter 101. However, this is not required, and, in alternative embodiments, all or a portion of the antenna of the wireless communication IC 910 may be external to the transmitter housing.

In some embodiments, the transmitter 101 may include a display interface device, which may enable communication by the transmitter 101 with one or more display devices 105. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, the transmitter 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting embodiments, the sensor 100 and transmitter 101 may communicate using near field communication (NFC) (e.g., at a frequency of 13.56 MHz). In the illustrated embodiment, the inductive element 103 is a flat antenna. In some non-limiting embodiments, the antenna may be flexible. However, as noted above, the inductive element 103 of the transmitter 101 may be in any configuration that permits adequate field strength to be achieved when brought within adequate physical proximity to the inductive element 114 of the sensor 100. In some embodiments, the transmitter 101 may include a power amplifier 918 to amplify the signal to be conveyed by the inductive element 103 to the sensor 100.

The transmitter 101 may include a peripheral interface controller (PIC) microcontroller 920 and memory 922 (e.g., Flash memory), which may be non-volatile and/or capable of being electronically erased and/or rewritten. The PIC microcontroller 920 may control the overall operation of the transmitter 101. For example, the PIC microcontroller 920 may control the connector IC 904 or wireless communication IC 910 to transmit data via wired or wireless communication and/or control the RFID reader IC 916 to convey data via the inductive element 103. The PIC microcontroller 920 may also control processing of data received via the inductive element 103, connector 902, or wireless communication IC 910.

In some embodiments, the transmitter 101 may include a sensor interface device, which may enable communication by the transmitter 101 with a sensor 100. In some embodiments, the sensor interface device may include the inductive element 103. In some non-limiting embodiments, the sensor interface device may additionally include the RFID reader IC 916 and/or the power amplifier 918. However, in some alternative embodiments where there exists a wired connection between the sensor 100 and the transmitter 101 (e.g., transcutaneous embodiments), the sensor interface device may include the wired connection.

In some embodiments, the transmitter 101 may include a display 924 (e.g., liquid crystal display and/or one or more light emitting diodes), which PIC microcontroller 920 may control to display data (e.g., glucose concentration values). In some embodiments, the transmitter 101 may include a speaker 926 (e.g., a beeper) and/or vibration motor 928, which may be activated, for example, in the event that an alarm condition (e.g., detection of a hypoglycemic or hyperglycemic condition) is met. The transmitter 101 may also include one or more additional sensors 930, which may include an accelerometer and/or temperature sensor, that may be used in the processing performed by the PIC microcontroller 920.

In some embodiments, the transmitter 101 may be a body-worn transmitter that is a rechargeable, external device worn over the sensor implantation or insertion site. The transmitter 101 may supply power to the proximate sensor 100, calculate analyte concentrations from data received from the sensor 100, and/or transmit the calculated analyte concentrations to a display device 105 (see FIG. 3). Power may be supplied to the sensor 100 through an inductive link (e.g., an inductive link of 13.56 MHz). In some embodiments, the transmitter 101 may be placed using an adhesive patch or a specially designed strap or belt. The external transmitter 101 may read measured analyte data from a subcutaneous sensor 100 (e.g., up to a depth of 2 cm or more). The transmitter 101 may periodically (e.g., every 2 minutes) read sensor data and calculate an analyte concentration and an analyte concentration trend. From this information, the transmitter 101 may also determine if an alert and/or alarm condition exists, which may be signaled to the user (e.g., through vibration by vibration motor 928 and/or an LED of the transmitter's display 924 and/or a display of a display device 105). The information from the transmitter 101 (e.g., calculated analyte concentrations, calculated analyte concentration trends, alerts, alarms, and/or notifications) may be transmitted to a display device 105 (e.g., via Bluetooth Low Energy with Advanced Encryption Standard (AES)-Counter CBC-MAC (CCM) encryption) for display by a mobile medical application on the display device 105. In some non-limiting embodiments, the mobile medical application may provide alarms, alerts, and/or notifications in addition to any alerts, alarms, and/or notifications received from the transmitter 101. In one embodiment, the mobile medical application may be configured to provide push notifications. In some embodiments, the transmitter 101 may have a power button (e.g., button 208) to allow the user to turn the device on or off, reset the device, or check the remaining battery life. In some embodiments, the transmitter 101 may have a button, which may be the same button as a power button or an additional button, to suppress one or more user notification signals (e.g., vibration, visual, and/or audible) of the transmitter 101 generated by the transmitter 101 in response to detection of an alert or alarm condition.

2.1.1 Subcutaneously Insertable Abiotic Fluorescent Sensor

Figure 8A:
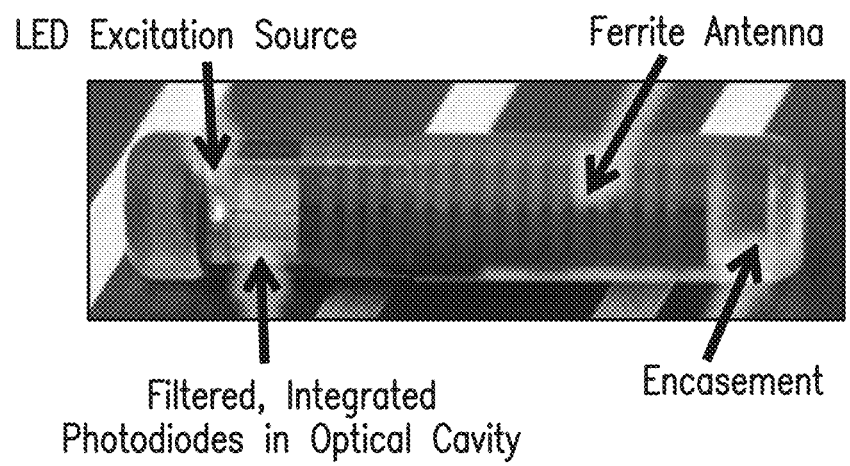
FIG. 8A illustrates an analyte sensor (shown without an analyte-indicator hydrogel coating) embodying aspects of the present invention.

In some non-limiting embodiments, as shown in FIG. 8A, the sensor 100 may be a micro-fluorometer that is encased in a rigid, translucent, and/or biocompatible polymer capsule (e.g., PMMA) 102. The capsule 102 may be, for example and without limitation, 3.3 mm in diameter and 15 mm in length.

In some embodiments, analyte concentration may be measured by means of fluorescence from the indicator element 106 (e.g., the analyte-indicating hydrogel), which may be, for example and without limitation, polymerized onto the capsule surface over the optical cavity. The optical system contained within the capsule 102 may include one or more of a light-emitting diode (LED) 108, which may serve as the excitation source for the indicator element 106; one or more photodetectors 224 and 226, which may be, for example and without limitation, spectrally filtered photodiodes, which may measure the analyte-dependent fluorescence intensity; circuitry (e.g., a custom integrated circuit with onboard temperature sensor); an on-board nonvolatile storage medium (e.g., an electrically erasable programmable memory (EEPROM)), which may be for local configuration storage and/or production traceability; and an antenna 114, which may receive power from and communicates with the transmitter 101.

Figure 8B:
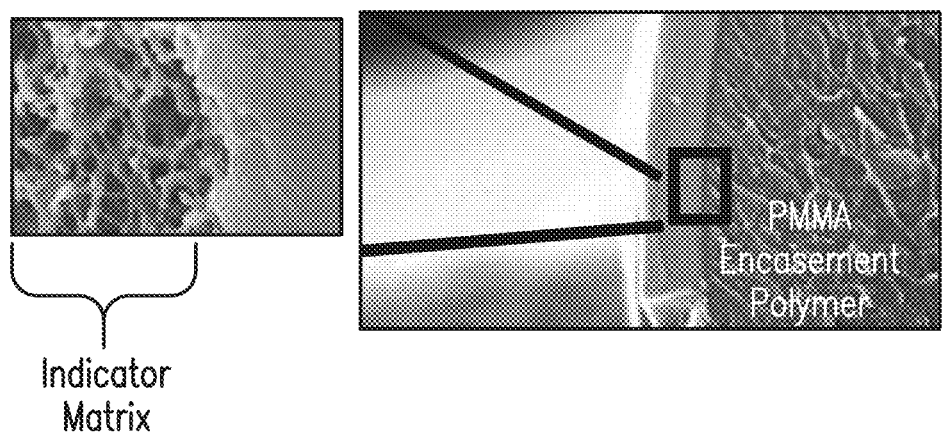
FIG. 8B illustrates an analyte indicator of an analyte sensor embodying aspects of the present invention.
Figure 8C:
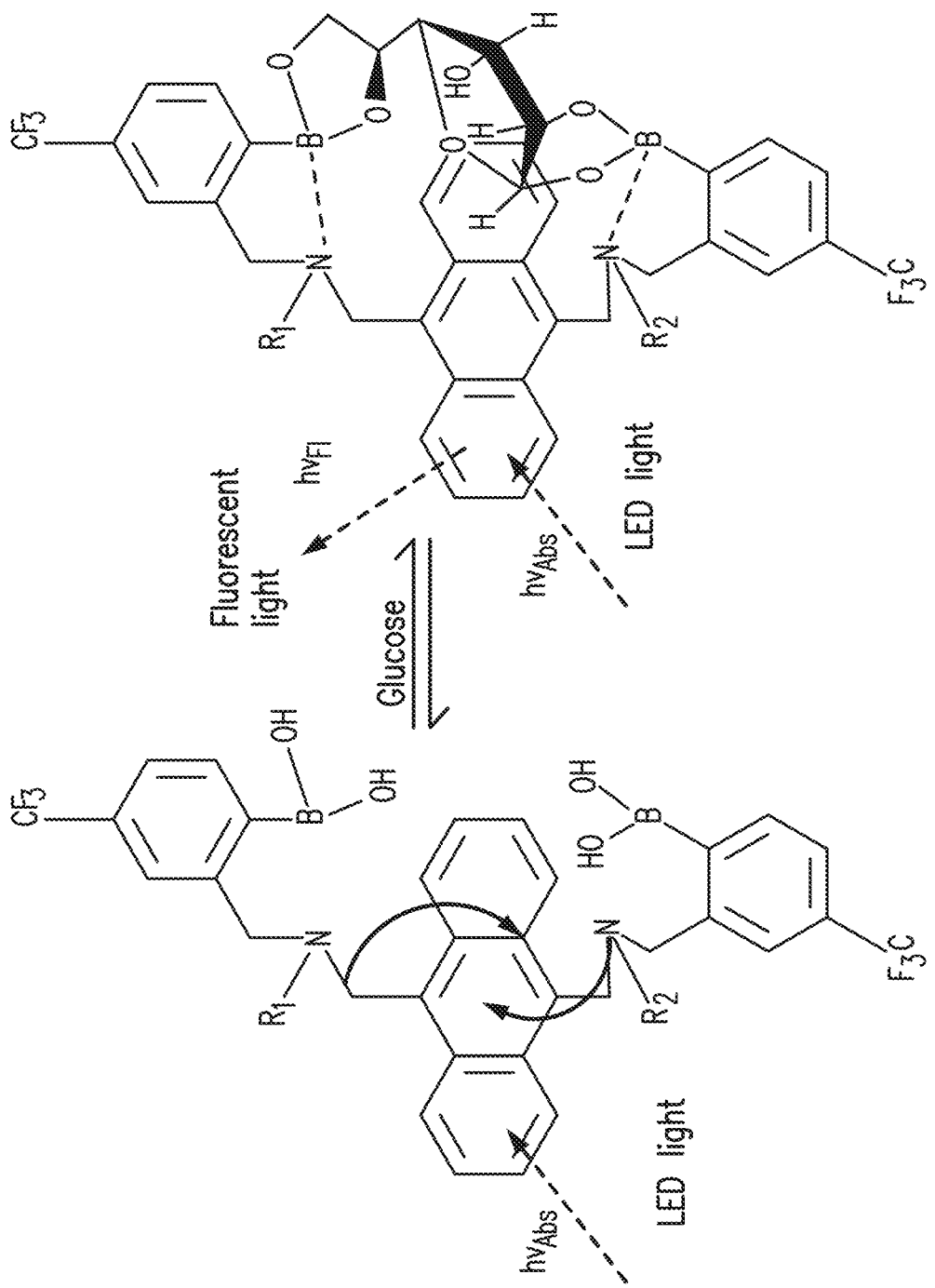
FIG. 8C illustrates the chemical structure and glucose binding mode of indicator moiety of a sensor embodying aspects of the present invention.

FIGS. 8A-8C illustrate an implantable optical-based glucose sensor. FIG. 8A is a photograph of the implantable glucose sensor (shown without glucose-indicator hydrogel coating); FIG. 8B shows scanning electron microscope (SEM) images of the glucose indicator hydrogel grafted onto the outside of the PMMA sensor encasement; and FIG. 8C shows a chemical structure and glucose binding mode of indicator moiety. R2 shown in the figure denotes connectivity to the hydrogel backbone, while R1 represents a propionic acid side chain.

In some non-limiting embodiments, as shown in FIG. 8B, the analyte indicator 106 (e.g., glucose-indicating hydrogel) may include poly(2-hydroxyethyl methacrylate) (pHEMA) into which a fluorescent indicator (FIG. 8C) may be co-polymerized. In some non-limiting embodiments, in contrast to CGMs that utilize electrochemical enzyme-based glucose sensors, no chemical compounds are consumed (i.e., glucose, oxygen) or formed (i.e., hydrogen peroxide) during use, and the glucose-indicating hydrogel may not subject to the instability characteristics of enzymes. Instead, glucose may reversibly binds to the indicator boronic acids groups (which act as glucose receptors) in an equilibrium binding reaction. Subsequent disruption of photoinduced electron transfer (PET) results in an increased fluorescence intensity upon glucose binding. When glucose is not present, anthracene fluorescence may be quenched by intermolecular electron transfer (indicated by the curved arrows in FIG. 8C) from the unpaired electrons on the indicator tertiary amines. When glucose is bound to the boronic acids, the Lewis acidity of boron may be increased, and weak boron-nitrogen bonds are formed. This weak bonding may prevent electron transfer from the amines and may consequently prevent fluorescence quenching. In some embodiments, the indicator is not chemically altered as a result of the PET quenching process. Fluorescence increases with increasing glucose concentrations until all indicator binding sites are filled at which point the signal reaches a plateau. In some embodiments, an anti-oxidant layer (e.g., platinum) may be deposited onto the sensor 100 by sputter coating, which may serve to prevent in-vivo oxidation of the indicator phenylboronic acids groups. Platinum catalytically degrades the reactive oxygen species that are otherwise generated by the body's normal wound healing response to sensor insertion and by the body's response to a foreign body. In some embodiments, a glucose-permeable membrane may cover the analyte indicator 106 (e.g., hydrogel) and may provide a biocompatible interface. In some embodiments, the ability of the sensor 100 to communicate may be mediated by a near field communication (NFC) interface to the external transmitter 101. In some embodiments, the sensor 100 may not contain a battery or other stored power source; instead, the sensor 100 may be remotely and discretely powered, as needed, by a simple inductive magnetic link between the sensor and the transmitter 101. On power-up, the LED source 108 may be energized (e.g., for approximately 4 ms) to excite the fluorescent indicator. Between readings, the sensor 100 may remain electrically dormant and fully powered down.

2.1.2 Wearable Transmitter

In some embodiments, the body-worn transmitter 101 may be a rechargeable, external device that is worn over the sensor implantation site and that supplies power to the proximate sensor 100, calculates glucose concentration from data received from the sensor, and/or transmits the glucose calculation to a smartphone 105. The transmitter 101 may supply power to the sensor 100 through an inductive link (e.g., of 13.56 MHz). The transmitter 101 may be placed using an adhesive patch or band (i.e., armband, waistband, and wristband). The transmitter 101 may power and activate a measurement sequence (e.g., every 2 min), read measured glucose data from the sensor 100 (e.g., up to a depth of approximately 2-3 cm) and then calculate glucose concentrations and/or trends. This information may also enable the transmitter 101 to determine if an alert condition exists, which may be communicated to the wearer through vibration and/or the transmitter's display 924. The information from the transmitter 101 may then transmitted for display to a smartphone 105 (e.g., via a Bluetooth™ low energy link).

2.2 System Setup and Calibration

In some embodiments, the analyte monitoring system 1 may include one or more of three different phases: Warm up, Initialization, and Calibration phases. In some embodiments, the sensor 100 may be inserted into the subcutaneous space (e.g., using aseptic technique via a small incision (~0.8-1.0 cm) made under local anesthesia with lidocaine). Two 5-0 nylon sutures may be used to close the wound. A typical insertion time may be less than 5 min. In some embodiments, after the insertion of the sensor 100, the transmitter 101 and the application may be paired, and the sensor 100 and the transmitter 101 linked. Then, the Warm up phase may begin (e.g., day 0, 24 h after insertion), in which the transmitter 101 is not worn, and no calibration is done. In the Initialization phase (e.g., day 1, 24 h) four SMBG measurements may be used to calibrate the system 1. Each SMBG measurement entry may be, for example, 2-12 hours apart. After that, the Daily calibration phase begins, and one or more (e.g., two) SMBG measurements entries per time period (e.g., day or week) may be done. In some embodiments, each SMBG measurement entry may be 10-14 hours apart, and the system 1 may allow preferred daily calibration times to be set by patient, e.g., 08:00 and 18:00. The removal of the sensor 100 (e.g., upon completion of a study or end of sensor life) may be performed using aseptic techniques (e.g., under local anesthesia with lidocaine). In some embodiments, a small incision may be made at the proximal end of the sensor location, and manual pressure may be applied to the distal end to extrude the sensor from the subcutaneous space through the incision. A thin adhesive strip or suture may be applied to assure closure at the removal site. Typical excision times may be less than 5 min.

2.3 Overrating Principle

Figure 9:
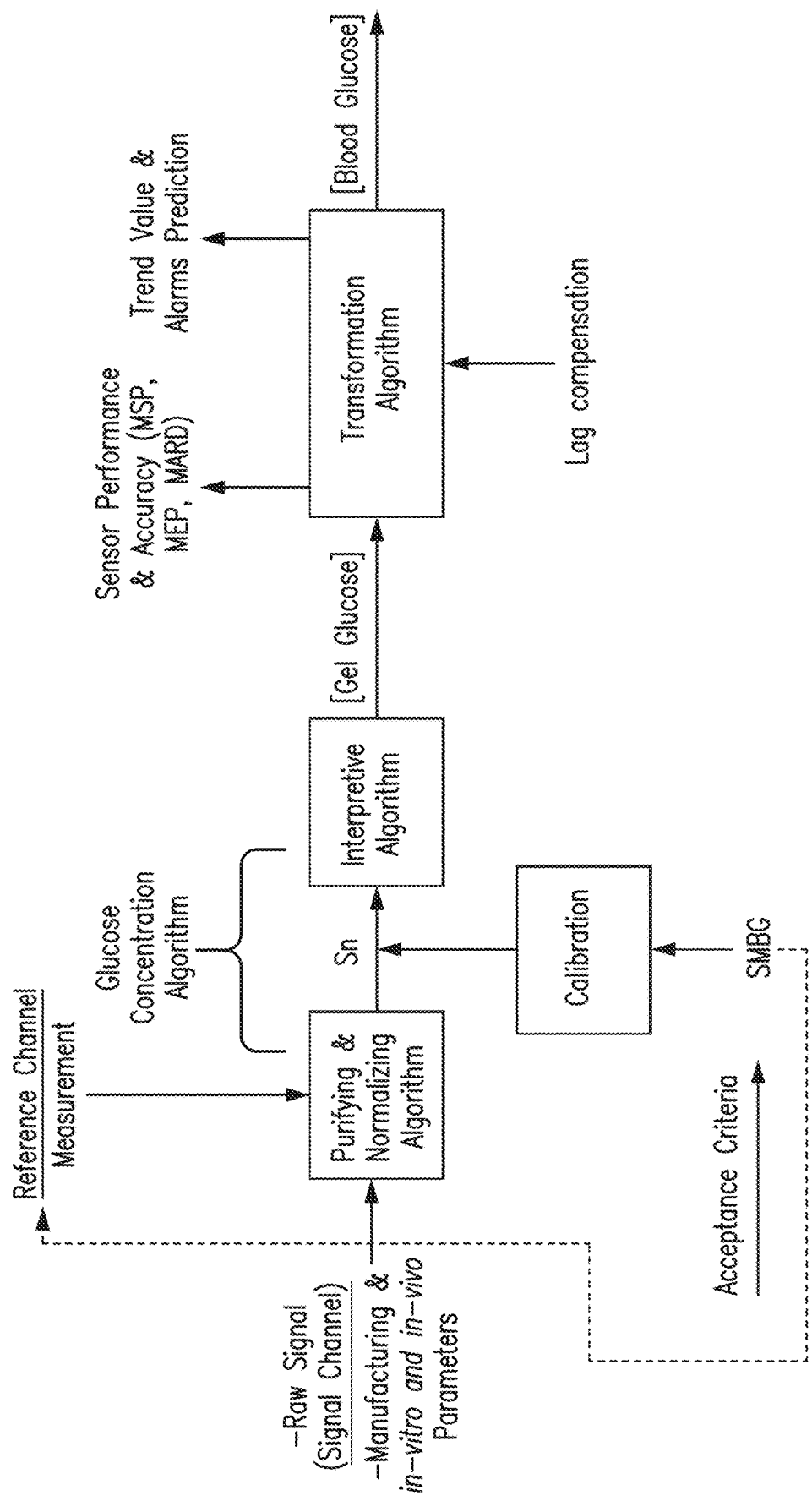
FIG. 9 illustrates one or more functions that may be performed by an analyte monitoring system embodying aspects of the present invention.

In some embodiments, the analyte monitoring system 1 may be configured to perform one or more of the functions illustrated in FIG. 9. In some non-limiting embodiments, the transmitter 101 (e.g., the microcontroller 920 of the transmitter 101) may be configured to perform one or more of the functions illustrated in FIG. 9. However, this is not required, and, in some alternative embodiments, the sensor 100 (e.g., circuitry, such as an ASIC, of the sensor 100) may be configured to perform one or more of the functions illustrated in FIG. 9. In some non-limiting embodiments, the sensor 100 may measure one or more of the raw fluorescent signal (e.g., emission light 331), the reference signal (e.g., reflection light 333), and the temperature of the sensor 100. In some embodiments, the sensor 100 may convey the measurement information to the transmitter 101. In some embodiments, the analyte monitoring system 1 (e.g., the transmitter 101 of the analyte monitoring system 1) may store one or more parameters measured during manufacturing of the sensor 101 and/or one or more parameters characterized using in-vitro and/or in-vivo tests. Based on one or more of the measurement information and the one or more parameters, the analyte monitoring system 1 may generate a much purified signal derived from glucose modulated indicator fluorescence that is normalized (Sn) and directly proportional to glucose concentration. In some embodiments, the two different measurement channels (signal and reference) of the sensor 100 may be used to calculate the normalized signal. This normalized signal may contain some parameters that have to be calibrated, for a good performance of the system 1. This calibration may be done using one or more SMBG measurements, which the system 1 may receive, for example and without limitation, via patient entry into the hand held application of display device 105, which may convey the one or more SMBG measurements to the transmitter 101. In some embodiments, the calibration evaluate an acceptance criterion. For example, in some non-limiting embodiments, if an SMBG value falls between a certain percent of the latest glucose concentration calculated using the measurement information from the sensor 100, the system 1 may accept it. If not, the system 1 may be configured to treat the SMBG value as wrong, thus having to change its behavior. In some embodiments, the system 1 may be configured to perform an interpretive algorithm that modifies the normalized signal Sn into an interstitial gel glucose concentration. In some embodiments, the analyte monitoring system 1 may be configured to transform the interstitial gel glucose concentration into a real blood glucose concentration (e.g., by a lag compensation algorithm). Besides the blood glucose concentration, the system 1 may generate other outputs, like sensor performance and accuracy metrics as the Metric for real time assessment of Sensor Performance (MSP), the Metric of Electronic Performance (MEP), the Mean Absolute Relative Difference (MARD), and/or trend value and alarms prediction.

Figure 10:
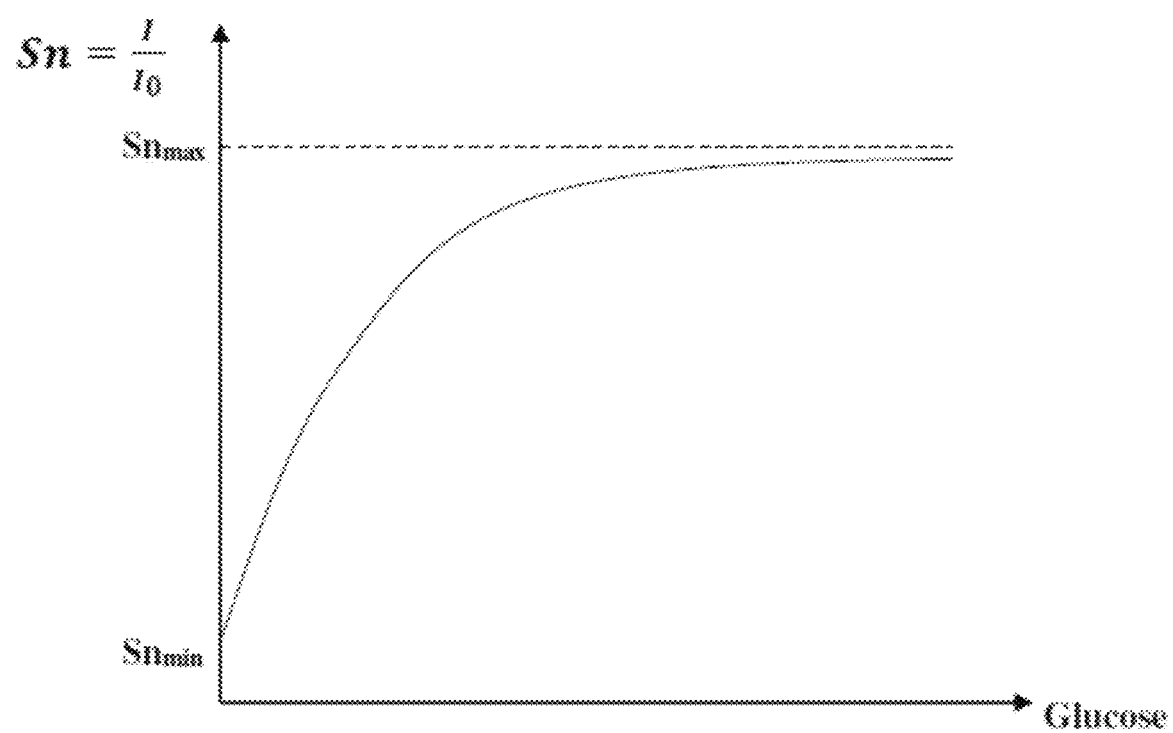
FIG. 10 illustrates indicator normalized modulation VS glucose concentration embodying aspects of the present invention.

In some embodiments, the signal-processing cascade performed by the analyte monitoring system 1 (e.g., by the transmitter 101 of the analyte monitoring system 1) may be based on the relationship shown in FIG. 10. In FIG. 10, I is the fluorescence from the glucose sensor indicator and $I_0$ is baseline fluorescence at zero glucose concentration. The percent modulation $I/I_0$ versus glucose concentration is constant throughout the life of the glucose sensor (indicator). The end of life of the analyte sensor 100 may arise when the signal to noise ratio declines over time to a point where the error specification can no longer be maintained. As mentioned above, once Sn is calculated, the system 1 may use an interpretive algorithm to convert Sn into glucose concentration. This algorithm may be derived through the curve seen in FIG. 10. This curve may be based on the equilibrium reaction:

$$\text{Indicator} + \text{Glucose} \Leftrightarrow \text{Indicator\_Glucose\_Complex} \quad (2.1)$$

The fluorescence of the indicator may increase upon binding glucose. In some embodiments, the analyte monitoring system 1 may purify and transform this fluorescent signal, which may be directly proportional to glucose concentration, to obtain the desired blood glucose concentration.

2.3.1 Signal Purification

The raw signals from the sensor 100, as captured, may contain noise, offset, and/or distortions, which are not related to actual glucose modulation of the indicator 106. The fluorescent amplitude of the indicator 106, as well as some elements of the electronic circuitry within the sensor 100, may be temperature sensitive. The analyte monitoring system 1 may use the Sn equation to purify and normalize the signal by removing the non-glucose-modulated offset/distortion of the signal, and/or may correct for temperature sensitivity. The simplest form of Sn equation is that $$Sn = \frac{I}{I_0} \quad (2.2)$$

where I is the fluorescence from the glucose indicator and I0 is baseline fluorescence at zero glucose concentration. The raw signal measurement data contains offset and all the distortion producing subspecies of FIG. 11:

$$\text{Signal} = I + Z + I_{distortion} \quad (2.3)$$

where, Z is an offset and $I_{distortion}$ is a distortion to the glucose indicator. In order to calculate I, Z and $I_{distortion}$ must be removed from the raw signal.

Figure 11:
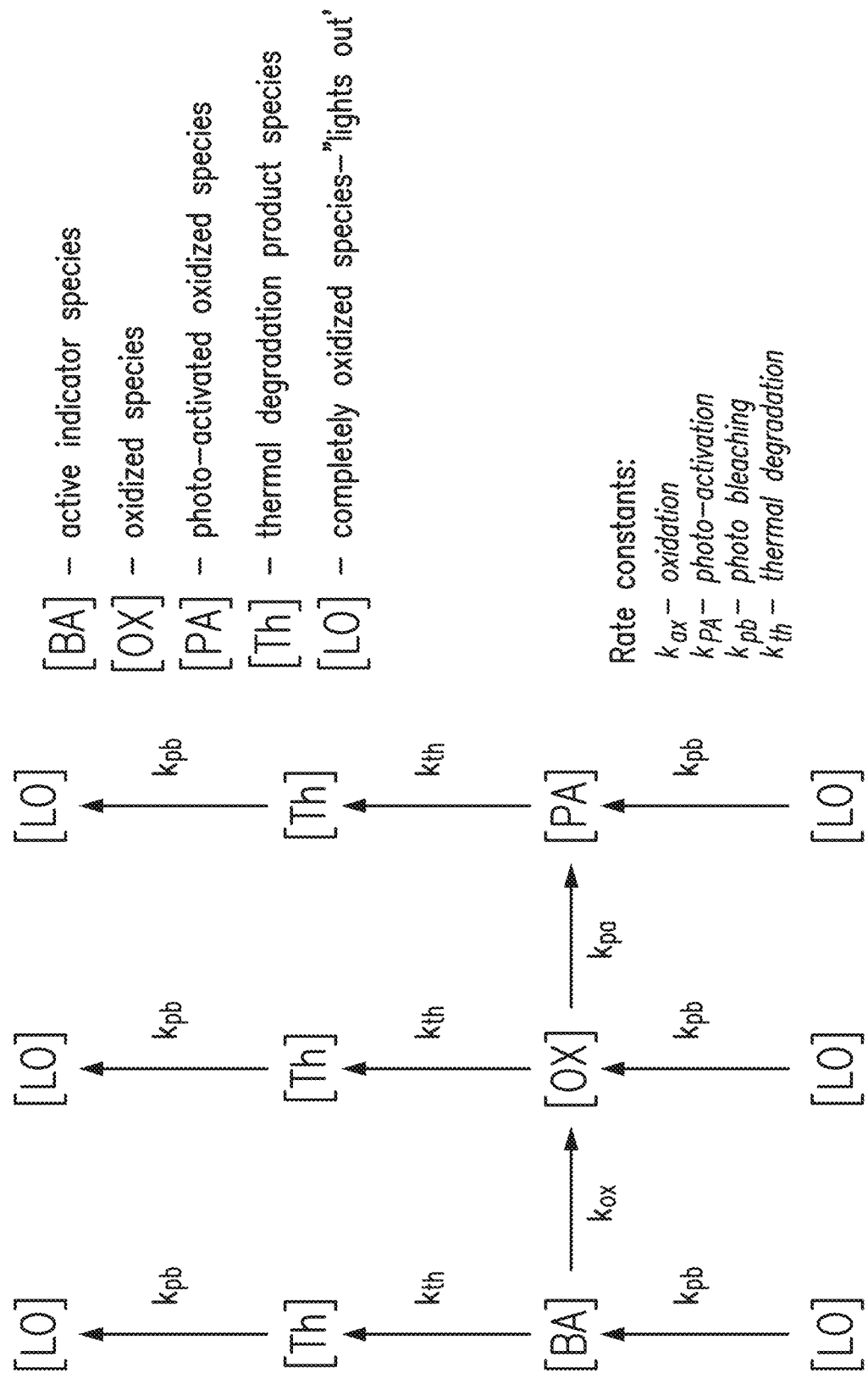
FIG. 11 illustrates the reactions and kinetics of the related species of the indicator molecules of a sensor embodying aspects of the present invention.

FIG. 11: Reactions and kinetics

Figure 12:
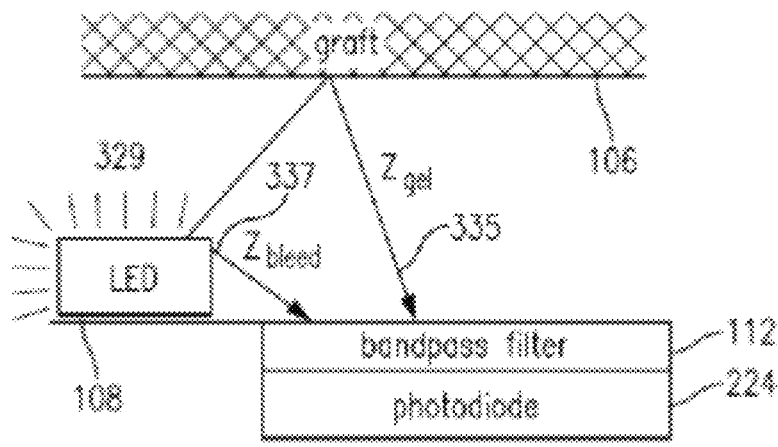
FIG. 12 illustrates the components of the excitation light received by the photodetector that contribute to the offset in the raw signal in an analyte monitoring system embodying aspects of the present invention.

As illustrated in FIG. 12, the excitation light 329 emitted from light source 108 that reaches the photodetector may include (i) a reflection light component 335 that is reflected from the graft 106 (e.g., gel) before reaching the photodetector and (ii) a bleed light component 337 that reaches the photodetector without encountering the graft 106. The reflection light component 335 may produce a reflection component $Z_{gel}$ of the offset Z, and the bleed light component 337 may produce a bleed component $Z_{bleed}$ of the offset Z.

In some embodiments, the offset (Z) may be hardware based, due to LED light that is not absorbed by the indicator 106, mostly because it did not encounter an indicator molecule 104. That light (offset) is then removed by Sn equation, since it is convoluted in the total light arriving at the photodetector. In some embodiments, the offset may be measured during the manufacturing of the sensor 100, and the offset may increase due to photo-bleaching (i.e., the fluorescent reagents "shutdown" reaction). However, in some embodiments, the Sn equation may dynamically track the offset, with the reference channel photodiode. Considering the FIG. 12, Z may be described as $$[Z] = Z_{gel}[1+\phi_Z(1-e^{-k_{pb}t_{pb}})] + Z_{bleed} \quad (2.4)$$

Zgel is the LED spillover component 335 which is reflected from the gel (graft) to the photodetector, while Zbleed is the component 337 directly detected from the photodetector. As the indicator is photo-bleached, the overall absorbance of the gel decreases, which increases the reflectance. φZ is the percent increase of Zgel when the indicator is fully photo-bleached. In some non-limiting embodiments, the offset (Z) may be used to normalize each sensor's output to a numerical value equal to one at zero glucose concentration (Snmin).

The system distortion (Idistortion) is chemistry (photochemistry) and kinetics based. The distortion is any non-glucose-modulated light arriving at the photodetector. In particular, photo [PA], thermal [Th], and oxidative [Ox] decay species emit fluorescent light that is not modulated by glucose, as shown within FIG. 11. These mechanisms cause the signal degradation, which establishes the end of useful life for the overall sensor product. They are all chronic and predictable under a first order decay function on the loss of signal amplitude.

The fluorescence from all the distortion-producing species is then:

$$[I_{distortion}] = [Ox] + [Th] + [PA] \quad (2.5)$$

where $$[Ox] = I_{0,QC}\%F_{Ox}[(1-e^{-k_{ox}t_{ox}})e^{-k_{th}t_{th}}e^{-k_{ph}t_{ph}}e^{-k_{PA}t_{PA}}][1-(T-37)c_{Ox}]$$

$$[Th] = I_{0,QC}\%F_{Th}[(1-e^{-k_{th}t_{th}})e^{-k_{ph}t_{ph}}][1-(T-37)c_{Th}]$$

$$[PA] = I_{0,QC}\%F_{PA}[(1-e^{-k_{ox}t_{ox}})e^{-k_{th}t_{th}}e^{-k_{ph}t_{ph}}(1-e^{k_{PA}t_{PA}})][1-(T-37)c_{PA}]$$

cOx, cTh and cPA are the temperature correction coefficients of [Ox], [Th] and [PA] respectively. % FOx, % FTh and % FPA are the relative quantum efficiencies. Only modulated fluorescence, I, carries glucose concentration information within the system. The effect of not removing these noise sources would compress the modulation shown in FIG. 10 (i.e., the y-axis displacement from zero to infinite glucose). The Sn equation removes or compensates distortion-inducing factors such that the processed signal is normalized and a constant value at infinite glucose concentration (Snmax—asymptote as shown in FIG. 10). The Sn equation becomes:

$$Sn = \frac{[\text{signal}]_T - z - I_{distortion}}{I_0} \quad (2.6)$$

In particular $$[\text{Signal}]_T = \text{Signal}[1+(T-37)c_z] \quad (7)$$

because the signal value, taken from the photodetector, is temperature corrected to compensate for the temperature sensitivity (cz) of the LED (excitation) light. The temperature sensor embedded inside the sensor records the temperature, T.

Besides $$I_0 = I_{0,QC}\text{GID}[1-(T+37)c_f]$$

where $$\text{GID} = e^{-k_{ox}t_{ox}}e^{-k_{th}t_{th}}e^{-k_{pb}t_{pb}}$$

I0,QC is I0 obtained from manufacturing quality control (QC). kox, kth, and kpb are rates for oxidation, thermal degradation and photo-bleaching, respectively. tox, tth and tpb are oxidation time, thermal degradation time and photo-bleaching time, respectively. cf is the temperature correction coefficient of glucose indicator. In actual execution, tpb is tracked by using the cumulative LED-On time, tox and tth are the time since the sensor is implanted. GID is the glucose indicator decay due to the superimpose of oxidation, thermal degradation and photo-bleaching. It is configured within the algorithm to kinetically track the first order decay loss of signal that occurs over time. At manufacturing when the sensor 100 is new, the distortion producing subspecies ([Ox], [Th] and [PA]) have not yet formed and contribute nothing significant to the initial signal at turn-on. Once the sensor is inserted in-vivo, the distortion producing subspecies will form progressively and the analyte monitoring system 1 may kinetically track the fluorescence from each subspecies.

At the end, then, we obtain:

$$Sn = \frac{[\text{signal}]_T - \text{Offset} * (z + [Th])}{\text{Gain} * I_{0,QC} e^{-k_{tht} th} e^{-k_{pbt} pb} [1 - (T + 37)c_f]} \quad (2.8)$$

where Offset and Gain are the two fundamental parameters tuned through calibration, using the SMBG values.

2.3.2 Interpretive Algorithm

In some embodiments, the interpretive algorithm performed by the analyte monitoring system 1 (e.g., the transmitter 101 of the analyte monitoring system 1) may be based on the first principles constant base relationship between percent modulation and glucose as shown in FIG. 10. In some embodiments, the interpretive algorithm may be based on the reaction in the equilibrium equation (2.1) and may convert Sn into glucose concentration.

The equilibrium expression defines the dissociation constant Kd as $$K_d = \frac{[\text{Indicator}][\text{Glucose}]}{[\text{Indicator\_Glucose\_Complex}]} \quad (2.9)$$

from which we can derive $$[\text{Glucose}] = K_d \frac{[\text{Indicator\_Gluclose\_Complex}]}{[\text{Indicator}]} = K_d \frac{[I\_G\_C]}{[I]} \quad (2.10)$$

Kd is constant, I_G_C and I terms must be determined from measurement. Let's define total fluorescent signal from the unbound indicator (FI) and the glucose indicator complex ($F_{I\_G\_C}$) as $$F = F_{I\_G\_C} + F_I \quad (2.11)$$

Using Beer's law:

$$F = I_e dce\phi \quad (2.12)$$

where F is fluorescence of the species, $I_e$ is excitation light, d is path length, c is concentration of fluorescer, e is molar excitation coefficient and $\phi$ is quantum efficiency. By substituting specifically for the concentration terms for each I and I_G_C, we have $$F = I_e d[I]e\phi + I_e d[I\_G\_C]e\phi \quad (2.12b)$$

that becomes $$F = I_e de(f_I q_I + f_{I\_G\_C} q_{I\_G\_C}) \quad (113)$$

by defining $$q_I = \phi_I([I] + [I\_G\_C])$$

$$q_{I\_G\_C} = \phi_{I\_G\_C}([I] + [I\_G\_C])$$

$$f_I = \frac{[I]}{[I] + [I\_G\_C]} \quad (2.14)$$

$$f_{I\_G\_C} = \frac{[I\_G\_C]}{[I] + [I\_G\_C]} \quad (2.15)$$

Since the zero glucose concentration condition is the lowest fluorescent signal value from the sensor, we define this point as Fmin:

$$F_{min} = I_e d e q_I \quad (2.16)$$

The opposite boundary condition is where glucose concentration is very high such that 99.99% of fluorescence signal is from the glucose indicator complex I_G_C and no (approaching zero) signal from unbound indicator I. At glucose saturation, the highest possible value of fluorescence is output from the sensor and defined as Fmax:

$$F_{max} = I_e d e q_{I\_G\_C} \quad (2.17)$$

By incorporating equations (2.16) and (2.17) into equation (2.13), equation (2.13) becomes $$F = F_{min} f_I + F_{max} f_{I\_G\_C} = F_{min} f_I + F_{max}(1 - f_I) \quad (2.18)$$

Therefore $$f_I = \frac{F_{max} - F}{F_{max} - F_{min}} \quad (2.19)$$

and $$f_{I\_G\_C} = 1 - f_I = \frac{F - F_{min}}{F_{max} - F_{min}} \quad (2.20)$$

Using equation (2.10), the Glucose concentration [G] is $$[G] = K_d \frac{[I\_G\_C]}{[I]} = K_d \frac{f_{I\_G\_C}}{f_I} = K_d \frac{F - F_{min}}{F_{max} - F} = K_d \frac{sn - sn_{min}}{sn_{max} - sn} \quad (2.21)$$

because Sn is the normalized fluorescence, and $Sn_{min}$ is the signal at zero glucose concentration, while $Sn_{max}$ at infinite glucose concentration. In some embodiments, during sensor manufacturing, each sensor 100 may be cycled through a computer automated quality control measurement rig, which may measure one or more parameters (e.g., one or more of $c_z$, $K_d$, $Sn_{max}$, $Z_{gel}$, and $Z_{bleed}$). In some embodiments, one or more other parameters may be developed from designed and controlled in-vitro experiments (e.g., one or more of $K_{pb}$, $K_{PA}$, $K_{th}$, $\phi_Z$, $c_f$, $c_{Th}$, $c_{Ox}$, $c_{PA}$, %$F_{Ox}$, %$F_{PA}$, and %$F_{Th}$) and in-vivo tests (e.g., $K_{Ox}$).

2.4 Real-Time Filtering

Figure 13:
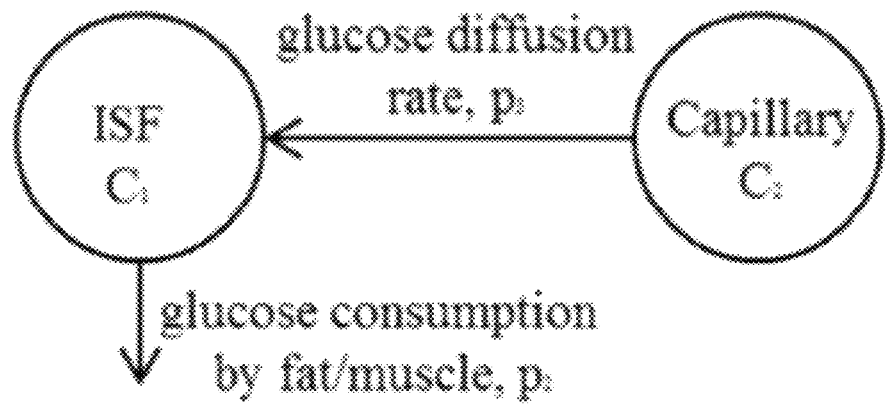
FIG. 13 illustrates the theoretical relationship between interstitial and plasma glucose according to some embodiments of the present invention.

In some embodiments, to control the propagation of noise in the sensor measurements into the glucose values, the analyte monitoring system 1 (e.g., the transmitter 101 of the analyte monitoring system 1) may use an algorithm for real-time smoothing/filtering. Based on the signal-processing algorithm aforementioned, the raw sensor measurements may be converted into corresponding glucose values perceived at the hydrogel surface of the sensor, referred to as Gel glucose, and then the glucose levels in the blood may be inferred based on an in-vivo venous-to-glucose indicator diffusion model and/or an in-vivo sensor sensitivity calibration model. Both methods used to convert Gel glucose values into corresponding blood glucose levels inherently involve the estimation of the instantaneous rate of change of values and algebraic combination of its values with their rate of change. Because estimation of the rate of change of noisy values amplifies the noise level in the Gel glucose levels, more noise in the blood glucose levels is observed, compared to the values. The severity of the noise in the blood glucose levels increases with the decrease in the signal-to-noise ratio in the Gel glucose levels. The core method for compensating noise in the sensor glucose values is to estimate smooth estimates of the instantaneous rate of change of Gel glucose, i.e., glucose perceived at the hydrogel surface of the sensor, and use those estimates of the Gel glucose rate of change to obtain the blood glucose sensor values. To obtain smooth estimates of the derivative of the Gel glucose profile as a function of time and use them for inferring blood glucose levels, the following venous-to-gel glucose diffusion/transport model, represented in FIG. 13, is used:

$$BG(t) = \tau \frac{d(Gel(t))}{dt} + (1 + c\_d\_rr) * Gel(t) \quad (2.22)$$

where BG(t) represents the blood glucose level (C1), Gel(t) represents the Gel glucose levels (C2), τ represents the diffusion time constant, and c_d_rr is the consumption to diffusion rate ratio constant, fixed equal to 0.05. The first term amplifies the noise in the Gel glucose profile because derivative of a function amplifies noise component of the function. Therefore, BG(t) appears noisier compared to the corresponding Gel(t) values.

To alleviate the noise in BG(t), the analyte monitoring system 1 may be configured to obtain smooth estimates of the derivative of Gel(t) values. In some embodiments, obtaining the smooth estimates may include one or more of:

1. Assuming Gel(t) to change linearly with time within a window of, for example, 10 min. Gel(t)=m*t+c, where m approximates the rate of change of Gel(t) and c represents the offset/intercept.

2. Computing m and c through, for example, the method of constrained least squares (CLS), i.e., solving the following optimization problem:

$$\underset{m,c}{\text{Minimize}}\left\{\sum_{i=1}^{n}(Gel(t_i) - m*t_i - c)^2 + \lambda^2*(m - \hat{m})^2\right\}$$

where $\hat{m}$ represents the slope from the previous window and λ represents the degree to which the slope from the current window is desired to be close to the slope from the previous window. As λ increases, smoothness is imparted to the BG(t); however, an increase in the noise level in the BG(t) estimate is seen, at the expense of delay/lag in the profile and vice-versa. The solution of this equation has a closed-form, analytical expression, and the value of m and c obtained from it can be used to calculate BG(t).

The CLS method to obtain the rate of the change of Gel(t) is implemented and embedded in the transmitter 101, and works in the following way. Let $\{t_i, Gel(t_i)\}$, i=1, 2, . . . , n, represent n pairs of time points and corresponding Gel glucose values in a 10-min window into the past. To avoid numerical, round-off errors in the calculations, the time stamps are normalized as $\hat{t}_i = t_i - t_1$. Then m and c are given by the following expressions:

$$c = \frac{\left(\sum_{i=1}^{n}\hat{t}_i^2 + \lambda^2\right)*\sum_{i=1}^{n}Gel(t_i) - \left(\sum_{i=1}^{n}\hat{t}_i\right)*\left(\sum_{i=1}^{n}Gel(t_i)*\hat{t}_i + \lambda^2*\hat{m}\right)}{n*\left(\sum_{i=1}^{n}\hat{t}_i^2 + \lambda^2\right) - \left(\sum_{i=1}^{n}\hat{t}_i\right)}$$

$$m = \frac{n*\left(\sum_{i=1}^{n}Gel(t_i)*\hat{t}_i + \lambda^2*\hat{m}\right) - \left(\sum_{i=1}^{n}\hat{t}_i\right)*\sum_{i=1}^{n}Gel(t_i)}{n*\left(\sum_{i=1}^{n}\hat{t}_i^2 + \lambda^2\right) - \left(\sum_{i=1}^{n}\hat{t}_i\right)}$$

Here, λ is a positive real number inversely proportional to the difference in time stamps of the latest sensor measurement with the most recent time stamp when the rate of change of Gel glucose was computed.

In summary, to obtain smooth estimates of the rate of change, the analyte monitoring system 1 may assume the Gel glucose to vary linearly in a time window (e.g., a 10-min time window). The analyte monitoring system 1 may be configured to obtain slope of the line fit using, for example, a constrained least squares method. In some embodiments, the constraints may be placed on the estimates of slope so that the slope for the current time window lies close to the slope estimated from the previous window and the degree of closeness is inversely proportional to the time interval between two consecutive windows.

The accuracy of this technique were evaluated with a mean MARD of 13.2±0.7%, and a mean MAD of 15.3±0.9 mg/dl. The evaluation of the accuracy of the sensor glucose to the gold-standard reference measurements of the blood glucose is obtained using the two different metrics aforementioned, the Mean Absolute Relative Difference (MARD) and the Mean Absolute Difference (MAD). The accuracy describes the closeness of a measurement to the true value. If glucose concentration is greater than 75 mg/dl, MARD is defined as:

$$MARD = \left(\left(\sum_{i}^{n}\frac{|[Glucose]_{SENSOR} - [Glucose]_{REFERENCE}|}{[Glucose]_{REFERENCE}}\right)/n\right)*100 \quad (2.23)$$

Otherwise, if glucose concentration is less than 75 mg/dl, MAD is defined as:

$$MAD = (\Sigma_1^n |[Glucose]_{SENSOR} - [Glucose]_{REFERENCE}|)/n \quad (2.24)$$

2.5 Glucose Transients

FIGS. 14-17 illustrate some glucose transients of a representative sensor (S23814) during four different time periods. In FIGS. 14-17, the sensor glucose measurements are shown with a solid line; the lab reference values (YSI), with which the accuracy is calculated are shown with circles; and the SMBG (Finger Sticks), which were used to calibrate the system, are shown with pluses (i.e., +s).

Figure 14:
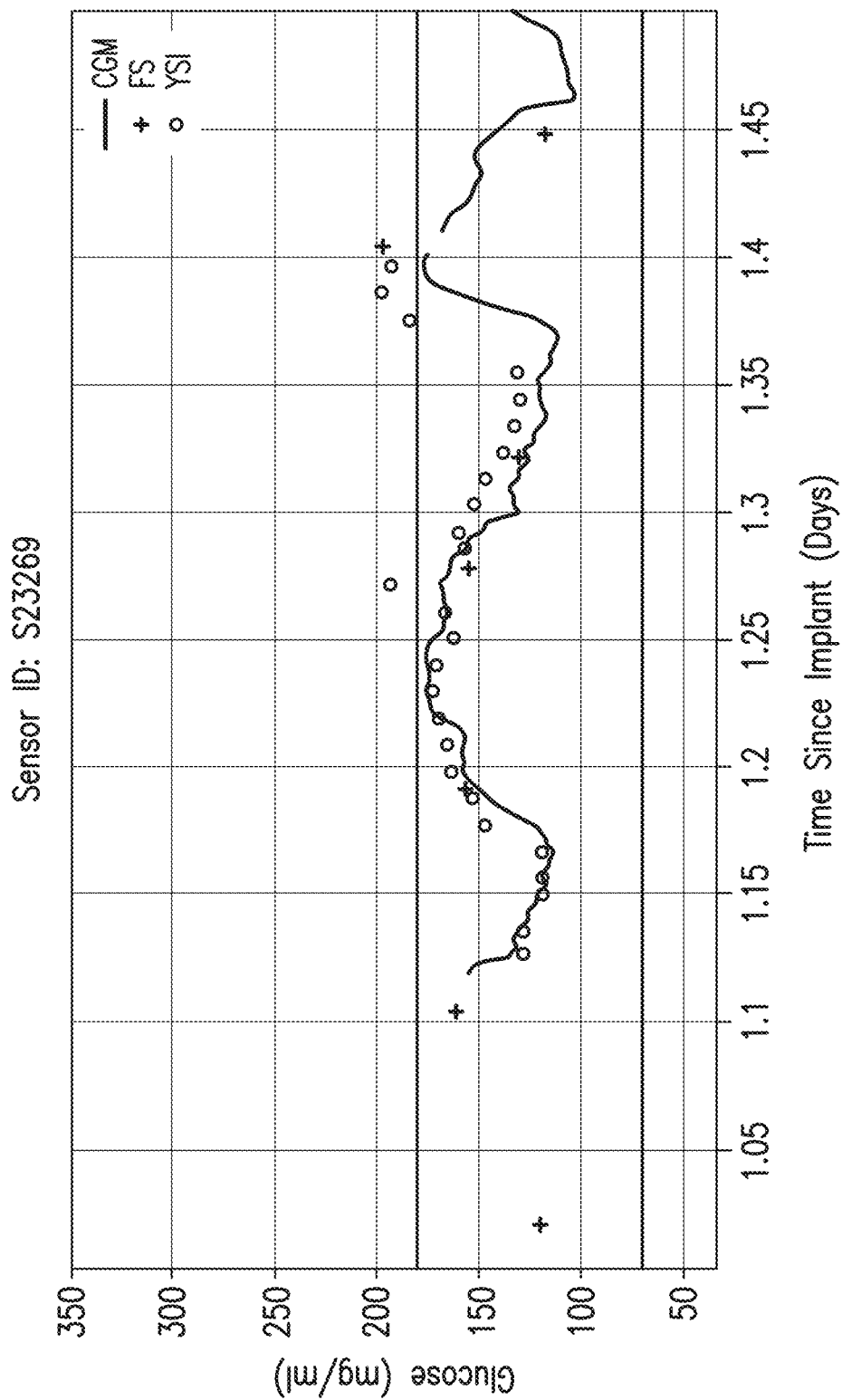
FIGS. 14-17 illustrate CGM data, YSI values, and the Finger Stick (FS) measurements of a representative sensor embodying aspects of the present invention during different time periods.

FIGS. 14-17 show a good overlap between the calculated glucose and the reference data, and consequently a quite good accuracy of the system. As shown in FIG. 14, at the beginning of the first day, there are no CGM measures because the system has still to be calibrated. However, the calculated glucose is noisy, and, as clearly seen in FIG. 15, there is an offset between the CGM data and the reference measures: this is one of the main issues that worsen the system accuracy.

2.6 Trend Value and Prediction Alarms

Trend values, also known as Rate Of Change (ROC), and/or prediction alarms may be used by patients with diabetes who use CGM to manage their blood glucose, to avoid hypo- and hyper-glycemia events, for example. In some embodiments, the analyte monitoring system 1 may be configured to calculate one or more trend values using an algorithm that strikes a balance between the noise sensitivity in the instantaneous trend and the delay imbedded in the average trend. In some embodiments, a more accurate trend may lead to a better performance in prediction alarms. In some embodiments, the analyte monitoring system 1 (e.g., the transmitter 101 of the analyte monitoring system 1) may employ a straightforward approach for estimating the trend value and predicted glucose to meet the visual expectation of the users and/or obtain a good accuracy against the reference measures. Specifically, in some non-limiting embodiments, the trend value may be calculated as the linear slope of the finite CGM glucose in a time period (e.g., the past 16 min). In some embodiments, at time stamp tn, BGn−N, . . . , BGn−1, BGn may be assumed as the CGM glucose in the past minutes and tn−N, . . . , tn−1, tn are the corresponding time stamps. Therefore, the trend value ROCn at time stamp tn, may be calculated, for example, as below through ordinary least squares:

$$y = \beta X + \varepsilon \quad (2.25)$$

where $$y = \begin{bmatrix} BG_{n-N} \\ \vdots \\ BG_{n-1} \\ BG_n \end{bmatrix}, X = \begin{bmatrix} 1 & t_{n-N} \\ \vdots & \vdots \\ 1 & t_{n-1} \\ 1 & t_n \end{bmatrix}, \beta = \begin{bmatrix} \beta_1 \\ \beta_2 \end{bmatrix}, \varepsilon = \begin{bmatrix} \varepsilon_{n-N} \\ \vdots \\ \varepsilon_{n-1} \\ \varepsilon_n \end{bmatrix} \quad (2.26)$$

and therefore, $$\beta = (X^T X)^{-1} X^T y \quad (2.27)$$

$$ROC_n = \beta_2 \quad (2.28)$$

Note that ROCn is calculated only when N≥2, i.e., with at least three finite CGM glucose readings in the past 16 min. Otherwise, ROCn is deemed to be NaN (not a number). In addition, in some embodiments, when the absolute trend value is greater than 1 mg/dl/min, the trend value may be accepted only when the coefficient of determination is greater than a prefixed parameter (e.g., equal to 0.8). Otherwise, ROCn may be deemed to be NaN, and then trend may temporarily not be displayed to the subject. Instead, the predicted glucose may be calculated through linear projection. For example, CGM glucose at time stamp PH (Prediction Horizon) min after tn may be calculated as $$BG_{n+PH} = BG_n + ROC_n * PH \quad (229)$$

The trend values may be evaluated by comparing them with lab reference (Hexokinase) rate of change (ROC), evaluating the concurrence of CGM and Hexokinase ROC (see FIG. 18).

The predication alarms may be evaluated by calculating the mean absolute relative difference (MARD) between the measured CGM blood glucose and a time period ahead (e.g., 20-min-ahead) prediction, with a result of 9.95%.

2.7 Algorithmic Issues and Improvements

In some embodiments, one or more algorithms performed by the analyte monitoring system 1 (e.g., by the transmitter 101 of the analyte monitoring system 1) may have one or more of an improved calibration algorithm, improved accuracy, an improved denoise algorithm, and improved prediction. In some embodiments, the analyte monitoring system 1 may additionally or alternatively may be configured for improved handling of missing values, which the analyte monitoring system 1 (e.g., the transmitter 101 of the analyte monitoring system 1) may save as NaN (Not A Number).

2.8 Aim of the Application

Some embodiments may be applied to an analyte monitoring system 1 having one or more of CGM data that noisy and/or contains a large number of missing values (identified as NaN) (e.g., due to transmitter 101 charging). In some embodiments, the analyte monitoring system 1 (e.g., the transmitter 101 of the analyte monitoring system 1) may calculate the trend value simply as the linear slope of the finite CGM glucose in a past time period (e.g., the past 16 min) through, for example and without limitation, ordinary least squares and/or the analyte monitoring system 1 may generate one or more alarms based on the predicted glucose that is calculated through linear projection.

In some embodiments, the analyte monitoring system 1 may use one or more digital filtering techniques (e.g., Kalman Filter) to enhance the quality of the signal and reduce the random noise component of the error. In some non-limiting embodiments, to reduce the noise and compensate for the presence of missing values, the analyte monitoring system 1 may apply an on-line Kalman Filter (KF). In some embodiments, the analyte monitoring system 1 may adjust one or more unknown parameters of the KF (e.g., by a stochastically based smoothing criterion exploiting data of a burn-in interval). In some embodiments, the analyte monitoring system 1 may employ one or more methods (e.g., based on one or more of polynomial or autoregressive time-series models, Kalman filtering, and artificial neural networks) to predict (e.g., 5, 10, 15, 20, 25, 30, 35, or 45 min ahead of time) glucose concentration from past CGM data (possibly weighted via a forgetting factor [μ]). To improve the prediction performance of the analyte monitoring system 1, the analyte monitoring system 1 may use one or more prediction models, such as, for example and without limitation, polynomial or autoregressive.

In some embodiments, the analyte monitoring system 1 may use one or more of the algorithms in a real-time environment. That is, in some embodiments, the algorithms performed by the analyte monitoring system 1 can be implemented and embedded directly in the transmitter 101.

3. Database 3.1 PRECISE Study

The dataset used in the analyses is made up of 44 T1D subjects, of different nationalities, that will be used for the CE approval. CGM was performed using an analyte monitoring system 1 while, in parallel, a time-series of blood glucose references was measured using the YSI laboratory apparatus (Yellow Springs Instruments, Yellow Spring, Ohio). For the sensor calibration, every day, the subject had inserted, in the hand held application, some SMBG values. The study was designed to provide an at-home performance evaluation of the investigational CGM system. An institutional review board approved the protocol, and all study procedures were conducted in accordance with the principles of the Helsinki Declaration and current guidelines for Good Clinical Practice. Written informed consent was obtained from all subjects before study enrollment. The prospective, single-arm multi-center investigation consists in at least 3 months data, where two sensors were inserted bilateral in the upper arms of the patients, which were requested to perform a calibration through SMBG twice a day. There were 10 in-clinic procedural visits over 6 months: an insertion visit, three 8-hour day visits, five 24-hour visits and a removal visit. Regarding the home wear, the subjects had to wear a transmitter 101 over the primary sensor at all times for data collection. Note that the CGM data of primary sensor was available to the patient throughout the study.

Figure 19:
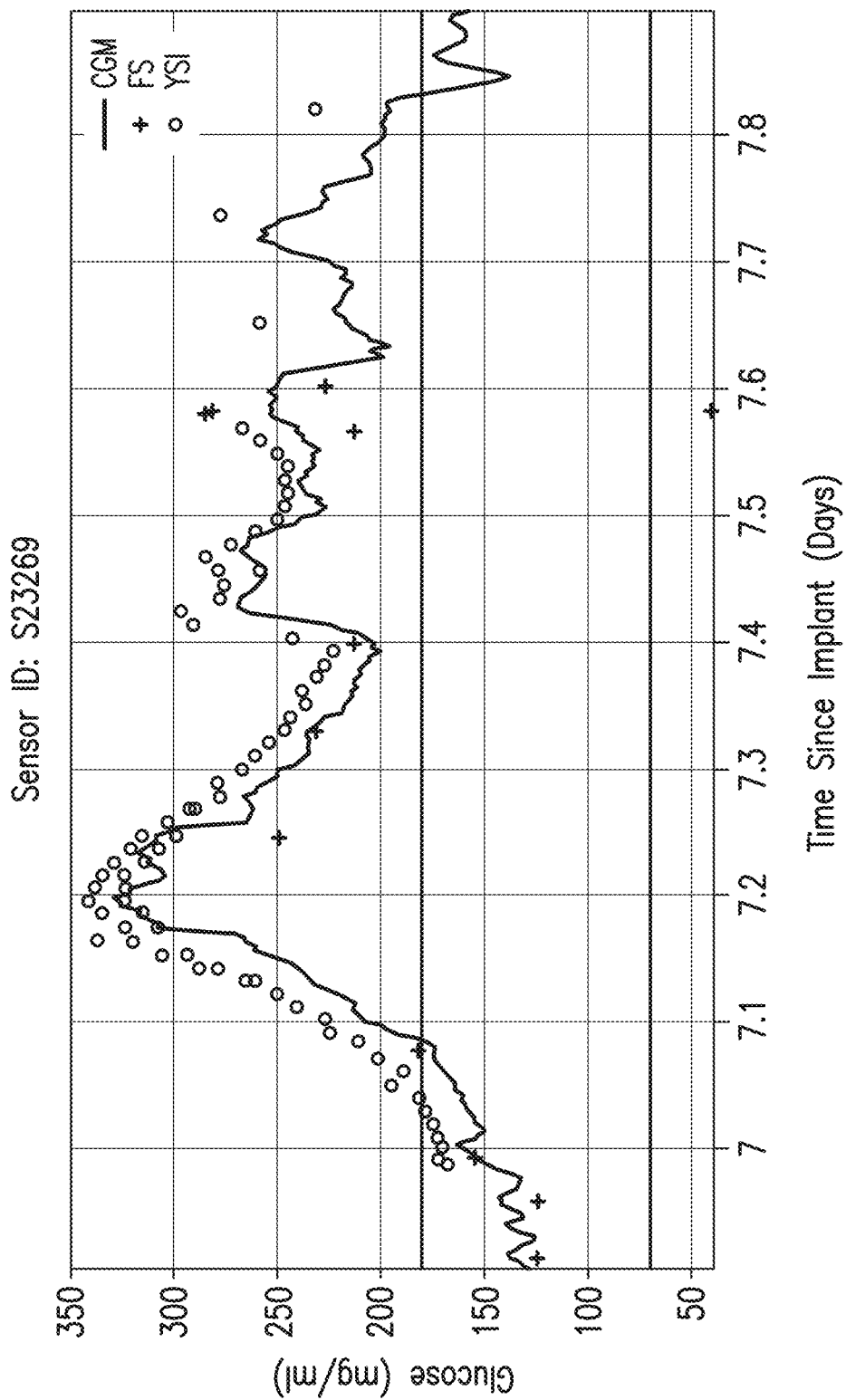
FIG. 19 illustrates a representative sensor in Dataset 2. The CGM data is shown with a solid line, the YSI values are shown with circles, and the Finger Sticks (FS) measurements are shown with +s.
Figure 21A:
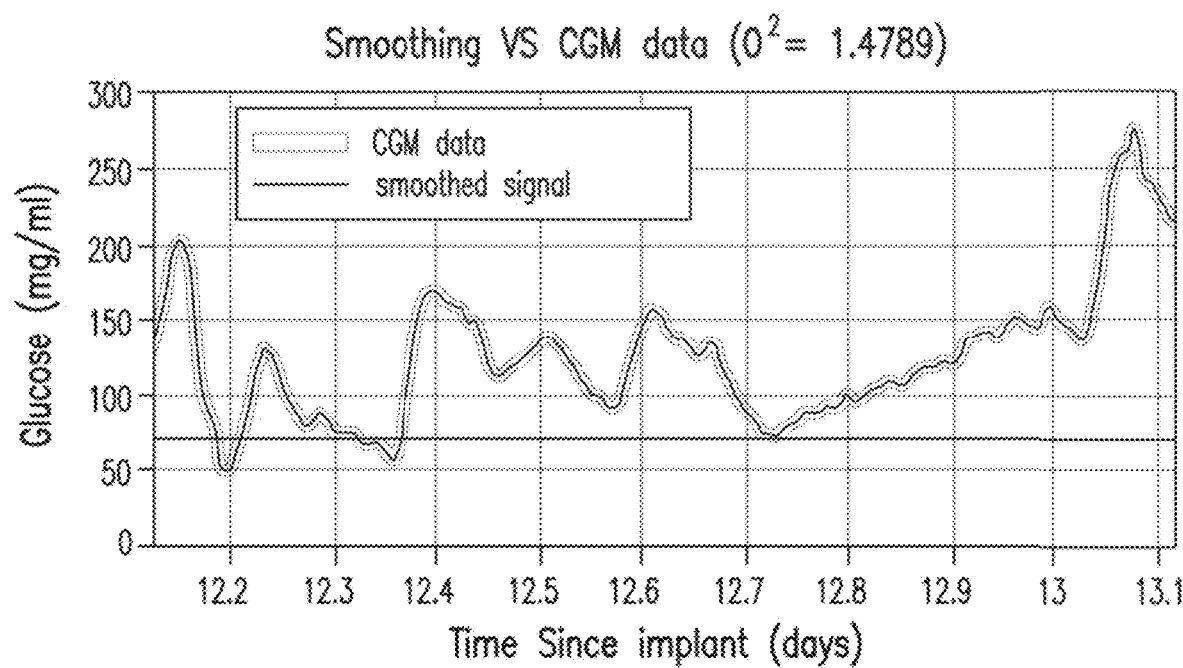
FIGS. 21A-21D are graphs illustrating CGM data (thick line) versus smoothed signal (thin line) during a first time window, weighted residuals (circles) during the first time window, CGM data (thick line) versus smoothed signal (thin line) during a second time window, and weighted residuals (circles) during the second time window, respectively, for a representative sensor.
Figure 21B:
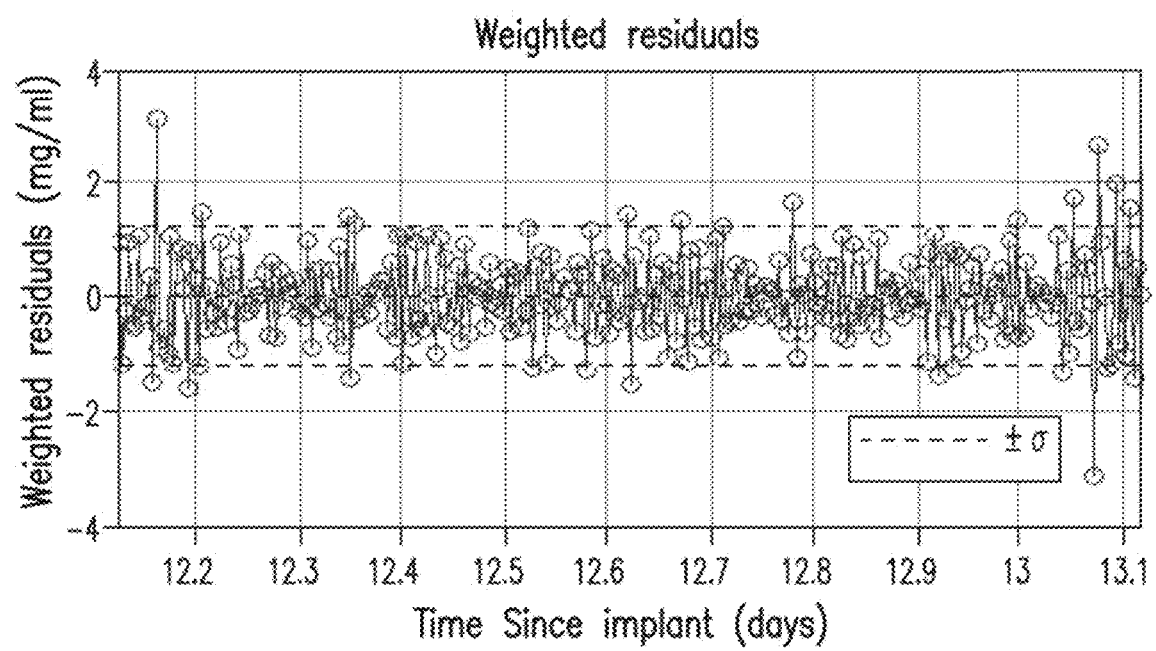
Figure 21C:
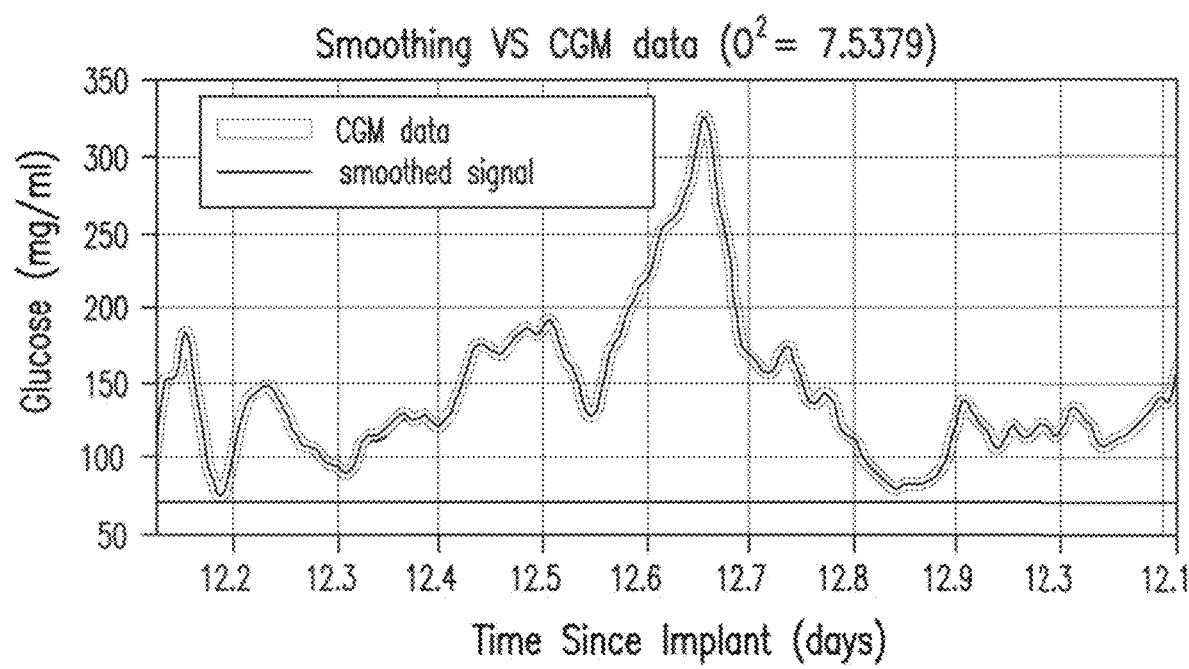
Figure 21D:
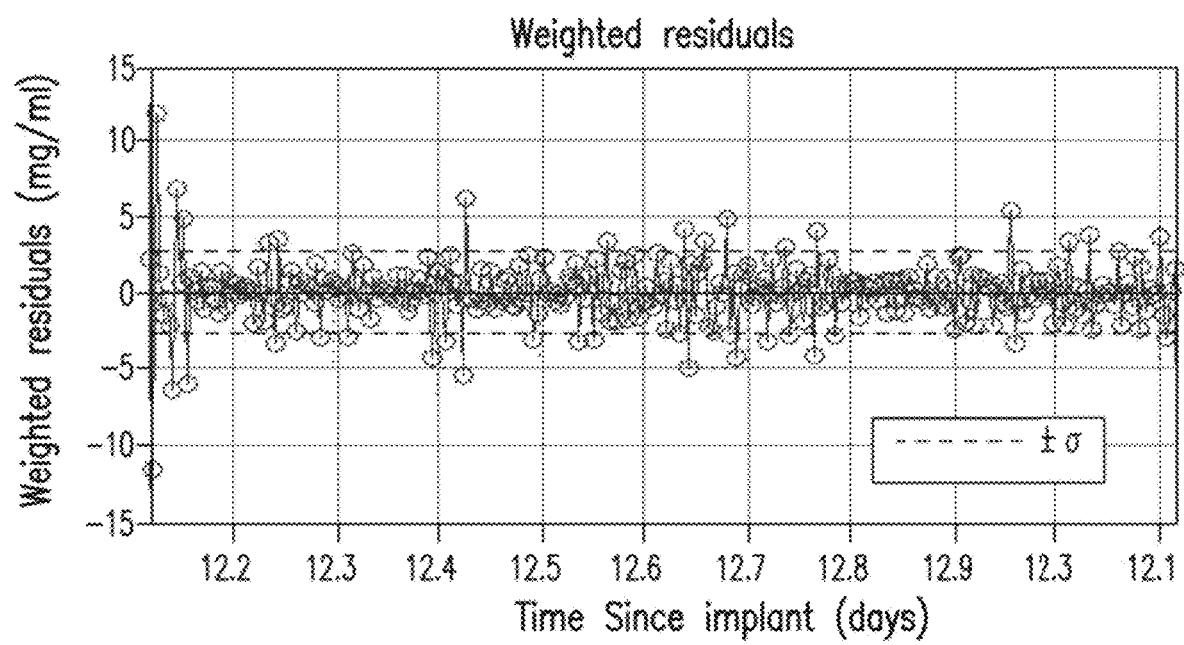

In this application, for the algorithms analyses, two different version of the same dataset have been used: the data of the 44 subjects at the interim analysis of the PRECISE study, and the same data with a new, updated software algorithm, which improved the accuracy. From now on, they will be called Dataset 1 and Dataset 2. In FIG. 19, the CGM data (solid line), the SMBG or finger stick (FS) measurements (+s) and YSI (circles) are shown for a representative sensor of Dataset 2. Comparing it with FIG. 15, we can see the better accuracy that characterizes Dataset 2.

Each sensor data consists in a complex structure containing a lot of information: patient and implantation information, calculated blood glucose, lab reference measurements with YSI, SMBG used to calibrate the system, accuracy between reference and calculated glucose concentration. The CGM readings data, in particular, is retrospectively analyzed to calculate the accuracy: with the purpose to improve it, different techniques (e.g. calibration or filtering techniques) are continuously assessed. Analyzing the data, we found that a unique clinical study design does not exist; each sensor has its own sampling grid and its own duration. FIGS. 62-65 show these and other baseline characteristics information, for both datasets. FIG. 62 shows baseline characteristics. FIG. 63 shows in-exclusive criteria. FIG. 64 shows PRECISE study Dataset 1 information. FIG. 65 shows PRECISE study Dataset 2 information.

Note that two sensors have been removed from the analyses: the sensor S8531 as it has no YSI data, while the sensor S23277 for the too high number of missing values (referred as NaN). Therefore, the different analyses have been applied to 42 patients of the database, for both datasets.

4. Denoising
4.1 Methods

Figure 15:
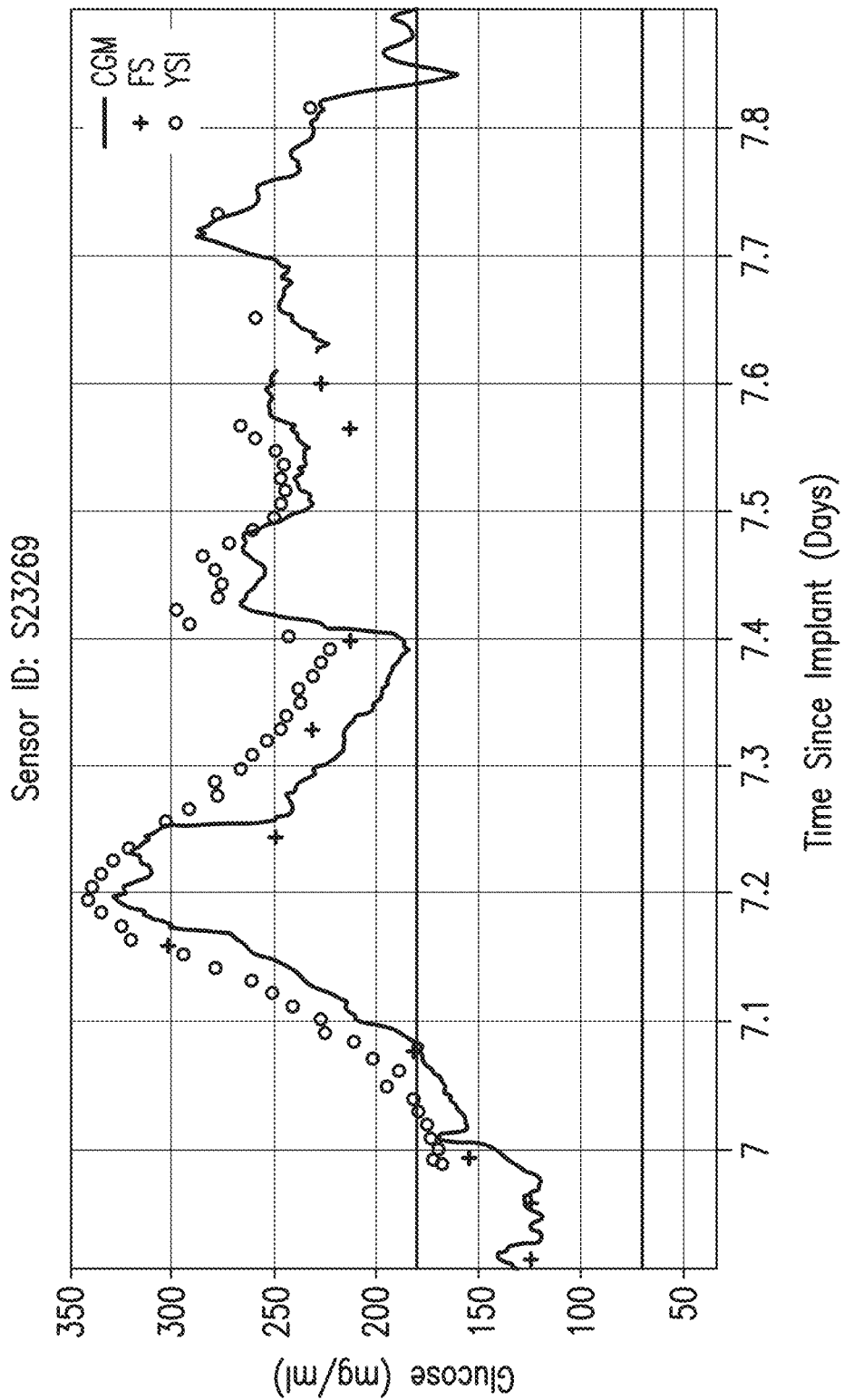
Figure 16:
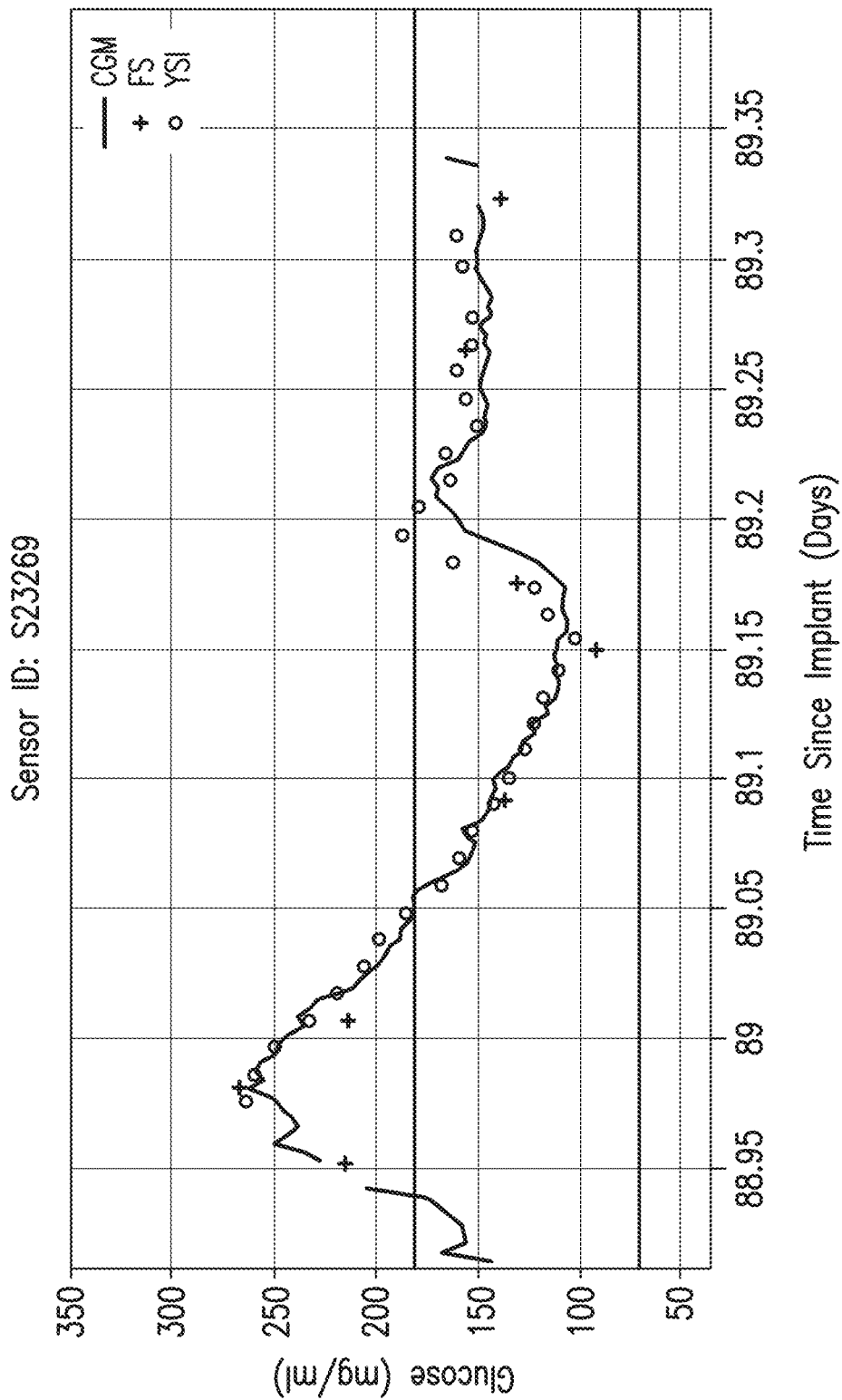
Figure 17:
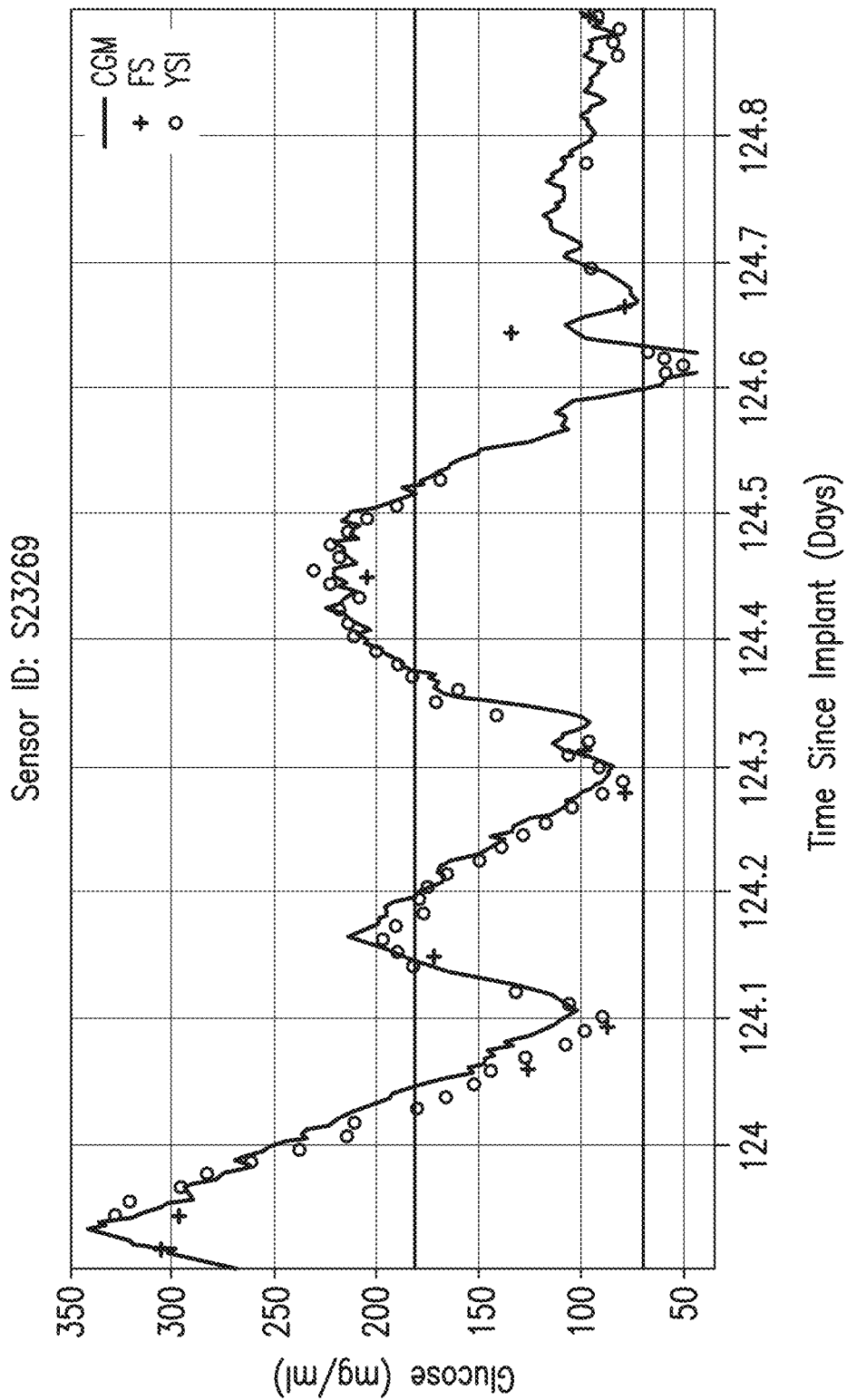

As foretold in section 2.7 and occurred in FIG. 15, several sources of error can affect the accuracy of CGM data. In particular, an error component is often present due to imperfect calibration. Another source of error (which sometimes is lumped together with the random noise component) is related to the sensor physics, chemistry, and electronics. Finally, the CGM signal is also corrupted by a random noise component, which dominates the true signal at high frequency. In more formal terms, let's consider the equation $$y(t)=u(t)+v(t) \quad (4.1)$$

where y(t) is the glucose level measured at time t, u(t) is the true, unknown, glucose level, and v(t) is the random noise affecting it, which is supposed to be additive. The purpose of filtering, at the end, is to recover u(t) from y(t). Given the expected spectral characteristics of noise, i.e., noise is white, (causal) low-pass filtering represents the most natural candidate to separate signal from noise in on-line applications. In low-pass filtering is that, since signal and noise spectra normally overlap, it is not possible to remove the random noise v(t) from the measured signal y(t) without distorting the true signal u(t). In particular, distortion results in a delay affecting the estimated i(t) with respect to the true u(t): the more the filtering, the larger the delay. It is easily understood that having a consistently delayed, even if less noisy, version of CGM data could be useless in practice, e.g., for the generation of timely hypo alerts. A clinically significant filtering issue is thus the establishment of a compromise between the regularity of i(t) and its delay with respect to the true u(t).

The data contains a large number of missing values, identified as NaN, due to transmitter 101 charging. In some embodiments, to reduce the noise and to compensate the presence of missing values, the analyte monitoring system 1 may use an approach developed within a Bayesian estimation embedding for the online denoising of CGM signals. In some embodiments, the analyte monitoring system 1 may use a KF implementation, which may exploit the key feature of incorporating a stochastically based smoothing criterion for the determination of the unknown parameters. As a result, the method may work in real-time, and it may be self-tunable. Moreover, a fast preliminary analysis has been made to assess the time-dependence of the error variance $\sigma^2$ using the same smoothing criterion. Analysis of how the error v(t) varies in one sensor 100 through the time, from the first to the last day, can become a kind of goodness metric. If the error variance grows as time passes, it may indicate a decrease in the system performance.

4.1.1 Kalman Filter

In some embodiments, the analyte monitoring system 1 (e.g., the transmitter 101 of the analyte monitoring system 1) may be configured to implement the Kalman Filter (KF), at discrete time, by first-order difference equations that recursively estimate the unknown state vector x(t) of a dynamic system exploiting vectors of noisy measurements y(t) causally related to it. The process update equation is given by $$x(t+1)=Fx(t)+w(t) \quad (4.2)$$

where x(t) has, in general, size n, w(t) is usually a zero-mean Gaussian noise vector (size n) with (unknown) covariance matrix Q (size n×n), and F is a suitable matrix (size n×n). The state vector x(t) is linked to the measurement vector y(t) (size m) by the equation $$y(t)=Hx(t)+v(t) \quad (4.3)$$

where v(t) is the zero-mean Gaussian noise measurement error vector (size m) with (unknown) covariance matrix R, and which is uncorrelated with w(t), and H is a suitable matrix (size m×n). The linear minimum variance estimate of the state vector obtainable from the measurements y(t) collected till time t is indicated by x^(t|t), and can be computed by using the following linear equations:

$$\begin{cases} K_t = (FP_{t-1|t-1}F^T + Q)H^T(H(FP_{t-1|t-1}F^T + Q)H^T + R)^{-1} & (4.4) \\ \hat{x}(t|t) = F\hat{x}(t-1|t-1) + K_t(y(t) - H\hat{x}(t-1|t-1)) \\ P_{t|t} = (1 - K_tH)(FP_{t-1|t-1}F^T + Q) \end{cases}$$

where Pt|t (size n×n) is the covariance matrix of the estimation error affecting x^(t|t), $K_t$ (size n×m) is the Kalman gain matrix, and $P_{0|0}$ and x^(0|0) are the initial conditions. The Q and R matrices, i.e., the process and the measurement noise covariance matrices (respectively), are key parameters in determining the performance of KF. Unfortunately, Q and R are in most cases (like ours) unknown.

Now, an a priori description of the unknown signal is necessary. A simple but flexible way to model a smooth signal on a uniformly spaced discrete grid is to describe it as the realization of the multiple integration of a white noise process. Our smooth signal, u(t), can be reliably described as the double integration (the so-called integrated random-walk model), so we have $$u(t)=2u(t-1)-u(t-2)+w(t) \quad (4.5)$$

where w(t) is a zero-mean Gaussian noise with (unknown) variance equal to $\lambda^2$. The choice of two integrators emerges from a number of simulation studies using a cross-validation strategy, and it was confirmed comparing the filtered signal trend using m=2 and m=3 integrators, for example. Bringing it into the state space, two state variables, i.e., $x_1(t)=u(t)$ and $x_2(t)=u(t-1)$, are needed. Then, the state-space vector at time t becomes $x(t)=[x_1(t)\ x_2(t)]^T$, and F is consequently given by $$F = \begin{bmatrix} 2 & -1 \\ 1 & 0 \end{bmatrix} \quad (4.6)$$

Because the CGM value is the only output of the system, the measurement vector y(t) becomes scalar, and H=[1 0]. For the estimation of $\hat{x}(t|t)$, $P_{t|t}$ becomes a 2×2 matrix (with $P_{0|0}=10\ I_2$ and $\hat{x}(0|0)=[y(0)\ y(-1)]^T$), Kt a 2×1 vector, and Q and R are $$Q = \begin{bmatrix} \lambda^2 & 0 \\ 0 & 0 \end{bmatrix} \quad (4.7)$$

$$R = \sigma^2$$

where $\lambda^2$ and $\sigma^2$ are unknown and must be detected from the data.

4.1.2 Maximum Likelihood Smoothing Criterion

In order to arrive at an estimate of glucose $\hat{u}(t)$, both $\lambda^2$ and $\sigma^2$ are required. In some embodiments, the analyte monitoring system 1 (e.g., the transmitter 101 of the analyte monitoring system 1) may estimate the values of one or more of $\lambda^2$ and $\sigma^2$ in real-time from the data. In some embodiments, these parameters may be retrospectively tuned (e.g., following the Tikhonov regularization approach).

In some embodiments, the analyte monitoring system 1 (e.g., the transmitter 101 of the analyte monitoring system 1) may consider a portion (e.g., a 6-h window) of each time-series is considered as a tuning interval, where the unknown parameters $\lambda^2$ and $\sigma^2$ may be automatically estimated using a stochastically based smoothing criterion based on maximum likelihood (ML2). Briefly, approaching the problem of smoothing the data of the tuning interval in vector y (in this case y contains all the measurement collected in the 6-h period) as a linear minimum variance estimation problem, one has to solve $$\hat{u} = \underset{u}{\operatorname{argmin}} \left\{ (y-u)^T (y-u) + \left( \frac{\sigma^2}{\lambda^2} \right) u^T L^T L u \right\} \quad (4.8)$$

where the first term of the cost function on the right-hand side measures the fidelity to the data, while the second term weights the roughness of the estimate, L being square of lower triangular Toeplitz matrix whose first column is [1, −2, 1, 0, . . . . . , 0]$^T$. When both $\lambda^2$ and $\sigma^2$ are unknown, the minimization problem should be solved for several trial values of the regularization parameter $\gamma=\sigma^2/\lambda^2$ until $$\frac{WRSS(\gamma)}{n - q(\gamma)} = \gamma \frac{WESS(\gamma)}{q(\gamma)} \quad (4.9)$$

where WRSS=$(y-\hat{u})^T(y-\hat{u})$, WESS=$\hat{u}^T L^T L \hat{u}$, $q(\gamma)$-trace $(I_k+\gamma L^T L)-1$, $I_k$ is k-size identity matrix, and k being the number of measured CGM samples in the selected window (here 6 h). As $\gamma$ is determined, the estimate of $\sigma^2$ is given by $$\hat{\sigma}^2 = \frac{WRSS(\gamma)}{n - q(\gamma)} \quad (4.10)$$

In some embodiments, the analyte monitoring system 1 (e.g., the transmitter 101 of the analyte monitoring system 1) may find the values of $\lambda^2$ and $\sigma^2$ and use them to allow both real-time application of KF and individualization of KF parameters. As we have seen, "universal" $\lambda^2$ and $\sigma^2$ estimates cannot be used for all individuals. Instead, their values need to be individualized, calling for a real-time and self-tunable parameter-estimation procedure in order to make KF really online applicable.

Note that one of the hypotheses to use that method is the signal causality. Since it is not, an artifice to manage the non-zero initial condition is used: in particular a fictitious burnin interval is used.

4.2 Implementation 4.2.1 Error Variance Analysis

In some embodiments, after loading the data, the CGM measurement is extracted from the structures. A time window, as large as possible of almost a day, is considered: that window doesn't contain any NaN values, allowing the future analysis. The u estimate, the smooth signal wanted, may be calculated on a virtual grid, thicker than the CGM signal one (i.e. every minute). Here, the hypothesis that v(t), the zero-mean Gaussian noise measurement error vector, has a constant SD (standard deviation) has been made, i.e. its covariance matrix results to be R=$\sigma^2$B, where B is a size m "ones" vector. Besides, to manage the nonzero initial condition, a fictitious burn-in interval is added to the virtual grid: here, the signal is assumed to be identically zero. Now, $\sigma^2$ is automatically estimated using the stochastically based smoothing criterion based on maximum likelihood (ML2), aforementioned. In some embodiments, an analyte monitoring system 1 estimates the error variance estimate ($\hat{\sigma}^2$) day-by-day. In some embodiments, an analyte monitoring system 1 for each patient estimates the error variance estimate ($\hat{\sigma}^2$) day-by-day for each of the 42 patients considered.

In some embodiments, with respect to missing values, the analyte monitoring system 1 may take care to evaluate the parameters in a time window without NaN. For that reason, in some embodiments, the suitable valuations are less than the number of total days of each patient. As results, the parameters mean value is calculated, and some plots generated.

4.2.2 Kalman Filtering

In some embodiments, after loading the data, the analyte monitoring system 1 may extract the various series, i.e. CGM, YSI and FS (SMBG), from the structures. In some embodiments, starting from the 2nd day, the analyte monitoring system 1 may use a KF to filter and fill the CGM data, using the $\lambda^2$ and $\sigma^2$ estimated, for example and without limitation, every 0.1 days (i.e., 144 mins). The choice to start from the 2nd day has been taken because the smoothing algorithm may need previous data to estimate the necessary parameters. In some embodiments, the time window considered doesn't contain any NaN values, and the analyte monitoring system 1 estimates $\lambda^2$ and $\sigma^2$ using previous data (e.g., the previous 6 hours of data) with, for example and without limitation, the ML2 smoothing criterion described. In some embodiments, regarding the Bayesian smoothing, the same hypotheses and choices are made, i.e. virtual grid, constant SD and fictitious burn-in interval. The analyte monitoring system 1 may use the parameters found to allow the data filtering with the KF.

To assess the quality of the denoising, different techniques have been used, in addition to plots generation. Because the YSI and FS measurements are less than the CGM ones, the comparison between these signals is allowed through matching: CGM data, filtered and not, that are not associated to reference value is eliminated. The accuracy between the reference YSI values, the SMBG measurements and the smoothed signal is estimated through the MARD and MAD calculation. Then, the ROC accuracy has been estimated, using the past 20 minutes data, comparing the signal, filtered and not, with lab reference rate of change, i.e. evaluating the concurrence of the two CGM series and YSI trend. To assess the performance, besides, three other metrics have been used: RMSE, ESOD and SRG. Furthermore, a time lag estimate was calculated as the cross correlation between the smoothed signal and the original one. The delay is the lag, used to calculate the cross-correlation, which maximize it.

Regarding the NaN, as said, the time window used to estimate the parameters may be found in order not to have any missing value. For the KF initial condition, $\hat{x}(0|0)$ cannot contain a NaN value: the closer acceptable measurements are used. The series' first value has been sought to be not a NaN. In some embodiments, the KF algorithm may be divided into two parts, i.e. predictive and corrective. The first predicts the output using the system state, while the second corrects the prediction using the measured value. When this value is missing, the algorithm uses only the predictive part, returning a numerical value instead of a NaN. Regarding the results, the matched signals, with no missing values, have been used for the calculation of the metrics of accuracy (MARD, MAD, and ROC), for the RMSE assessment and for the time lag calculation. As for the ESOD evaluation, instead, the missing values have been set to zero. To confirm the choice and goodness of time-varying parameters, two other KFs have been used and assessed on the entire dataset, this time using fixed R and Q: they have been defined either with global $\lambda^2$ and $\sigma^2$, the average across all sensors calculated in the previous phase, or with sensor individualized parameters.

4.2.3 Metrics

The evaluation of the accuracy (i.e., the closeness of a measurement to the true value) may be obtained using two different metrics: the Mean Absolute Relative Difference (MARD) and the Mean Absolute Difference (MAD). The definition of MARD and MAD can be found in equations (2.23) and (2.24). To assess the quality, three other metrics have been used: RMSE, ESOD and SRG. The Root Mean Squared Error (RMSE) is a frequently used measure of the differences between values (sample and population values) predicted by a model or an estimator and the values actually observed. It is defined as $$RMSE = \sqrt{\frac{\sum_{t=1}^{N} (\widehat{CGM}_t - CGM_t)^2}{N}}$$

where $CGM_t$ and $\widehat{CGM}_t$ are, respectively, the original and the filtered time-series of length N. The Energy of the Second-Order Differences (ESOD) quantifies the regularity of a time-series: the larger the ESOD, the less smooth the time-series. It is defined as $$ESOD(X) = \sum_{t=1}^{N} (\Delta^2(X_t))^2 = \sum_{t=3}^{N} (X_t - 2X_{t-1} + X_{t-2})^2$$

The Smoothness Relative Gain (SRG) is an index, which varies between 0 and 1, that measures the relative amount of signal regularity introduced by filtering:

$$SRG = \frac{ESOD(y) - ESOD(\hat{u})}{ESOD(y)}$$

The performance has been also assessed calculating the time lag between the CGM series and the filtered one. An average delay is estimated using the cross-correlation: the time lag is calculated as the cross correlation between the signal and its smoothed version. The lag corresponding to the peak of the cross-correlation function provides an accurate estimate of the time lag.

It must be noted that all analyses are repeated for both dataset. In particular, then, note that the analysis of the sensor S8870 in Dataset 2 is performed starting from the $3^{rd}$ day, because of the too high number of NaN values.

4.3 Results

4.3.1 Dataset 1

For the preliminary error variance analysis, following are the mean and the standard deviation of the estimated parameters: $\sigma^2=11.07\pm25.94$ (mg$^2$/ml$^2$), $\gamma=78.68\pm263.94$, $\lambda^2=0.16\pm0.1$ (mg$^2$/ml$^2$). FIGS. 20A-20C show how the error variance changes through the time. In particular, FIGS. 20A-20C show the error variance trends of three sensors. In FIGS. 20A-20C, the line with circles represents the estimated $\sigma^2$, the thick line represents the global mean error variance, and the thin line represents the sensor mean value. The sensors S8589 (FIG. 20A), S8623 (FIG. 20B), and S8703 (FIG. 20C) represent three different cases: a practically constant error variance (but one spike), a growing error variance, and a random through time error variance, respectively. FIGS. 21A-21D are graphs illustrating CGM data (thick line) versus smoothed signal (thin line) during a first time window, weighted residuals (circles) during the first time window, CGM data (thick line) versus smoothed signal (thin line) during a second time window, and weighted residuals (circles) during the second time window, respectively, for the sensor S23269. To assess the Bayesian smoothing, as shown in FIGS. 21A-21D, we can do a comparison between the sensor S23269 CGM data and the smoothed signal in the two different time windows, also with the respective weighted residuals trend in the +a (error standard deviation) band.

Figure 23A:
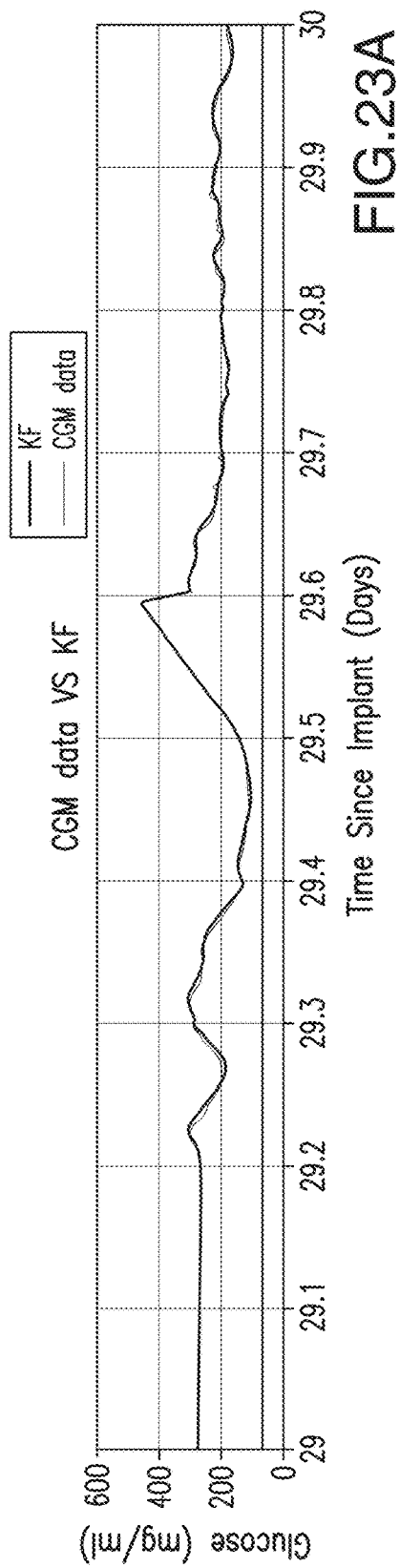
FIGS. 23A-23C are graphs illustrating CGM data (thin line) versus KF series (thick line) for a representative sensor during first, second, and third time periods, respectively.
Figure 23B:
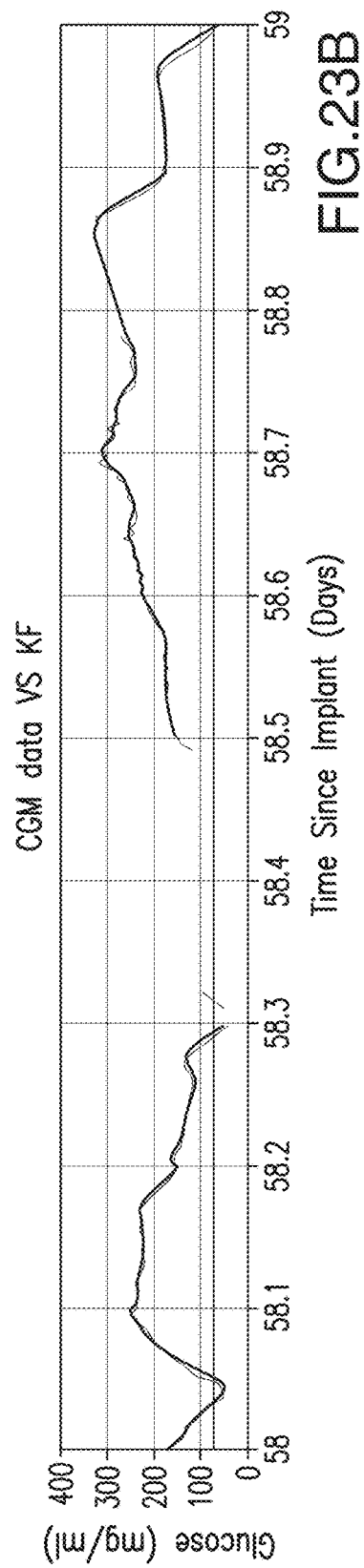
Figure 23C:
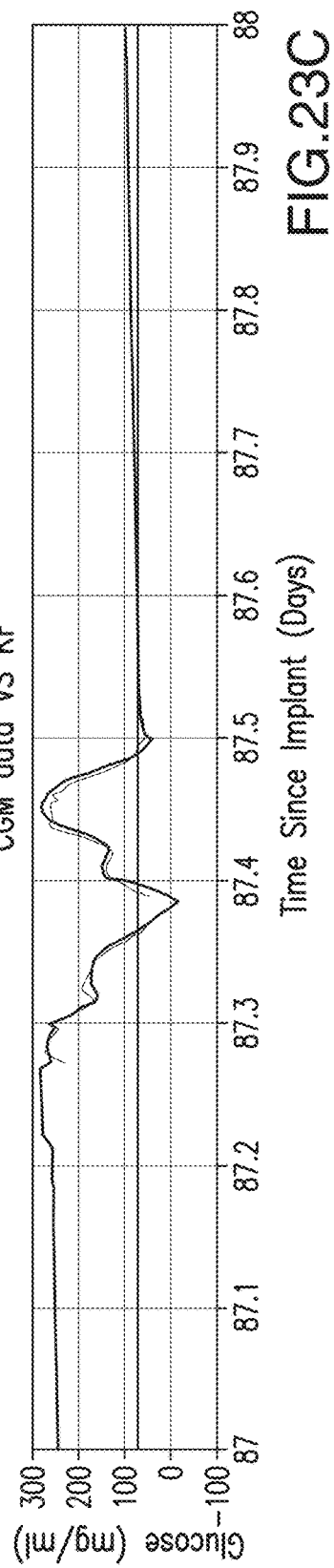
Figure 24A:
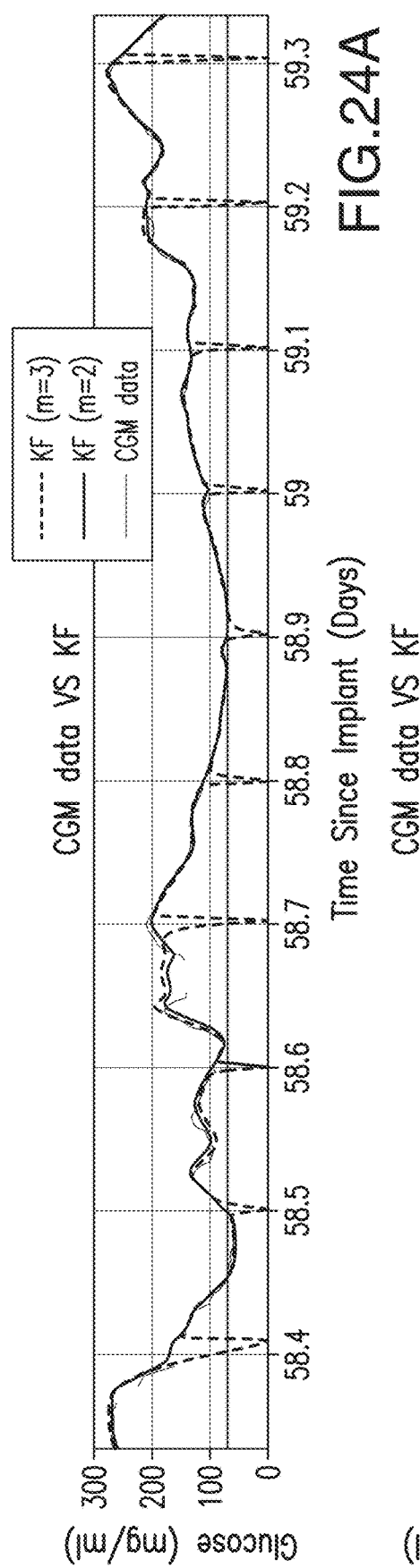
FIGS. 24A-24C are graphs illustrating KF series with m=2 (thick line) or m=3 (dashed line) integrators versus CGM data (thin line) for a representative sensor during first, second, and third time windows, respectively.
Figure 24B:
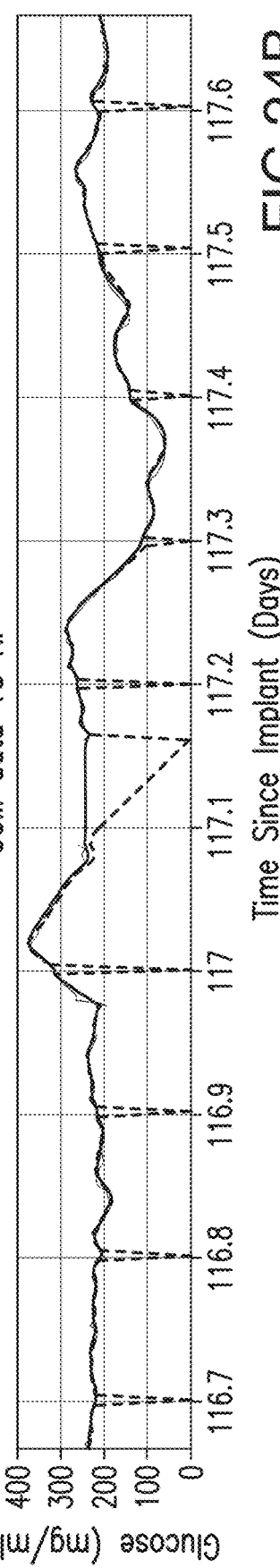
Figure 24C:
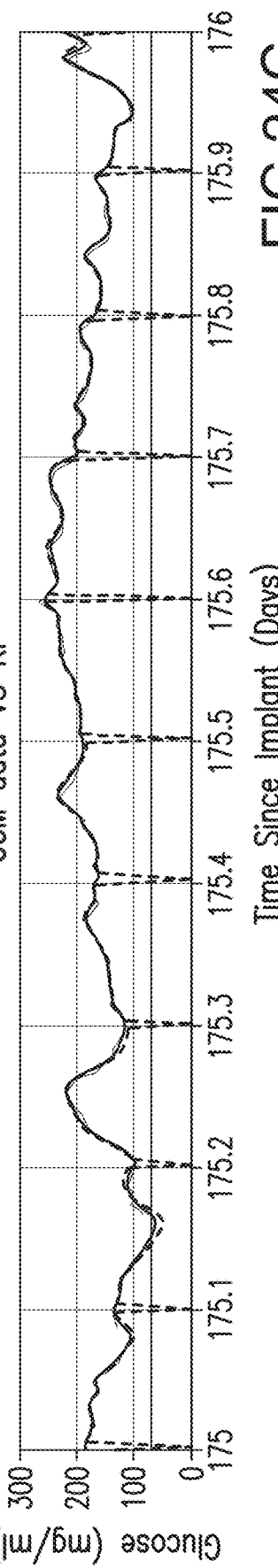

Regarding the KF assessment, FIGS. 22A-22C are graphs illustrating the CGM data (thin line) and the filtered and filled version (thick line) of sensor S23269 in three different time windows. FIGS. 23A-23C are graphs illustrating the CGM data (thin line) and the filtered and filled version (thick line) of sensor S89652 in three different time windows. FIGS. 24A-24C show KF series with an m=2 integrator (thick line), KF series with an m=3 integrator (dashed line), and CGM data (thin line) in the three different time windows. The choice of two integrators in the KF is confirmed in FIGS. 24A-24C by comparing the filtered signal trends using the m=2 and m=3 integrators. Regarding Q and R definition, FIGS. 25A-25C are graphs showing a KF with time-varying parameters (thick line), a KF with global parameters (thick dashed line), and a KF with sensor individualized parameters (thin dashed line) along with CGM data (thin line). FIG. 26 is a table showing the assessment of the accuracy performance. In FIG. 26, the MARD and MAD metrics have been calculated between the YSI values or the FS measurements and the CGM signals including the raw (i.e., not filtered) CGM series and the three filtered CGM versions using one of time-varying, global, or sensor individualized parameters. FIG. 27 is a table showing the regularity metrics and the time lag, calculated between the raw CGM signal and the three filtered CGM series. FIG. 28 is a table showing chosen m=2 and time-varying parameters and the ROC accuracy, calculated through the concurrence of the raw CGM series and the YSI trend. FIG. 29 is a table showing chosen m=2 and time-varying parameters and the ROC accuracy, calculated through the concurrence of the filtered CGM series and the YSI trend.

4.3.2 Dataset 2

Figure 30A:
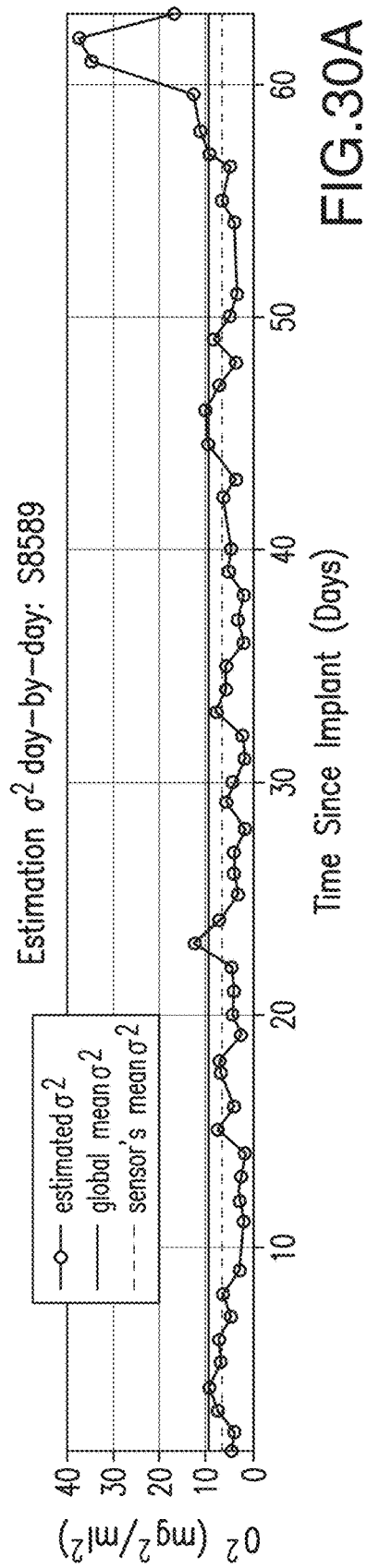
FIGS. 30A-30C are graphs illustrating estimated error variance day-by-day (line with circles) with sensor's mean (dashed line) and global mean error variance (solid line), for three different sensors.
Figure 30B:
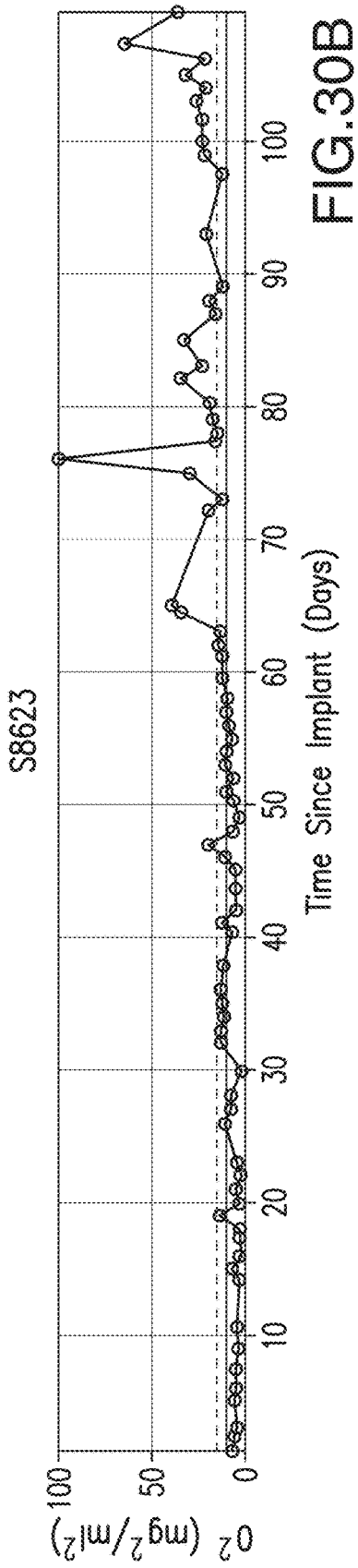
Figure 30C:
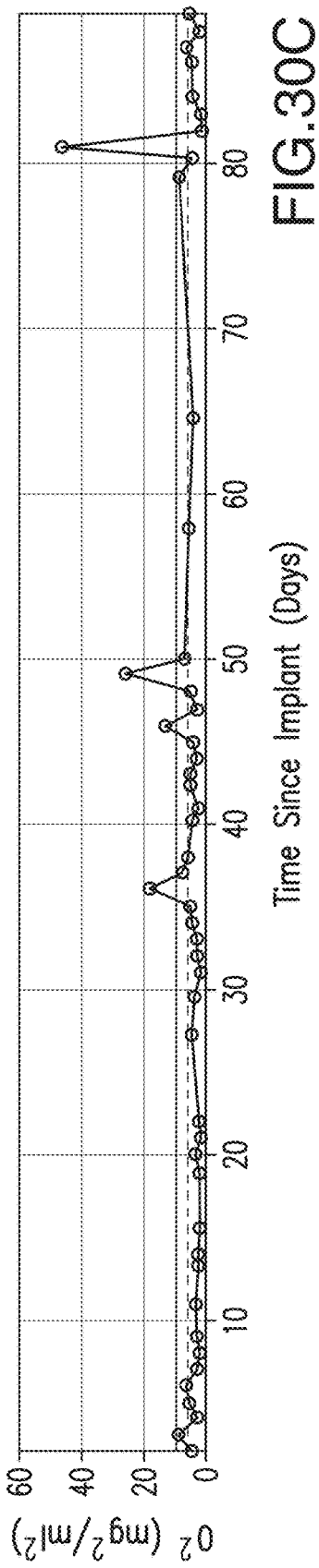
Figure 31A:
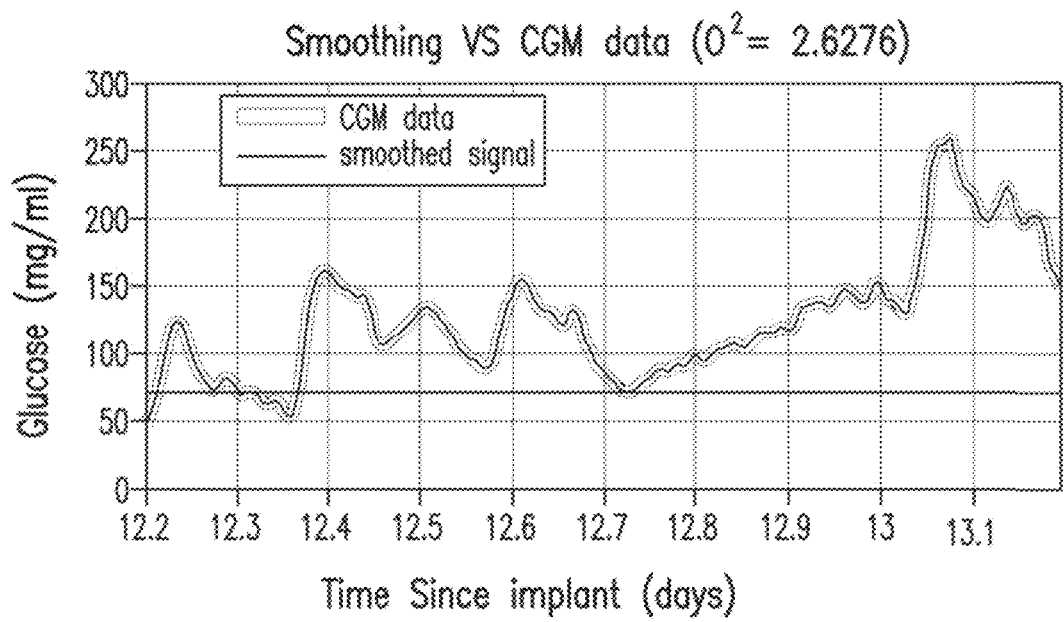
FIGS. 31A-31D are graphs illustrating CGM data (thick line) versus smoothed signal (thin line) during a first time window, with weighted residuals (circles) during the first time window, CGM data (thick line) versus smoothed signal (thin line) during a second time window, and weighted residuals (circles) during the second time window, respectively, for a representative sensor.
Figure 31B:
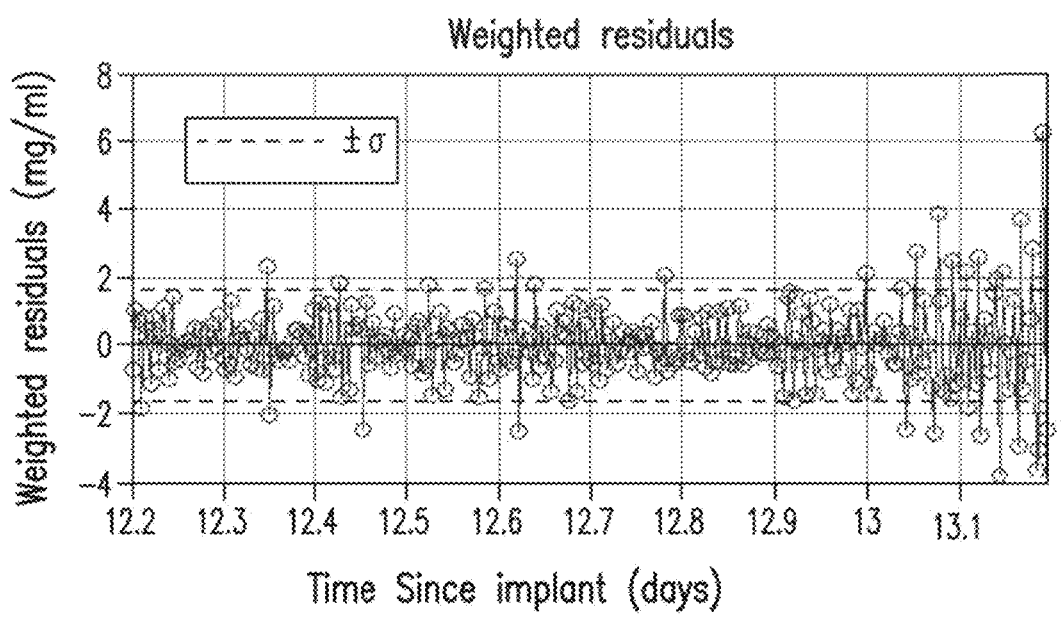
Figure 31C:
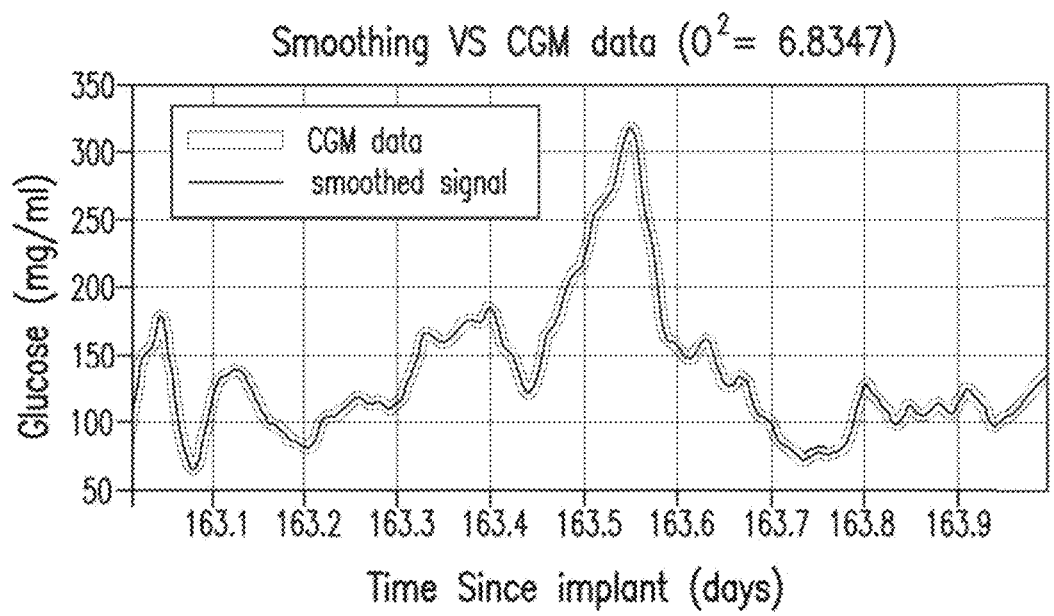
Figure 31D:
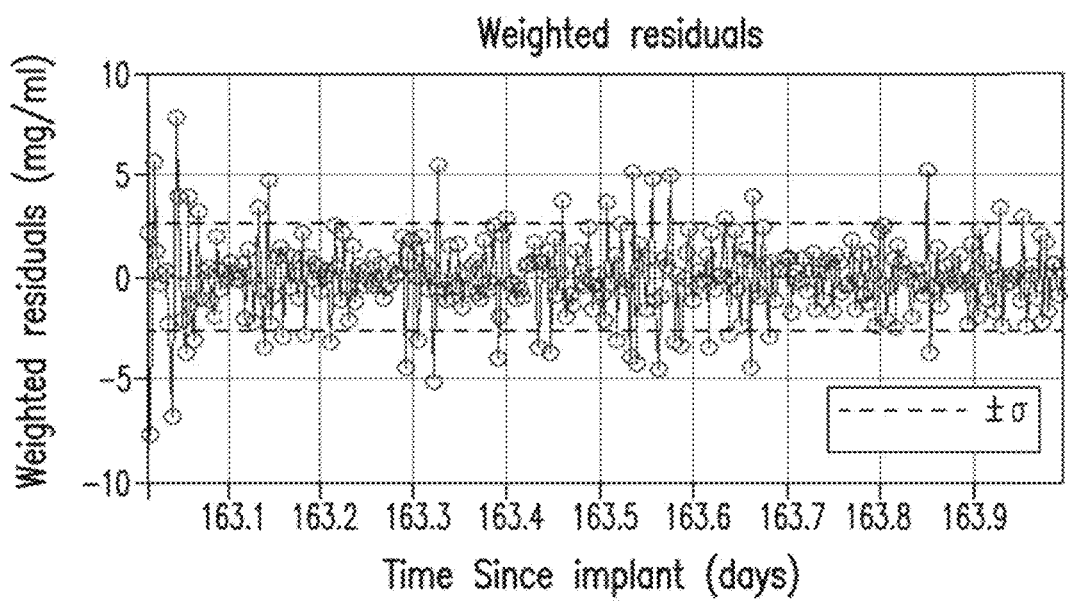

Similar results as before have been obtained using Dataset 2. For the error variance analysis, the mean and the standard deviation of the estimated parameters are: $\hat{\sigma}^2=9.44\pm11.34$ (mg$^2$/ml$^2$), $\gamma=69.95\pm142.70$, $\lambda^2=0.17\pm0.11$ (mg$^2$/ml$^2$). FIGS. 30A-30C show how the error variance changes through the time. In particular, FIGS. 30A-30C show the error variance trends of three sensors: S8589 (FIG. 30A), S8623 (FIG. 30B), and S8703 (FIG. 30C). FIGS. 31A-31D are graphs illustrating CGM data (thick line) versus smoothed signal (thin line) during a first time window, weighted residuals (circles) during the first time window, CGM data (thick line) versus smoothed signal (thin line) during a second time window, and weighted residuals (circles) during the second time window, respectively, for the sensor S23269. To assess the Bayesian smoothing, as shown in FIGS. 31A-31D, we can do a comparison between the sensor S23269 CGM data and the smoothed signal in the two different time windows, also with the respective weighted residuals trend in the ±σ (error standard deviation) band.

Figure 34A:
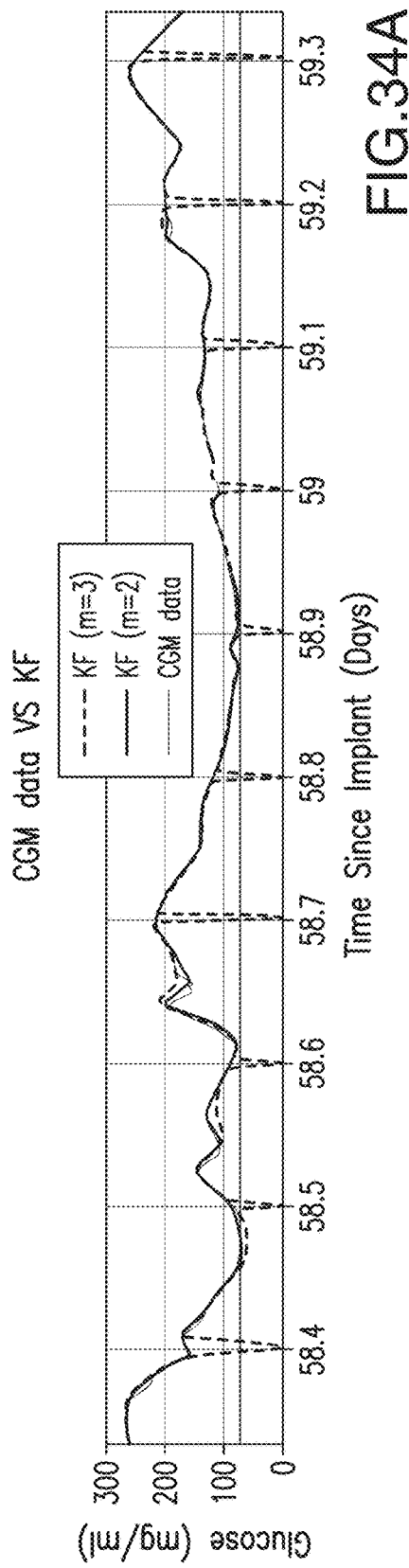
FIGS. 34A-34C are graphs illustrating KF series with m=2 (thick line) or m=3 (dashed line) integrators versus CGM data (thin line) for a representative sensor during three different time periods.
Figure 34B:
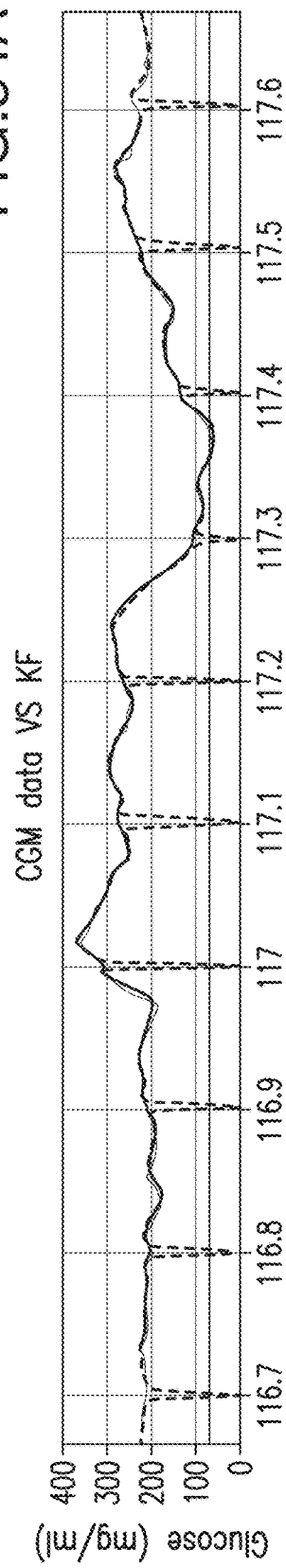
Figure 34C:
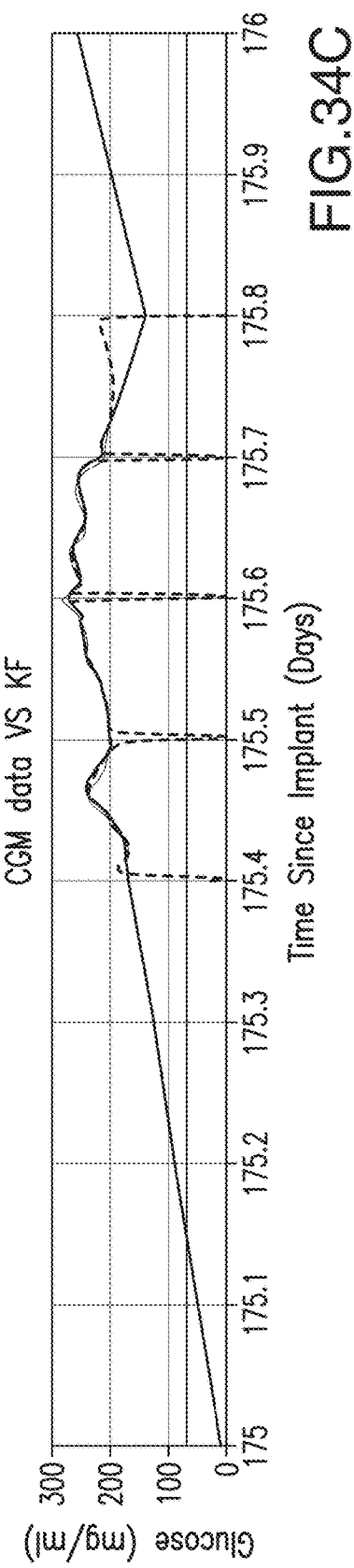
Figure 35A:
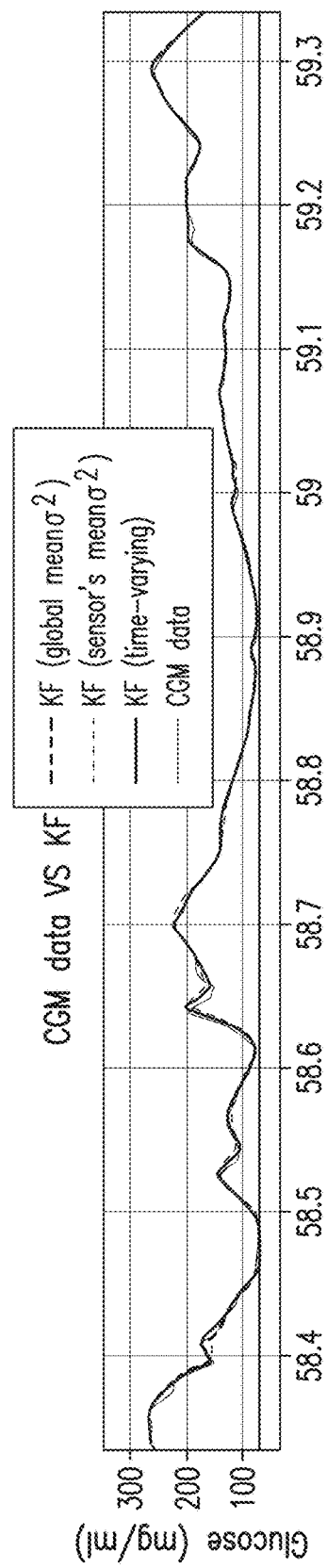
FIGS. 35A-35C are graphs illustrating KF series with time-varying (thick line), global (thick dashed line) or sensor individualized (thin dashed line) parameters versus CGM data (thin line) for a representative sensor during three different time windows.
Figure 35B:
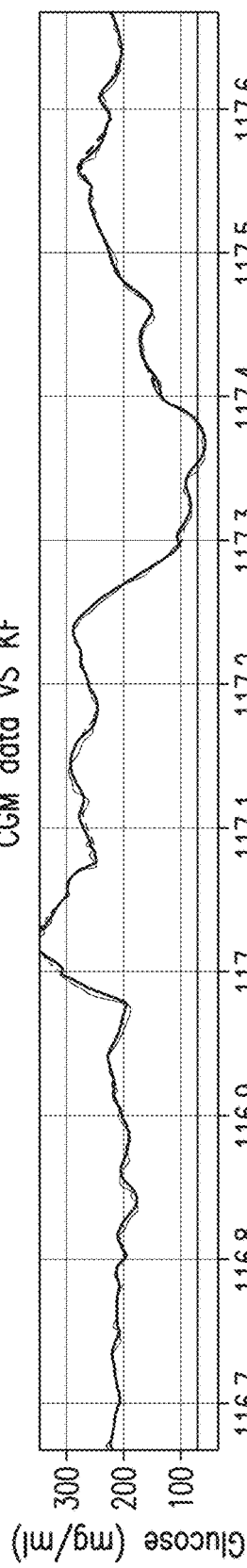
Figure 35C:
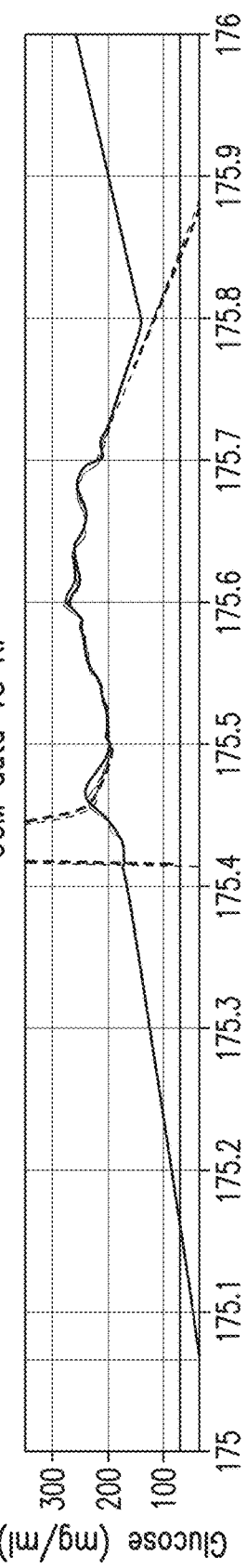

Regarding the KF assessment, FIGS. 32A-32C are graphs illustrating the CGM data (thin line) and the filtered and filled version (thick line) of sensor S23269 in three different time windows. FIGS. 33A-33C are graphs illustrating the CGM data (thin line) and the filtered and filled version (thick line) of sensor S89652 in three different time windows. FIGS. 34A-34C show KF series with an m=2 integrator (solid red), KF series with an m=3 integrator (solid magenta), and CGM data (thin line) in the three different time windows. The choice of two integrators in the KF is confirmed in FIGS. 34A-34C by comparing the filtered signal trends using the m=2 and m=3 integrators. Regarding Q and R definition, FIGS. 35A-35C are graphs showing a KF with time-varying parameters (thick line), a KF with global parameters (thick dashed line), and a KF with sensor individualized parameters (thin dashed line) along with CGM data (thin line). FIG. 36 is a table showing the assessment of the accuracy performance. In FIG. 36, the MARD and MAD metrics have been calculated between the YSI values or the FS measurements and the CGM signals including the raw (i.e., not filtered) CGM series and the three filtered CGM versions using one of time-varying, global, or sensor individualized parameters. FIG. 37 is a table showing the regularity metrics and the time lag, calculated between the raw CGM signal and the three filtered CGM series. FIG. 38 is a table showing chosen m=2 and time-varying parameters and the ROC accuracy, calculated through the concurrence of the raw CGM series and the YSI trend. FIG. 39 is a table showing chosen m=2 and time-varying parameters and the ROC accuracy, calculated through the concurrence of the filtered CGM series and the YSI trend.

4.4 Discussion

Let's start comparing Dataset 1 and Dataset 2. It can be easily checked, examining figures and tables, the increased performance of the updated algorithm: all metrics and results are better in Dataset 2 than in the first one. It must be noted, however, the increased number of missing values. In some points, the new algorithm fills some data "hole"; on the other side, instead, many data now is missing. We can compare, for example, FIGS. 22A-22C and 4.9, where some CGM data has disappeared. It means that missing values do not match only with data not collected by the transmitter 101, but also with measurements that the software cannot do. To improve that, an "intermediate" version of the software, which increases the accuracy but that doesn't make more values disappear, could be used. This increase of the number of NaN values has been also found in programs implementation: the sensor S8870 analyses in Dataset 2 has been performed, for example, starting from the 3rd day. Regarding, instead, the comparison between the numbers of the Kalman integrators, to obtain acceptable accuracy metrics, all NaN values at the end of the signal have been cancelled. In FIGS. 35-A-35C can be seen that the higher number of NaN values worsens anyway the fixed parameters filters performance. The time-varying model estimates the parameters when there are enough data, while the other models filter any value continuing to predict future states that sometimes are not physiological.

Now, the assessment of the algorithms analyzed will be done using the results obtained both with Dataset 1 and with Dataset 2. As seen in FIGS. 20A-20C and 30A-30C, the error variance analysis does not seem to change drastically through time. However, values and trends change from a sensor 100 to another: sometimes the variance does not change through time, but sometimes it grows, indicating, probably, a loss of sensor performance. In the figures can be seen, then, the presence of several spikes, maybe due to an imperfection of the computing system. For a good performance, we cannot use global or simply sensor individualized parameters: so, for a better accuracy, we need to estimate optimal time-varying parameters, as we can see comparing the MARD and MAD metrics in FIGS. 26 and 36. In real-time, from a practical standpoint, the estimates may not be calculated every time we have a new CGM value. In some embodiments, being that the Bayesian smoothing may be computationally intensive, the analyte monitoring system 1 may estimate the parameters occasionally, for example and without limitation, every 144 minutes. Then, the circles in FIGS. 20A-20C and 30A-30C correspond to whole days without missing values where it was possible to smooth the signal, to estimate the optimal parameters for the Kalman Filter. This number is thus significantly lower than the total number of the days. Changing the topic, in FIGS. 21A-21D and 31A-31D we can do a comparison between the sensor S23269 CGM data and the smoothed signal with the Bayesian based criterion. Despite the need to estimate two parameters ($\gamma$, the regularization parameter, and $\sigma^2$, the error variance), this algorithm lead to very good results, i.e. to an excellent smoothing of the raw data. As aforementioned, however, this kind of signal quality enhancement cannot be used every new value, for the high computational intensity: thus, a Kalman approach, less burdensome but also less performing, has been used. The weighted residuals in FIGS. 21B, 21D, 31B, and 31D represent, then, an estimate of a signal related to the error v(t): their random trend included in the ±a band confirms the zero-mean, constant SD, Gaussian white noise hypothesis.

Now, let's talk about the Kalman filtering. Regarding the number of Kalman integrators, in some embodiments, the best performance may be obtained using m=2, as seen in FIGS. 24A-24C and 34A-34C. However, this is not required, and some alternative embodiments may implement the KF with another number of integrators (e.g., three integrators, which may tend to predict the future state in a parabolic way, while the m=2 filter may predict them linearly). We can establish that, using individualized time-varying parameters, the accuracy and regularity metrics show a better performance estimating these parameters occasionally (cf. FIGS. 26, 27, 36 and 37). In some embodiments, the analyte monitoring system may use individualized time-varying parameters. A difference among these methods, perceptible in FIGS. 25B and 35C, occurs during long periods of missing values: as already said, these models predict future states anyhow, without having enough data to do that, leading to un-physiological values.

In some embodiments, the denoising model may be a Kalman filter with m=2 integrators and time-varying parameters. Observing FIGS. 22A-22C, 23A-23C, 32A-32C, and 33A-33C, a good reduction of the noise, and a quite good compensation of missing values can be found.

5. Prediction 5.1 Methods

In some embodiments, the analyte monitoring system 1 may exploit the continuous glucose monitoring data to prevent hypo/hyperglycemic events in real time by forecasting future glucose levels and to generate alarms, thanks to ahead-of-time prediction using the past CGM data and suitable time-series models. Data-driven models represent a class of modeling techniques where the relationships between input and output process variables, that characterize the underlying phenomenon being modeled, are learned, during the training phase, from existing input-output data. Once the relationships have been learned, given new, unseen input process data, the models can accurately predict, up to a certain Prediction Horizon (PH), the corresponding output as long as these data are within the envelope of relationships learned in the training phase. However, from a modeling perspective, before the benefits of such a strategy can be attained, it is necessary being able to quantitatively characterize the behavior of the model coefficients as well as the model predictions as a function of prediction horizon. It is needed to determine if the model coefficients reflect viable physiologic dependencies of the individual glycemic measurements and whether the model is stable with respect to small changes in noise levels, leading to accurate near-future predictions with negligible time lag.

In some embodiments, to generate alarms the analyte monitoring system 1 may predict glucose simply through linear projection, calculating the trend value as the linear slope of the finite CGM glucose in a past time period (e.g., the past 16 min), through, for example and without limitation, ordinary least squares.

The purpose of this part is to quantitatively assess different time-series models fitted against past glucose values provided by the analyte monitoring system 1, improving its prediction performance. In particular, two simple prediction models, potentially usable on-line, have been considered. The first method is based on the description of the past glucose data through a first-order Polynomial model (POL (1)). In the second method, past glucose data are described by a first-order AutoRegressive (AR(1)) model. In some embodiments, the analyte monitoring system 1 may use a first-order polynomial model identified with ordinary least squares using only the last 16 minutes data to compare it with the other two. In all methods, at each sampling time, a new set of model parameters is first identified: in POL(1) and AR(1) models by means of weighted least squares techniques, using a forgetting factor ($\mu$), while in the S method by ordinary least squares. Then, the model is used to forecast glucose level for a given prediction horizon.

Note that all models have been identified and assessed with filtered data obtained using the Kalman Filter described in Section 4: intuitively, predict using a less noisy time-series will produce more accurate and probable results.

5.1.1 First-Order Polynomial Model

Here, the glucose time-series is described, locally, by a first-order polynomial $$CGM(t_i) = m^* t_i + q \qquad (5.1)$$

where i=1, 2, ..., n denotes the order of glucose samples collected till the nth sampling time tn. Let $\theta$ denote the vector of the parameters of the model employed to describe the glucose time-series, i.e. $\theta=(m, q)$. At each sampling time tn, a new value of $\theta$ is first determined by fitting the model against past glucose data $CGM(t_n)$, $CGM(t_n-1)$, $CGM(t_n-2)$ ... by weighted linear least squares. Once $\theta$ is determined, the model is used to calculate the prediction of glucose level T steps ahead, i.e. $\theta$n+T. For a sampling interval of 3 min, a value of T equal to 10 or 15 corresponds to a PH equal to 30 or 45, respectively. The value $\theta$n+T is calculated in a straightforward fashion from the polynomial model equation. The method is obviously based on time-varying model. All the past data $CGM(t_n)$, $CGM(t_n-1)$, ..., $CGM(t_1)$ participate, with different relative weights, to the determination of $\theta$. The way with which past data are weighted is a key aspect in model fitting. Here, it have been assigned the weight $\mu$k to the sample taken k instants before the actual sampling time, i.e. $\mu$k is the weight of the sample at time $t_{n-k}$ (k=0, 1, ..., n-1). The parameter $\mu$ behaves like a forgetting factor, a parameter typically introduced in the modeling of nonstationary processes in order to improve the fit of the most recent data. If the forgetting factor were not used (which is equivalent to letting $\mu=1$), glucose samples collected tens of hours, if not days, before the actual sampling time would influence prediction, with a significant deterioration of the algorithm capability to promptly track changes in the signal, in particular those due to perturbations, e.g. meals. In some embodiments, the analyte monitoring system 1 may uses this approach, weighting the same way previous data (e.g., the last 16 minutes data) with a forgetting factor equal to, for example, 1. The forgetting factor, thus, belongs to the range [0, 1] and its value regulates the length of the "memory" of the past data that participate to the determination of $\theta$: the higher the $\mu$, the longer the memory, the lower the $\mu$, the more quickly we forget the past data. Finally, a closed-form expression has been used to determine $\theta=(m, q)$.

5.1.2 First-Order Autoregressive Model

The AR model of first-order correspond to the following time-domain difference equation $$CGM(t_i) = aCGM(t_{i-1}) + w(t_i) \qquad (52)$$

where i=1, 2, ..., n denotes the order of glucose samples collected till the $n^{th}$ sampling time $t_n$ and $w(t_i)$ is a random white noise process with zero mean and variance equal to $\sigma^2$. For glucose concentrations to be predictable with AR models, the CGM data must possess "detectable structure" and the dynamics of the time-series data should, ideally, be stationary. By definition, a process is considered stationary when the sample mean and variance of the process measurements are constant with respect to time and the autocorrelation function is independent of absolute time. Indication of the stationary nature of the underlying process, before applying AR models, has been found empirically by observing the CGM tracks behavior. Here the vector of the parameters is $\theta=(a, \sigma^2)$. As in the POL(1) model, at each sampling time $t_n$, the new value of $\theta$ is determined by fitting the model against past glucose data by weighted linear least squares. The model is then used to calculate the prediction parameters: the value of $\theta_n+T$ is calculated using iteratively the time-domain model difference equation for i=n+1, n+2, . . . , n+T, substituting the sample of the w process with the corresponding expected value (i.e., 0), and the variables not yet observed with the predicted values. The method, therefore, is based on time-varying model, and uses a forgetting factor ($\mu$) to weight the past data as well. Here, finally, a recursive least square algorithm was employed to determine $\theta=(a, \sigma^2)$.

5.2 Implementation

In some embodiments, after loading the data, the analyte monitoring system 1 may extract the various series, i.e. filtered CGM and YSI from the structures. To make comparable the results, all data is then considered from the 2nd. The POL(1) and AR models have been applied and identified with three different p values (e.g., 0.5, 0.75 and 0.9), meanwhile the methods predict glucose at three different PH (e.g., 20, 30 and 40 minutes). The POL(1) and S method have been identified using, respectively, Weighted Least Squares (WLS) and Ordinary Least Squares (OLS) method, while the AR(1) model is identified using a Recursive Least Square algorithm. In some embodiments, a bound may be put on our prediction: when it falls outside a range (e.g., the [40, 400] (mg/dl) range), it is fixed to 40 or 400 mg/dl, respectively.

Regarding NaN, during the model implementation, in some embodiments, the analyte monitoring system 1 may substitute CGM missing values with the predicted value at the same time: if by that time no value has been predicted yet, the previous acceptable value is used. Seen the high number of NaN values, to improve the prediction performance, moreover, when 5 missing values consecutively occur in the CGM series, the prediction stops and restarts over.

The models performance is assessed calculating the Root Mean Squared Error (RMSE), between the raw signal and the predicted series, and the Energy of the Second-Order Differences (ESOD), for each combination of □ and PH. Then, the time delay between the CGM series and the predicted one is calculated through different ways. An average delay and the corresponding Time Gain (TG=PH−delay) is calculated using the cross-correlation: as known, the delay is the lag, used to calculate the cross-correlation, which maximize it. Another assessment of the delay consists in measuring the times at which some thresholds are crossed in the original and in the predicted glucose time-series. A natural choice for these thresholds would be the levels that define the normal glycemic range (70-180 mg/dl). However, since in our 42 time-series the hyperglycemic level was frequently exceeded, a wider set of "evaluation" threshold levels has been used: the $5^{th}$ and the 95th percentile of the glucose time-series, and the ipoglycemic threshold (i.e. 70 mg/ml). The information obtained from this analysis is also used to count the number of peak, nadir and ipoglycemic events, and consequently the number of false alarms.

The data we have are from an un-blinded system, so there is a good chance that users react to their sensor glucose and make the prediction more difficult. However, during the clinical sessions, the sensor glucose is blinded so no action is done. To evaluate the performance during the clinical session, the RMSE and accuracy metric like MARD and MAD of prediction against YSI have been calculated. Since then, we have calculated a new trend value, and we have checked if this gives a better trend accuracy compared to YSI trend, quantified with the usual concurrence ROC table. As though the YSI measurements are less than the CGM ones, the comparison between these signals is allowed through matching: CGM data, filtered and not, that are not associated to reference value is eliminated. Regarding the missing values, the matched signals, with no missing values, have been used for the metrics of accuracy calculation (MARD, MAD, and ROC) and for the RMSE assessment. As for the ESOD evaluation, instead, the missing values have been set to zero. Regarding the cross-correlation time lag, after replacing the NaN values with a mean signal value, the CGM signal has been normalized $$\left(\frac{CGM - \text{mean}(CGM)}{std(CGM)}\right)$$

since strongly influenced by outliers, the calculation of the mean has been made on a moving-average smoothed version of the signal. It must be noted that all analyses are repeated for both dataset. In particular, then, note that the analysis of the sensor S8870 in Dataset 2 is performed starting from the 3rd day, because of the too high number of NaN values.

5.3 Results 5.3.1 Dataset 1

Figure 40:
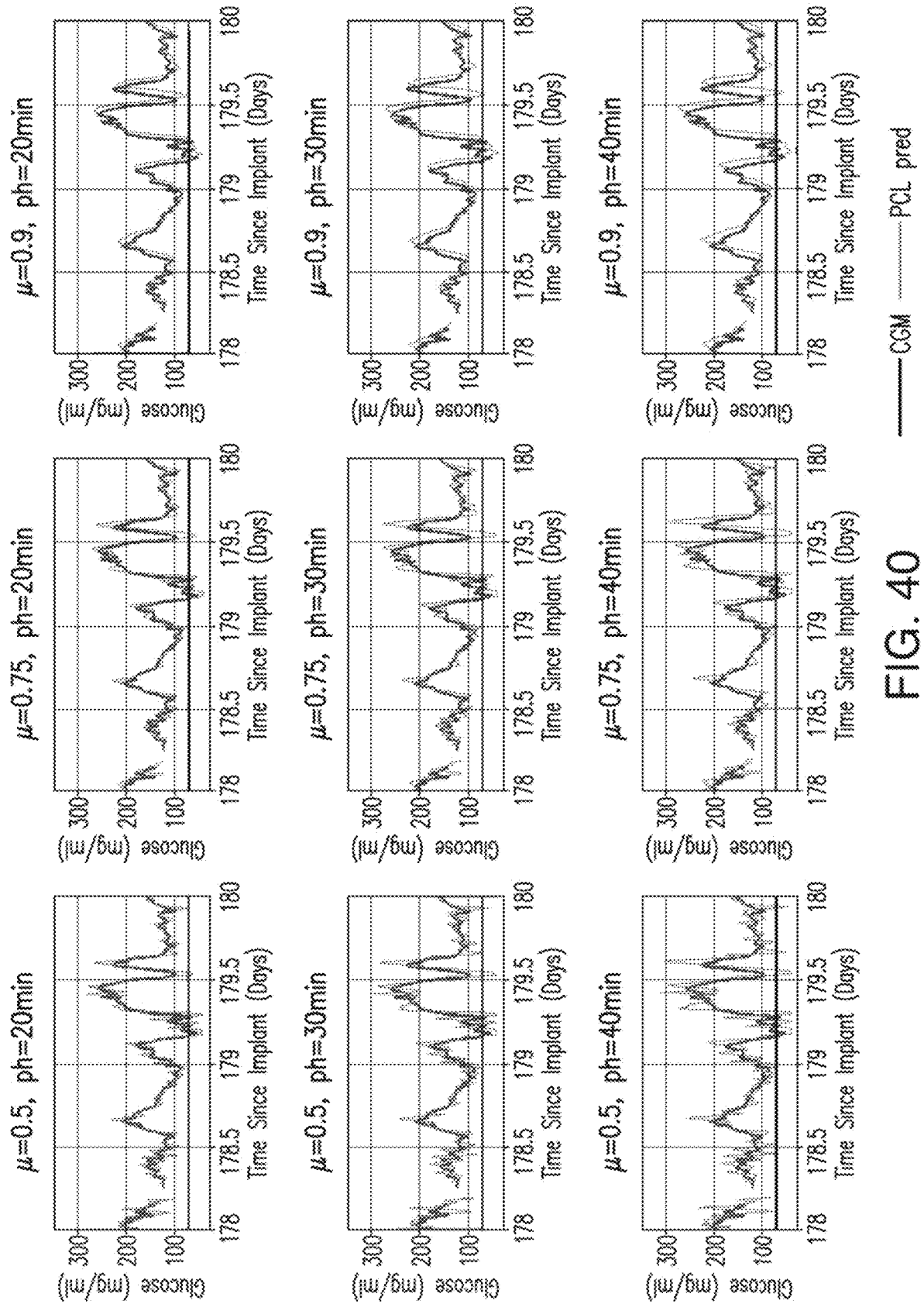
FIG. 40 is graphs illustrating original (thick line) versus predicted (thin line) time-series (top to bottom PH=20, 30 and 40 min; left to right μ=0.5, 0.75 and 0.9) with a POL(1) model for a representative sensor.
Figure 41:
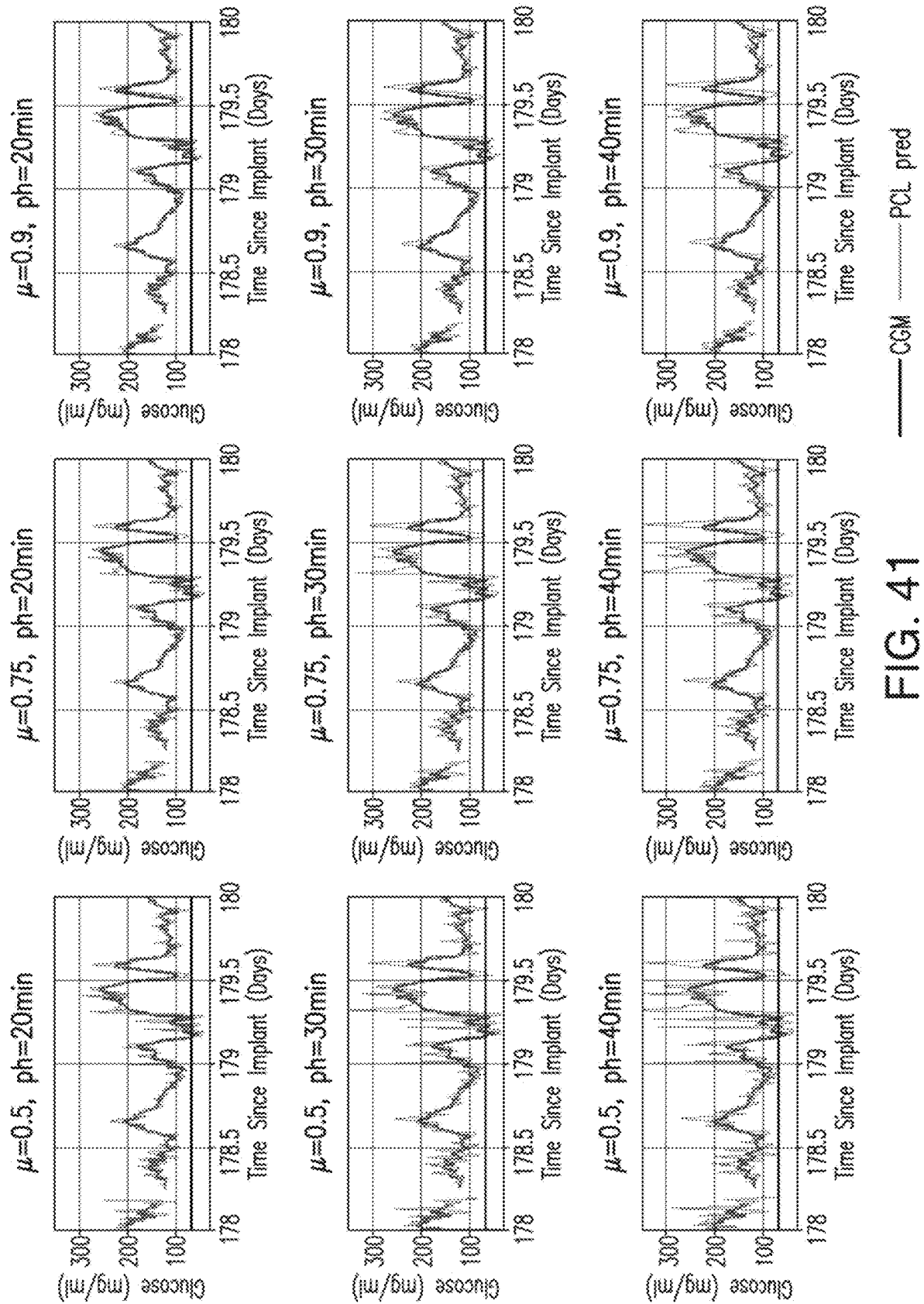
FIG. 41 is graphs illustrating original (thick line) versus predicted (thin line) time-series (top to bottom PH=20, 30 and 40 min; left to right μ=0.5, 0.75 and 0.9) with AR(1) model for a representative sensor.
Figure 42A:
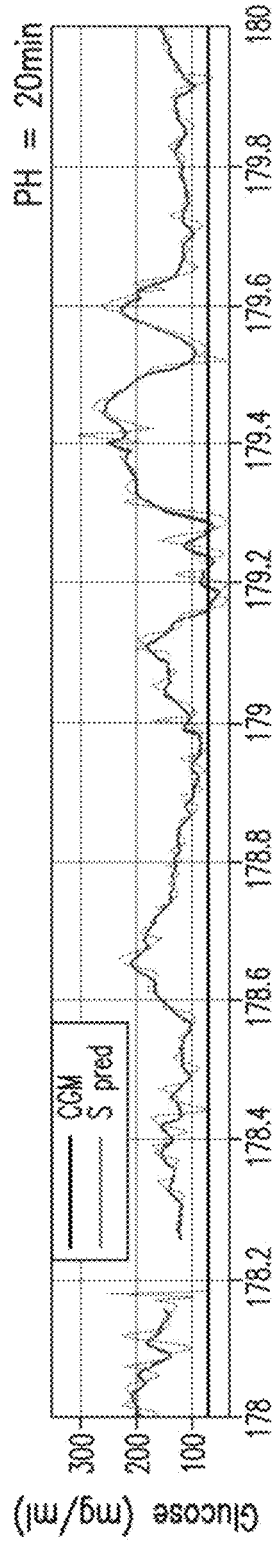
FIGS. 42A-42C are graphs illustrating original (thick line) versus predicted (thin line) time-series (top to bottom PH=20, 30 and 40 min) with an existing Senseonics approach for a representative sensor.
Figure 42B:
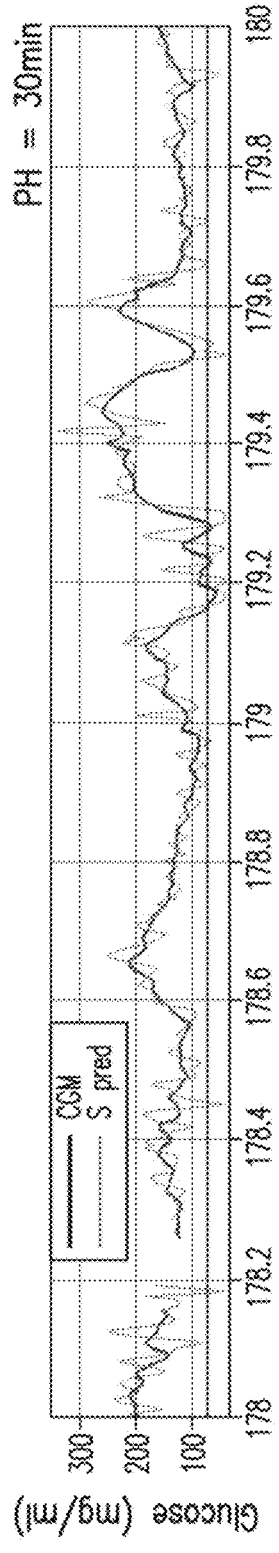
Figure 42C:
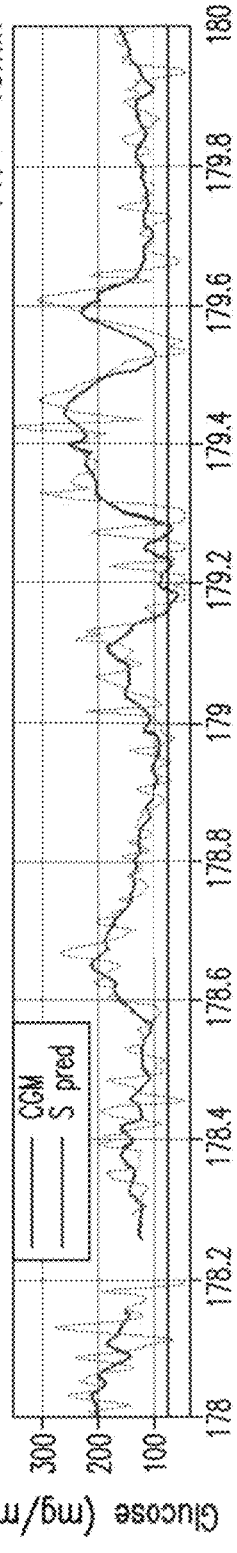

To confirm the optimal choice to predict on filtered instead of on raw data, the mean time delay of POL(1) model has been calculated on the representative sensor S23269. Using filtered data we obtain a delay of 5.83 min, while using raw data we have 6.97 min. FIG. 40 shows the original CGM (thick line) versus predicted (thin line) time-series of the polynomial model in the representative sensor S23269 for μ=0.5 (left column), μ=0.75 (middle column), μ=0.9 (right column), and for PH=20 min (top row), PH=30 min (middle row) and PH=40 min (bottom row). FIG. 41 shows the same result for the AR(1) model. FIGS. 42A-42C are graphs representing the existing Senseonics approach. FIG. 43 is a table offering a quantitative assessment of the results in all 42 subjects by reporting mean and standard deviation of the Root Mean Square Error (RMSE) between the original and the predicted time-series, and of the Energy of the Second-Order Differences of the predicted profile (ESOD). FIG. 44 is a table showing the average delay calculated with cross-correlation. FIG. 45 is a table showing the average delays for which threshold crossings can be detected (together with standard deviation SD) for each model. FIG. 46 is table showing the number of peak, nadir and ipoglycemic events, and consequently the number of false alarms. FIG. 47 is a table showing as assessment of the prediction performance during the clinical session with RMSE, MARD and MAD of prediction against YSI. One combination of forgetting factor and prediction horizon has been chosen as the best (e.g., p=0.9 and PH=20 minutes) for each prediction model. FIGS. 48-50 are tables showing the ROC accuracy, calculated through the concurrence of the predicted time-series and the YSI trend, for the POL(1), AR(1) and S model, respectively, for the aforementioned best combination.

5.3.2 Dataset 2

Figure 51:
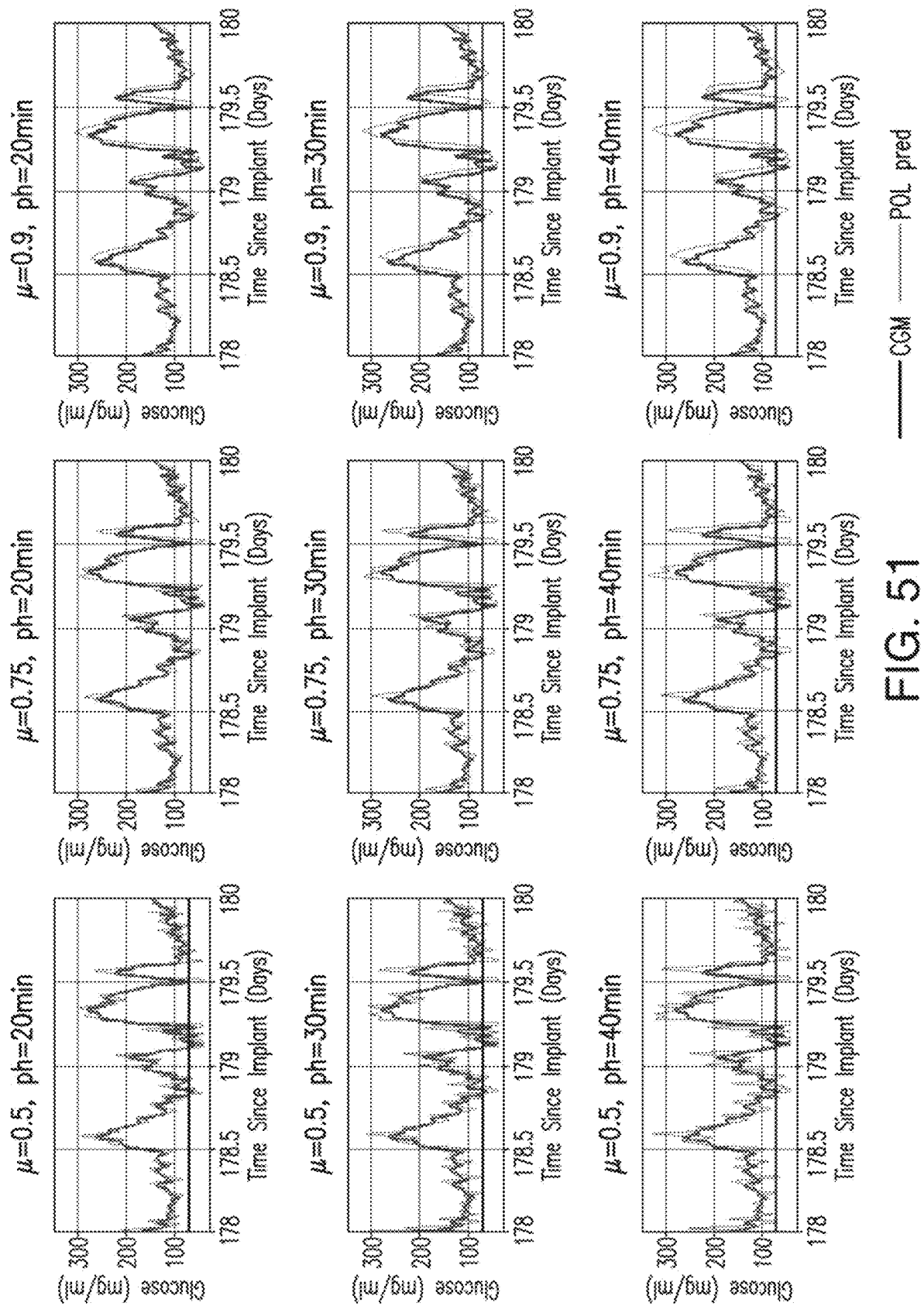
FIG. 51 is graphs illustrating original (thick line) versus predicted (thin line) time-series (top to bottom PH=20, 30 and 40 min; left to right p=0.5, 0.75 and 0.9) with a POL(1) model for a representative sensor.
Figure 52:
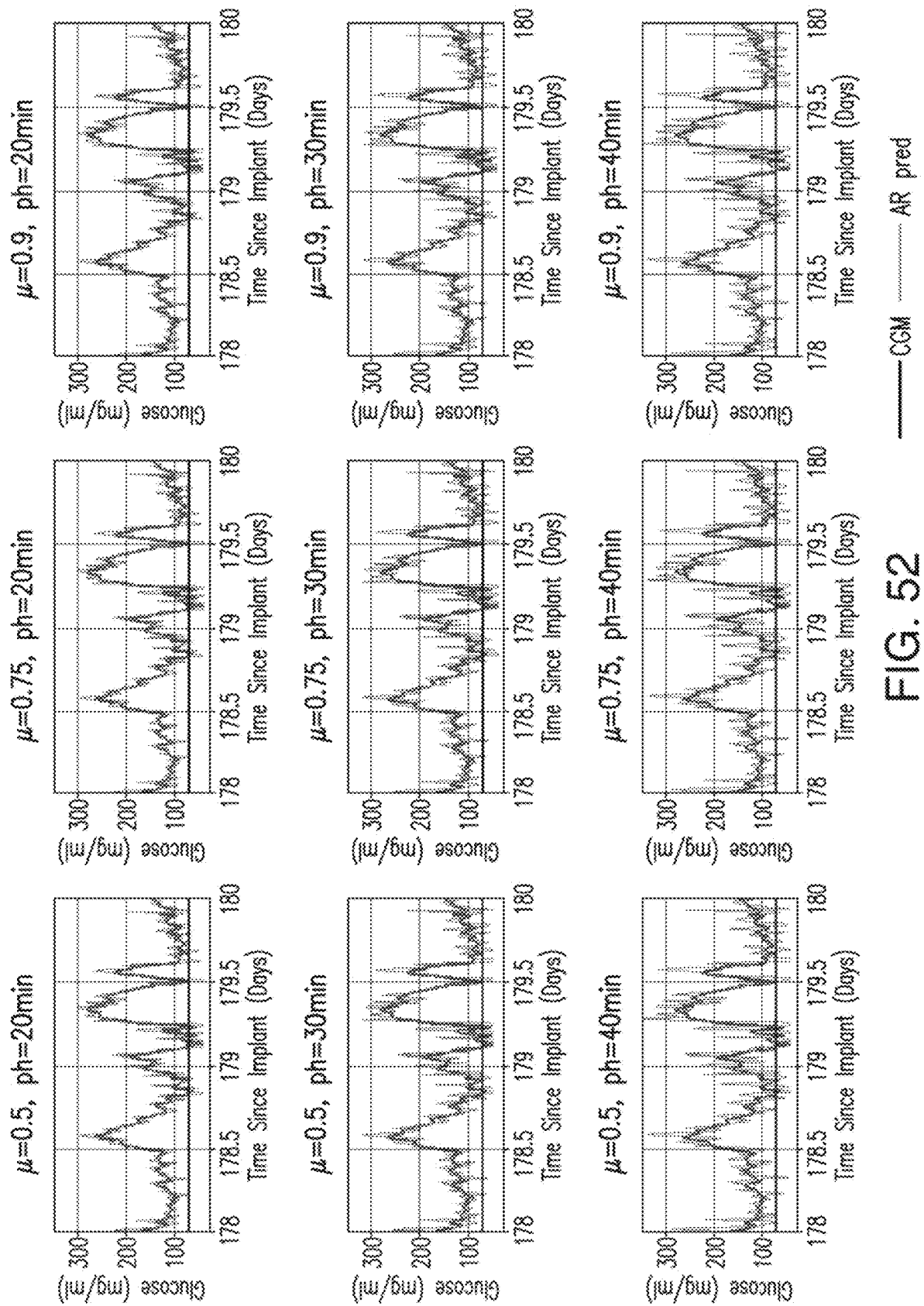
FIG. 52 is graphs illustrating original (thick line) VS predicted (thin line) time-series (top to bottom PH=20, 30 and 40 min; left to right p=0.5, 0.75 and 0.9) with an AR(1) model for a representative sensor.
Figure 53A:
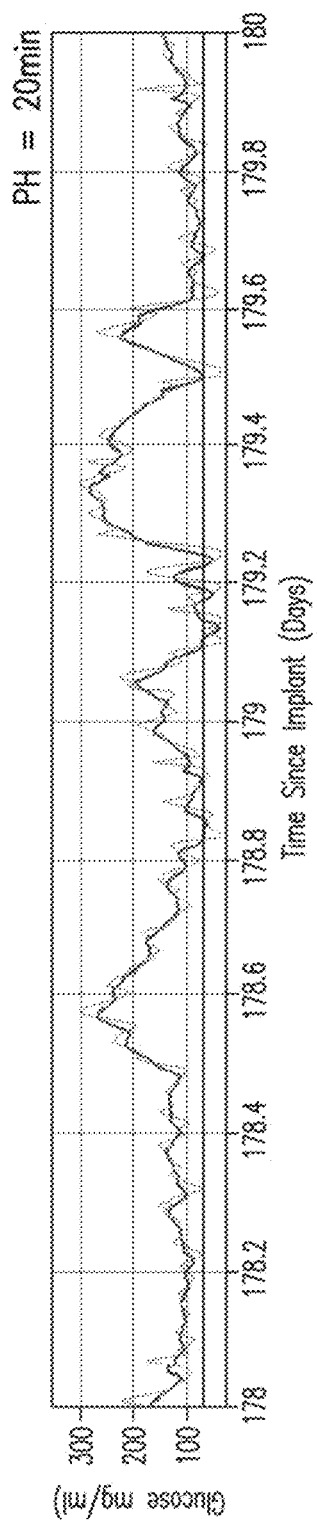
FIGS. 53A-53C are graphs illustrating original (thick line) versus predicted (thin line) time-series (top to bottom PH=20, 30 and 40 min) with an existing Senseonics approach for a representative sensor.
Figure 53B:
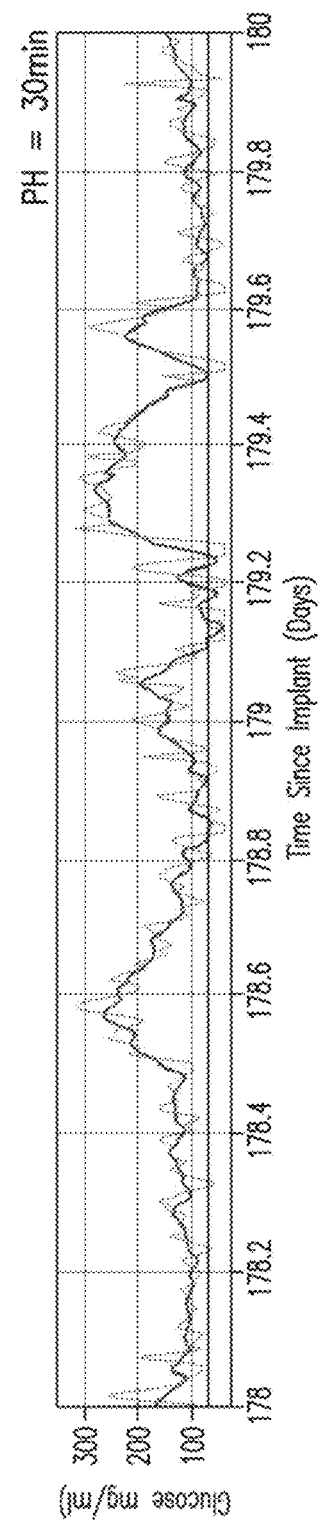
Figure 53C:
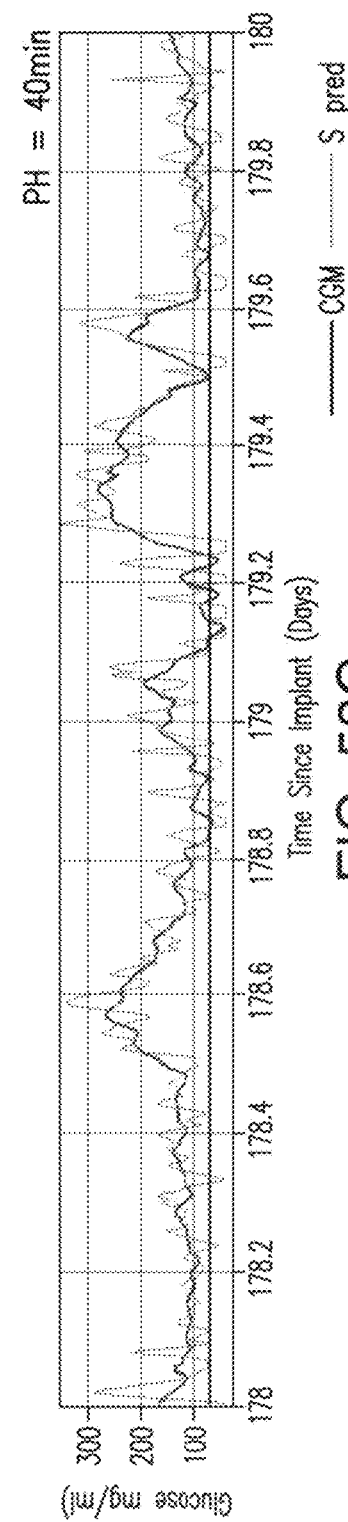

Following are the results of Dataset 2 analyses. The mean time delay of POL(1) model has been calculated on the representative sensor S23269. FIG. 51 shows the original CGM (thick line) versus predicted (thin line) time-series of the polynomial model in the representative sensor S23269 for $\mu=0.5$ (left column), $\mu=0.75$ (middle column), $\mu=0.9$ (right column), and for PH=20 min (top row), PH=30 min (middle row) and PH=40 min (bottom row). FIG. 52 shows the same result for the AR(1) model. FIGS. 53A-53C are graphs representing the existing Senseonics approach. FIG. 54 is a table offering a quantitative assessment of the results in all 42 subjects by reporting mean and standard deviation of the Root Mean Square Error (RMSE) between the original and the predicted time-series, and of the Energy of the Second-Order Differences of the predicted profile (ESOD). FIG. 55 is a table showing the average delay calculated with cross-correlation. FIG. 56 is a table showing the average delays for which threshold crossings can be detected (together with standard deviation SD) for each model. FIG. 57 is table showing the number of peak, nadir and ipoglycemic events, and consequently the number of false alarms. FIG. 58 is a table showing as assessment of the prediction performance during the clinical session with RMSE, MARD and MAD of prediction against YSI. One combination of forgetting factor and prediction horizon has been chosen as the best (e.g., p=0.9 and PH=20 minutes) for each prediction model. FIGS. 59-61 are tables showing the ROC accuracy, calculated through the concurrence of the predicted time-series and the YSI trend, for the POL(1), AR(1) and S model, respectively, for the aforementioned best combination.

5.4 Discussion

The results don't point out big differences between the prediction performance using Dataset 1 instead of Dataset 2. Only comparing the tables of FIGS. 43 and 54 it can be noticed that the regularity metrics, RMSE and ESOD, are lower, thus the performance better, in Dataset 2. The assessment of the algorithms analyzed will be done using the results obtained both with Dataset 1 and with Dataset 2, only referring on Dataset 1 figures and tables.

From a qualitative point of view, the FIGS. 40, 41, and 42A-42C suggest that the performance of each methods is acceptable. The RMSE in the table of FIG. 43 is similar with each models, denoting that none of the three seems to be superior to the other. Also, the same figures show that, with the same $\mu$, the predicted profiles of the polynomial model are slightly smoother than those of AR(1) and S models (as also confirmed by ESOD values in the table of FIG. 43), but exhibit a more consistent overshooting in correspondence to changes in the sign of the first time-derivative. As far as influence of PH on quality of prediction is concerned, an increase of PH causes, as expected, a larger prediction error and wider oscillations in predicted profiles. This is well visible from the figures, and is reflected in RMSE and ESOD values with PH=40 much higher than with PH=30 or 20 min. Finally, FIGS. 41-50 illustrate well the role of the forgetting factor. A low value of $\mu$ ("short" memory of past glucose, left panels) renders the prediction algorithm able to track changes in the time-series trend (RMSE relatively small), at the price of a higher sensitivity to noise (ESOD relatively large). In contrast, a high value of $\mu$ ("long" memory of past glucose, right panels) results in a more stable prediction profile (ESOD relatively small), at the cost of losing the ability to promptly track changes in the glucose trend (RMSE relatively large). In a patient perspective, oscillations in the prediction profile are obviously undesirable, since they can facilitate the generation of false hypo/hyper-alerts. On the opposite, a delay of the prediction profile comparable to PH (or larger) would make the approach useless in practice.

The delay in the predicted profile is quantitatively evaluated. This quantification in each individual CGM time-series will also allow assessment of the average performance of the three prediction strategies in the entire database. Both calculated using the cross-correlation and at threshold crossing (cf. the tables of FIGS. 44 and 45, 55 and 56), the time lag between the CGM data and the prediction is lower (consequently the time gain greater) using a forgetting factor instead of not using it. As expected, the smaller is p, the smaller the delay, but the greater its variability relative to the mean, with the inherent increase of the possibility of generating false alarms. However, the main result emerging from the table of FIG. 45 is that crossing of some preselected threshold levels can be detected from the predicted time-series with a delay that is significantly lower than PH. For instance, using the average cross-correlation delay, with the existing Senseonics approach and PH=40, there is, on average, a delay of only 23.10 min. With AR(1) model, even with $\mu=0.9$ (which gives the smoothest profile but the largest delay), this delay is reduced to 12.73 min. With POL(1) model, the delay seems to be even negative. In other words, even in the worst case, there is a gain in time of nearly 30 min usable for alert generation.

In some embodiments, the system 1 may use the forgetting factor. If all the past data were considered with equal weight, i.e., $\mu=0.9$, smooth but consistently delayed predicted profiles with no practical usefulness would be obtained. Indeed, in the table of FIG. 46, a better performance of AR(1) or POL(1) predictions, that use a forgetting factor, can be seen by comparing the number of peak, nadir and ipoglycemic events. In some embodiments, the use of a forgetting factor may, on average, result in a lower number of false alarms. Regarding the performance during the clinical sessions, the accuracy metrics in the table of FIG. 47 do not show a significant difference between the three prediction models. Instead, comparing the tables of FIGS. 48-50, the ROC accuracy shows a better performance using the present invention.

The results have been obtained on filtered glucose time-series, in order to remove artifacts. For these time-series with the considered PH, the AR(1) model of order 1 was the most reliable to obtain a clinically significant prediction performance (AR models of higher orders often provided unstable predictions).

The AR and WLS polynomial models of the present invention are preferable to OLS approach modeling because they may be more accurate, may generate a smaller amount of false alarms, and may present lower time delays and consequently a greater gain in time usable for alert generation.

Continuous glucose monitoring systems can be very useful in the management of diabetes, and CGM sensors are key in several applications, for instance, in systems for real-time detection of hypo/hyperglycemic events and closed-loop algorithms for the Artificial Pancreas. Suitable real-time algorithms may (e.g., real-time denoising and/or prediction algorithms) render CGM sensor more reliable with possible great benefit in applications based on CGM devices. CGM data are affected by several sources of error, including bias errors (due to imperfect/loss of calibration or to the physics/chemistry of the sensor) and random noise, which dominates the true signal at high frequency. The reduction of this last component has been dealt with by online digital filtering. An online self-tunable CGM filtering methodology implemented by KF has been used, and the novelty of this method was the possibility of using a stochastically based smoothing criterion, which can work in real-time to cope both with variations from individual to individual and from sensor to sensor. The present is applicable (in addition to denoising the signal) to compensate the large amount of missing values of the data. Results show that online tuning and individualization on KF parameters are necessary to avoid suboptimal filtering. From a clinical point of view, the reduction of the noise introduced by the filter can be of remarkable importance, because it can allow the CGM device to generate hypo/hyperglycemic alerts more timely, thus reducing the time spent in hypo/hyperglycemia by the patient. In addition, the improvement of the quality of the CGM signal can limit the number of false alerts, which is of crucial importance, especially overnight. Due to the online and fully-automated tuning procedure for KF parameters estimation, the present invention is able to cope with both sensor-to-sensor and individual to-individual variability of CGM data, and due to the real-time feature, it can be embedded in analyte monitoring systems to improve their performance.

Regarding the prediction, two simple models have been applied, assessed and compared with the existing Senseonics approach. The CGM time-series have been described by a model with fixed structure but with time-varying parameters that, at each sampling time, are re-adjusted based on the newly collected glucose sample. Since the model has to describe the time-series only "locally," its complexity is kept modest, a crucial aspect for using prediction algorithms in real-time. The performance of the algorithms was assessed by considering both classical signal estimation indices (i.e., ESOD and RMSE) as well as delay indices, which may be important in a clinical/patient context. Results quantitatively demonstrate that glucose prediction from past data is feasible, that the performance of prediction algorithms is adequate for preventing hypo/hyperglycemic events, and that using more complex models, in particular with a forgetting factor, can improve system performance. Some embodiments may use Bayesian filtering approaches as well as more sophisticated autoregressive models, e.g., ARI, ARIMA, or regularized AR models. Furthermore, the chosen order of the AR model and the value of the forgetting factor may reflect the sampling rate (e.g., the higher is the sampling frequency, the higher should be the model order). In addition, the maximum allowable PH may be matter of investigation. A new index that can optimally design the prediction algorithm parameters was proposed. Another possible improvement concerns the inclusion of additional information in the prediction algorithm, such as timing and composition of meals (e.g., a method exploiting neural networks) or level of physical activity measured in real-time, which are not exploited by the current prediction algorithm.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. An analyte monitoring system comprising:
an analyte sensor including an analyte indicator that exhibits one or more detectable properties based on an amount or concentration of an analyte in proximity to the analyte indicator, wherein the analyte sensor is configured to generate one or more raw signals indicative of one or more analyte amounts or concentrations; and
a transmitter configured to (i) receive from the analyte sensor one or more first raw signals indicative of analyte concentration, (ii) estimate one or more time-varying parameters for a real-time filtering technique at a first time, (iii) denoise the one or more first raw signals using a real-time filtering technique with the one or more time-varying parameters estimated at the first time, (iv) receive from the analyte sensor one or more second raw signals indicative of analyte concentration, (v) estimate the one or more time-varying parameters for the real-time filtering technique at a second time, and (vi) denoise the one or more second raw signals using the real-time filtering technique with the one or more time-varying parameters estimated at the second time;
wherein the one or more time-varying parameters include an error variance.

2. The analyte monitoring system of claim 1, wherein the real-time filtering technique includes Kalman filtering.

3. The analyte monitoring system of claim 1, wherein the real-time filtering technique compensates for the presence of one or more missing values in the received one or more raw signals.

4. The analyte monitoring system of claim 1, wherein the one or more time-varying parameters include a parameter $\lambda^2$, where $\lambda$ represents a degree to which a slope from a current time window is desired to be close to the slope from a previous time window.

5. The analyte monitoring system of claim 1, wherein the one or more time-varying parameters are estimated day-by-day.

6. The analyte monitoring system of claim 1, wherein the one or more time-varying parameters are estimated only every 144 minutes using the last 6 hours of data.

7. The analyte monitoring system of claim 1, wherein the one or more time-varying parameters are estimated using a stochastically based smoothing criterion that is based on data of a burn-in interval.

8. The analyte monitoring system of claim 1, wherein the transmitter is further configured to predict ahead of time an analyte concentration based on at least one or more of the received one or more first raw signals.

9. The analyte monitoring system of claim 8, wherein the transmitter is configured to use a forgetting factor $\mu$ to regulate how the one or more first raw signals are used to predict ahead of time the analyte concentration.

10. The analyte monitoring system of claim 8, wherein the transmitter is configured to predict ahead of time the analyte concentration based on at least the one or more of the received one or more first raw signals using one or more prediction models including a first-order polynomial model.

11. The analyte monitoring system of claim 8, wherein the transmitter is configured to predict ahead of time the analyte concentration based on at least the one or more of the received one or more first raw signals using one or more prediction models including a first-order autoregressive model.

12. The analyte monitoring system of claim 8, wherein the transmitter is configured to predict ahead of time the analyte concentration based on at least the one or more of the received one or more first raw signals using one or more prediction models including Kalman filtering.

13. The analyte monitoring system of claim 8, wherein the transmitter is configured to predict ahead of time the analyte concentration based on at least the one or more of the received one or more first raw signals using one or more prediction models including one or more artificial neural networks.

14. An analyte monitoring method comprising:
using an analyte sensor to generate one or more raw signals indicative of one or more analyte amounts or concentrations, wherein the analyte sensor includes an analyte indicator that exhibits one or more detectable properties based on an amount or concentration of an analyte in proximity to the analyte indicator;
using a transmitter to receive from the analyte sensor one or more first raw signals indicative of analyte concentration;
using the transmitter to estimate one or more time-varying parameters for a real-time filtering technique at a first time, wherein the one or more time-varying parameters include an error variance;
using the transmitter to denoise the one or more first raw signals using the real-time filtering technique with the one or more time-varying parameters estimated at the first time;
using the transmitter to receive from the analyte sensor one or more second raw signals indicative of analyte concentration;
using the transmitter to estimate the one or more time-varying parameters for the real-time filtering technique at a second time; and
using the transmitter to denoise the one or more second raw signals using the real-time filtering technique with the one or more time-varying parameters estimated at the second time.

15. An analyte monitoring system comprising:
an analyte sensor including an analyte indicator that exhibits one or more detectable properties based on an amount or concentration of an analyte in proximity to the analyte indicator, wherein the analyte sensor is configured to generate one or more raw signals indicative of one or more analyte amounts or concentrations; and
a transmitter configured to (i) receive from the analyte sensor one or more first raw signals indicative of analyte concentration, (ii) estimate one or more time-varying parameters for a real-time filtering technique at a first time, (iii) denoise the one or more first raw signals using the real-time filtering technique with the one or more time-varying parameters estimated at the first time, (iv) receive from the analyte sensor one or more second raw signals indicative of analyte concentration, (v) estimate the one or more time-varying parameters for the real-time filtering technique at a second time, and (vi) denoise the one or more second raw signals using the real-time filtering technique with the one or more time-varying parameters estimated at the second time;
wherein the one or more time-varying parameters include a parameter $\lambda^2$, where $\lambda$ represents a degree to which a slope from a current time window must be close to the slope from a previous time window.

16. An analyte monitoring method comprising:
using an analyte sensor to generate one or more raw signals indicative of one or more analyte amounts or concentrations, wherein the analyte sensor includes an analyte indicator that exhibits one or more detectable properties based on an amount or concentration of an analyte in proximity to the analyte indicator;
using a transmitter to receive from the analyte sensor one or more first raw signals indicative of analyte concentration;
using the transmitter to estimate one or more time-varying parameters for a real-time filtering technique at a first time, wherein the one or more time-varying parameters include a parameter $\lambda^2$, where $\lambda$ represents a degree to which a slope from a current time window must be close to the slope from a previous time window; and
using the transmitter to denoise the one or more first raw signals using the real-time filtering technique with the one or more estimated time-varying parameters estimated at the first time;
using the transmitter to receive from the analyte sensor one or more second raw signals indicative of analyte concentration;
using the transmitter to estimate the one or more time-varying parameters for the real-time filtering technique at a second time; and
using the transmitter to denoise the one or more second raw signals using the real-time filtering technique with the one or more time-varying parameters estimated at the second time.

* * * * *